(12) United States Patent
Knight et al.

(10) Patent No.: US 10,767,476 B2
(45) Date of Patent: Sep. 8, 2020

(54) MICROBIOME BASED SYSTEMS, APPARATUS AND METHODS FOR THE EXPLORATION AND PRODUCTION OF HYDROCARBONS

(71) Applicant: Biota Technology, Inc., San Diego, CA (US)

(72) Inventors: Rob Knight, San Diego, CA (US); Ajay Kshatriya, Oakland, CA (US); John Ely, Houston, TX (US); Paul Henshaw, Clayton, CA (US); J. Gregory Caporaso, Flagstaff, AZ (US); Dan Knights, St. Paul, MN (US); Ryan Gill, Denver, CO (US)

(73) Assignee: Biota Technology, Inc., San Diego, CA (US)

( * ) Notice: Subject to any disclaimer, the term of this patent is extended or adjusted under 35 U.S.C. 154(b) by 341 days.

(21) Appl. No.: 15/641,965

(22) Filed: Jul. 5, 2017

(65) Prior Publication Data

US 2017/0370213 A1 Dec. 28, 2017

Related U.S. Application Data

(63) Continuation of application No. 15/087,552, filed on Mar. 31, 2016, now Pat. No. 9,771,795, which is a
(Continued)

(51) Int. Cl.
*C12Q 1/68* (2018.01)
*G06N 99/00* (2019.01)
(Continued)

(52) U.S. Cl.
CPC .............. *E21B 49/08* (2013.01); *C09K 8/582* (2013.01); *C09K 8/62* (2013.01); *C12Q 1/689* (2013.01);
(Continued)

(58) Field of Classification Search
CPC ...... E21B 49/08; E21B 49/086; E21B 21/065; E21B 49/003; E21B 43/267; E21B 43/26;
(Continued)

(56) References Cited

U.S. PATENT DOCUMENTS

| 5,593,883 A | 1/1997 | Cano et al. |
| 6,543,535 B2 * | 4/2003 | Converse ................. C09K 8/58 166/246 |

(Continued)

FOREIGN PATENT DOCUMENTS

| WO | WO-2011098770 A1 | 8/2011 |
| WO | WO-2015103165 A1 | 7/2015 |

(Continued)

OTHER PUBLICATIONS

"U.S. Appl. No. 14/585,078, Advisory Action dated Oct. 11, 2018", 3 pgs.
(Continued)

*Primary Examiner* — Mohammad K Islam
(74) *Attorney, Agent, or Firm* — Schwegman Lundberg & Woessner, P.A.

(57) ABSTRACT

There are provided methods, systems and processes for the utilization of microbial and related genetic information for use in the exploration, determination, production and recovery of natural resources, including energy sources, and the monitoring, control and analysis of processes and activities.

17 Claims, 19 Drawing Sheets

Specification includes a Sequence Listing.

Related U.S. Application Data continuation of application No. 14/586,865, filed on Dec. 30, 2014, which is a continuation-in-part of application No. 14/585,078, filed on Dec. 29, 2014.

(60) Provisional application No. 61/944,961, filed on Feb. 26, 2014, provisional application No. 61/922,734, filed on Dec. 31, 2013.

(51) Int. Cl.

| | | |
|---|---|---|
| *G06F 11/00* | (2006.01) | |
| *E21B 49/08* | (2006.01) | |
| *C12Q 1/6888* | (2018.01) | |
| *G16B 10/00* | (2019.01) | |
| *G16B 20/00* | (2019.01) | |
| *G16B 40/00* | (2019.01) | |
| *G16B 45/00* | (2019.01) | |
| *E21B 43/00* | (2006.01) | |
| *C09K 8/582* | (2006.01) | |
| *C09K 8/62* | (2006.01) | |
| *E21B 47/11* | (2012.01) | |
| *C12Q 1/689* | (2018.01) | |
| *E21B 49/00* | (2006.01) | |
| *G01V 9/00* | (2006.01) | |
| *C12Q 1/6874* | (2018.01) | |
| *E21B 43/26* | (2006.01) | |
| *E21B 43/267* | (2006.01) | |
| *E21B 21/06* | (2006.01) | |

(52) U.S. Cl.
CPC ......... *C12Q 1/6874* (2013.01); *C12Q 1/6888* (2013.01); *E21B 43/00* (2013.01); *E21B 47/11* (2020.05); *E21B 49/00* (2013.01); *E21B 49/086* (2013.01); *G01V 9/00* (2013.01); *G16B 10/00* (2019.02); *G16B 20/00* (2019.02); *G16B 40/00* (2019.02); *G16B 45/00* (2019.02); *C12Q 2600/156* (2013.01); *E21B 21/065* (2013.01); *E21B 43/26* (2013.01); *E21B 43/267* (2013.01); *E21B 49/003* (2013.01); *E21B 49/0875* (2020.05)

(58) Field of Classification Search
CPC ............ E21B 2049/085; C12Q 1/6874; C12Q 1/6888; G06F 19/24; G06F 19/26
See application file for complete search history.

(56) References Cited

U.S. PATENT DOCUMENTS

| | | | |
|---|---|---|---|
| 9,771,795 B2 | 9/2017 | Knight et al. | |
| 2001/0045279 A1 | 11/2001 | Converse et al. | |
| 2006/0154306 A1 | 7/2006 | Kotlar et al. | |
| 2008/0082469 A1 | 4/2008 | Wilkinson et al. | |
| 2010/0081184 A1* | 4/2010 | Downey | G16C 10/00 435/167 |
| 2010/0216219 A1 | 8/2010 | Hendrickson et al. | |
| 2011/0067856 A1 | 3/2011 | Kohr | |
| 2011/0250582 A1 | 10/2011 | Gates et al. | |
| 2011/0308790 A1* | 12/2011 | Strapoc | C09K 8/582 166/250.01 |
| 2012/0165215 A1 | 6/2012 | Andersen et al. | |
| 2012/0214713 A1 | 8/2012 | Mu et al. | |
| 2012/0252775 A1 | 10/2012 | Finegold | |
| 2012/0253770 A1 | 10/2012 | Stern et al. | |
| 2012/0308988 A1* | 12/2012 | Discenzo | C12M 41/36 435/3 |
| 2012/0310614 A1* | 12/2012 | Beattie | E21B 43/16 703/10 |
| 2013/0121968 A1 | 5/2013 | Quay | |
| 2014/0288853 A1 | 9/2014 | Dreyfus et al. | |
| 2014/0378319 A1 | 12/2014 | Regberg et al. | |
| 2015/0053407 A1 | 2/2015 | Voordouw et al. | |
| 2015/0284810 A1 | 10/2015 | Knight et al. | |
| 2015/0284811 A1 | 10/2015 | Knight et al. | |
| 2016/0011203 A1* | 1/2016 | Martin | G01N 33/6893 562/567 |
| 2016/0232311 A1* | 8/2016 | Segal | G16H 20/60 |
| 2016/0283651 A1 | 9/2016 | Knight et al. | |
| 2016/0290132 A1 | 10/2016 | Knight et al. | |
| 2017/0139078 A1 | 5/2017 | Knight et al. | |

FOREIGN PATENT DOCUMENTS

| | | |
|---|---|---|
| WO | WO-2015103332 A2 | 7/2015 |
| WO | WO-2015103332 A3 | 7/2015 |

OTHER PUBLICATIONS

"U.S. Appl. No. 14/585,078, Examiner Interview Summary dated Aug. 23, 2018", 3 pgs.

"U.S. Appl. No. 14/585,078, Final Office Action dated Jul. 27, 2018", 16.

"U.S. Appl. No. 14/585,078, Final Office Action dated Aug. 7, 2019", 17 pgs.

"U.S. Appl. No. 14/585,078, Non Final Office Action dated Feb. 1, 2019", 16 pgs.

"U.S. Appl. No. 14/585,078, Response filed Apr. 16, 2018 to Non Final Office Action dated Dec. 15, 2017", 34 pgs.

"U.S. Appl. No. 14/585,078, Response filed Apr. 26, 2019 to Non Final Office Action dated Feb. 1, 2019", 14 pgs.

"U.S. Appl. No. 14/585,078, Response filed Sep. 26, 2018 to Final Office Action dated Jul. 27, 2018", 26 pgs.

"U.S. Appl. No. 14/585,078, Supplemental Preliminary Amendment filed Dec. 13, 2018", 9 pgs.

"U.S. Appl. No. 14/586,865, Final Office Action dated Jun. 28, 2019", 15 pgs.

"U.S. Appl. No. 14/586,865, Final Office Action dated Aug. 10, 2018", 15 pgs.

"U.S. Appl. No. 14/586,865, Non Final Office Action dated Dec. 21, 2018", 15 pgs.

"U.S. Appl. No. 14/586,865, Response filed Apr. 16, 2018 to Non Final Office Action dated Dec. 15, 2017", 32 pgs.

"U.S. Appl. No. 14/586,865, Response filed Nov. 13, 2018 to Final Office Action dated Aug. 10, 2018", 11 pgs.

"U.S. Appl. No. 14/586,865, Response filed Sep. 30, 2019 to Final Office Action dated Jun. 28, 2019", 18 pgs.

"U.S. Appl. No. 15/087,497, Examiner Interview Summary dated Aug. 10, 2018", 3 pgs.

"U.S. Appl. No. 15/087,497, Final Office Action dated Aug. 22, 2019", 17 pgs.

"U.S. Appl. No. 15/087,497, Non Final Office Action dated Dec. 14, 2018", 13 pgs.

"U.S. Appl. No. 15/087,497, Response filed Sep. 5, 2018 to Restriction Requirement dated Jul. 5, 2018.pdf", 8 pgs.

"U.S. Appl. No. 15/087,497, Response filed May 9, 2019 to Non Final Office Action dated Dec. 14, 2018", 11 pgs.

"U.S. Appl. No. 15/087,497, Restriction Requirement dated Jul. 5, 2018", 8 pgs.

"U.S. Appl. No. 15/087,552, Examiner Interview Summary dated Dec. 29, 2016", 6 pgs.

"U.S. Appl. No. 15/087,552, Supplemental Preliminary Amendment filed Jun. 20, 2016", 4 pgs.

"U.S. Appl. No. 15/340,419, Non Final Office Action dated Jun. 27, 2019", 16 pgs.

"U.S. Appl. No. 15/340,419, Response filed Mar. 25, 2019 to Restriction Requirement dated Jan. 25, 2019", 6 pgs.

"U.S. Appl. No. 15/340,419, Response filed Sep. 27, 2019 to Non-Final Office Action dated Jun. 27, 2019", 18 pgs.

"U.S. Appl. No. 15/340,419, Restriction Requirement dated Jan. 25, 2019", 8 pgs.

"U.S. Appl. No. 15/586,865, Response filed Mar. 21, 2019 to Non Final Office Action dated Dec. 21, 2018", 12 pgs.

(56) References Cited

OTHER PUBLICATIONS

"European Application Serial No. 14876039.0, Extended European Search Report dated Jan. 10, 2018", 12 pgs.

"European Application Serial No. 14876039.0, Response filed Sep. 20, 2019 to Invitation pursuant to Rule 137(4) EPC and Article 94(3) EPC mailed May 3, 2019", 28 pgs.

"European Application Serial No. 14876039.0, Response filed to Extended European Search Report dated Jan. 10, 2018", 34 pgs.

"International Application Serial No. PCT/US2014/072607, Response filed Oct. 30, 2015 to Written Opinion dated May 15, 2015", 51 pgs.

Magot, et al., "Microbiology of petroleum reservoirs", Antonie van Leeuwenhoek 77, (2000), 103-116 pgs.

"U.S. Appl. No. 14/585,078, Preliminary Amendment filed Jun. 22, 2015", 181 pgs.

"U.S. Appl. No. 14/585,078, Restriction Requirement dated Jun. 30, 2017", 10 pgs.

"U.S. Appl. No. 14/586,865, Preliminary Amendment filed Jun. 23, 2015", 333 pgs.

"U.S. Appl. No. 14/586,865, Restriction Requirement dated Jun. 29, 2017", 9 pgs.

"U.S. Appl. No. 15/087,497, Preliminary Amendment filed Apr. 26, 2016", 6 pgs.

"U.S. Appl. No. 15/087,552, Advisory Action dated Apr. 21, 2017", 3 pgs.

"U.S. Appl. No. 15/087,552, Examiner Interview Summary dated Apr. 19, 2017", 3 pgs.

"U.S. Appl. No. 15/087,552, Final Office Action dated Mar. 9, 2017", 18 pgs.

"U.S. Appl. No. 15/087,552, Non Final Office Action dated Oct. 31, 2016", 24 pgs.

"U.S. Appl. No. 15/087,552, Notice of Allowance dated Jun. 28, 2017", 14 pgs.

"U.S. Appl. No. 15/087,552, Response filed Jan. 26, 2017 to Non Final Office Action dated Oct. 31, 2016", 43 pgs.

"U.S. Appl. No. 15/087,552, Response filed Apr. 11, 2017 to Final Office Action dated Mar. 9, 2017", 12 pgs.

"International Application Serial No. PCT/US2014/072607, International Search Report dated May 15, 2015", 4 pgs.

"International Application Serial No. PCT/US2014/072607, International Preliminary Report on Patentability dated Jan. 8, 2016", 6 pgs.

"International Application Serial No. PCT/US2014/072607, International Preliminary Report on Patentability dated Jul. 14, 2016", 11 pgs.

"International Application Serial No. PCT/US2014/072607, Invitation to Pay Add'l Fees and Partial Search Rpt dated Feb. 27, 2015", 2 pgs.

"International Application Serial No. PCT/US2014/072607, Written Opinion dated May 15, 2015", 7 pgs.

"International Application Serial No. PCT/US2014/072880, International Preliminary Report on Patentability dated Jul. 14, 2016", 11 pgs.

"International Application Serial No. PCT/US2014/072880, International Search Report dated Jul. 2, 2015", 5 pgs.

"International Application Serial No. PCT/US2014/072880, Written Opinion dated Jul. 2, 2015", 11 pgs.

Chikere, et al., "Monitoring of microbial hydrocarbon remediation in the soil", 2011.

Rshedi, Hamid, et al., "Chapter 3: Microbial Enhanced Oil Recovery", Introduction to Enhanced Oil Recovery (EOR) Processes and Bioremediation of Oil-Contaminated Sites [Online], Retrieved from the Internet: <URL: http://www.intechopen.com/books/introduction-to-enhanced-oil-recovery-eor-processes-and-bioremediation-of-oi, CC BY 3.0 license, (May 23, 2012), 73-88.

Soh, Jung, et al., "Phoenix 2: A locally installable large-scale 16S rRNA gene sequence analysis pipeline with Web interface", Journal of Biotechnology 167(4), (Sep. 20, 2013), 393-403.

Wooley, "A Primer on Metagenomics", (2010), 13 pgs.

"U.S. Appl. No. 14/585,078, Non Final Office Action dated Dec. 15, 2017", 24 pgs.

"U.S. Appl. No. 14/586,865, Non Final Office Action dated Dec. 15, 2017", 23 pgs.

Blieck, et al., "Applied and Environmental", Microbiology vol. 73, No. 3, (Feb. 2007).

"U.S. Appl. No. 14/585,078, Response filed Nov. 7, 2019 to Final Office Action dated Aug. 7, 2019", 18 pgs.

"U.S. Appl. No. 15/087,497, Advisory Action dated Dec. 4, 2019", 3 pgs.

"U.S. Appl. No. 15/087,497, Response filed Nov. 22, 2019 to Final Office Action dated Aug. 22, 2019", 18 pgs.

"U.S. Appl. No. 15/340,419, Final Office Action dated Jan. 10, 2020", 18 pgs.

"European Application Serial No. 14876039.0, Communication Pursuant to Article 94(3) EPC dated Feb. 6, 2020", 6 pgs.

"U.S. Appl. No. 15/340,419, Response filed Apr. 10, 2020 to Final Office Action dated Jan. 10, 2020", 21 pgs.

\* cited by examiner

|  | IT2 | HI3 | MD2 | CA1 | PE5 | CO1 | DF3 | PE1 | SP2 | CO3 | SA2 | CM1 |
|---|---|---|---|---|---|---|---|---|---|---|---|---|
| IT2 | 0.000 | 0.726 | 0.840 | 0.758 | 0.771 | 0.702 | 0.703 | 0.758 | 0.734 | 0.729 | 0.779 | 0.779 |
| HI3 | 0.726 | 0.000 | 0.814 | 0.705 | 0.845 | 0.742 | 0.780 | 0.840 | 0.794 | 0.735 | 0.749 | 0.727 |
| MD2 | 0.840 | 0.814 | 0.000 | 0.747 | 0.888 | 0.797 | 0.868 | 0.882 | 0.869 | 0.763 | 0.735 | 0.809 |
| CA1 | 0.758 | 0.705 | 0.747 | 0.000 | 0.864 | 0.709 | 0.829 | 0.858 | 0.812 | 0.861 | 0.858 | 0.703 |
| PE5 | 0.771 | 0.845 | 0.888 | 0.864 | 0.000 | 0.846 | 0.888 | 0.636 | 0.738 | 0.813 | 0.865 | 0.868 |
| CO1 | 0.702 | 0.742 | 0.797 | 0.709 | 0.846 | 0.000 | 0.784 | 0.839 | 0.772 | 0.707 | 0.756 | 0.781 |
| DF3 | 0.703 | 0.780 | 0.868 | 0.829 | 0.888 | 0.784 | 0.000 | 0.673 | 0.891 | 0.788 | 0.834 | 0.834 |
| PE1 | 0.758 | 0.840 | 0.882 | 0.858 | 0.636 | 0.839 | 0.673 | 0.000 | 0.717 | 0.824 | 0.860 | 0.858 |
| SP2 | 0.734 | 0.794 | 0.869 | 0.812 | 0.738 | 0.772 | 0.891 | 0.717 | 0.000 | 0.785 | 0.837 | 0.829 |
| CO3 | 0.729 | 0.735 | 0.763 | 0.861 | 0.813 | 0.707 | 0.788 | 0.824 | 0.785 | 0.000 | 0.703 | 0.742 |
| SA2 | 0.779 | 0.749 | 0.735 | 0.858 | 0.865 | 0.756 | 0.834 | 0.860 | 0.837 | 0.703 | 0.000 | 0.705 |
| CM1 | 0.779 | 0.727 | 0.809 | 0.703 | 0.868 | 0.781 | 0.834 | 0.858 | 0.829 | 0.742 | 0.705 | 0.000 |

FIG. 9

SEQUENCE LISTING

```
<160> NUMBER OF SEQ ID NOS: 65

<210> SEQ ID NO 1
<211> LENGTH: 60
<212> TYPE: DNA
<213> ORGANISM: Artificial Sequence
<220> FEATURE:
<223> OTHER INFORMATION: A synthetic primer

<400> SEQUENCE: 1
aatgatacgg cgaccaccga gatctacact atggtaattg tgtgccagcm gccgcggtaa      60

<210> SEQ ID NO 2
<211> LENGTH: 68
<212> TYPE: DNA
<213> ORGANISM: Artificial Sequence
<220> FEATURE:
<223> OTHER INFORMATION: A synthetic primer
<220> FEATURE:
<221> NAME/KEY: misc_feature
<222> LOCATION: (25)..(36)
<223> OTHER INFORMATION: n is a, c, g, or t

<400> SEQUENCE: 2
caagcagaag acggcatacg agatnnnnnn nnnnnnagtc agtcagccgg actachvggg      60 twtctaat                                                              68

<210> SEQ ID NO 3
<211> LENGTH: 31
<212> TYPE: DNA
<213> ORGANISM: Artificial Sequence
<220> FEATURE:
```

```
<223> OTHER INFORMATION: A synthetic primer

<400> SEQUENCE: 3
tatggtaatt gtgtgccagc mgccgcggta a                              31

<210> SEQ ID NO 4
<211> LENGTH: 32
<212> TYPE: DNA
<213> ORGANISM: Artificial Sequence
<220> FEATURE:
<223> OTHER INFORMATION: A synthetic primer

<400> SEQUENCE: 4
agtcagtcag ccggactach vgggtwtcta at                             32

<210> SEQ ID NO 5
<211> LENGTH: 32
<212> TYPE: DNA
<213> ORGANISM: Artificial Sequence
<220> FEATURE:
<223> OTHER INFORMATION: A synthetic primer

<400> SEQUENCE: 5
attagawacc cbdgtagtcc ggctgactga ct                             32

<210> SEQ ID NO 6
<211> LENGTH: 41
<212> TYPE: DNA
<213> ORGANISM: Artificial Sequence
<220> FEATURE:
<223> OTHER INFORMATION: A synthetic primer

<400> SEQUENCE: 6
gccttgccag cccgctcagt cagagtttga tcctggctca g                   41

<210> SEQ ID NO 7
<211> LENGTH: 52
<212> TYPE: DNA
<213> ORGANISM: Artificial Sequence
<220> FEATURE:
<223> OTHER INFORMATION: A synthetic primer
<220> FEATURE:
<221> NAME/KEY: misc_feature
<222> LOCATION: (20)..(31)
<223> OTHER INFORMATION: n is a, c, g, or t

<400> SEQUENCE: 7
gcctccctcg cgccatcagn nnnnnnnnnn ncatgctgcc tcccgtagga gt       52

<210> SEQ ID NO 8
<211> LENGTH: 19
<212> TYPE: DNA
<213> ORGANISM: Artificial Sequence
<220> FEATURE:
<223> OTHER INFORMATION: A synthetic primer

<400> SEQUENCE: 8
gtgccagcmg ccgcggtaa                                            19

<210> SEQ ID NO 9
<211> LENGTH: 17
<212> TYPE: DNA
<213> ORGANISM: Artificial Sequence
<220> FEATURE:
<223> OTHER INFORMATION: A synthetic primer

<400> SEQUENCE: 9
```
gacgggcggt gwgtrca                                                    17

<210> SEQ ID NO 10
<211> LENGTH: 12
<212> TYPE: DNA
<213> ORGANISM: Artificial Sequence
<220> FEATURE:
<223> OTHER INFORMATION: A synthetic primer or barcode

<400> SEQUENCE: 10
acgtgccgta ga                                                         12

<210> SEQ ID NO 11
<211> LENGTH: 21
<212> TYPE: DNA
<213> ORGANISM: Artificial Sequence
<220> FEATURE:
<223> OTHER INFORMATION: A synthetic primer or barcode

<400> SEQUENCE: 11
catgctgcct cccgtaggag t                                               21

<210> SEQ ID NO 12
<211> LENGTH: 12
<212> TYPE: DNA
<213> ORGANISM: Artificial Sequence
<220> FEATURE:
<223> OTHER INFORMATION: A synthetic primer or barcode

<400> SEQUENCE: 12
acgctatctg ga                                                         12

<210> SEQ ID NO 13
<211> LENGTH: 21
<212> TYPE: DNA
<213> ORGANISM: Artificial Sequence
<220> FEATURE:
<223> OTHER INFORMATION: A synthetic primer or barcode

<400> SEQUENCE: 13
catgctgcct cccgtaggag t                                               21

<210> SEQ ID NO 14
<211> LENGTH: 12
<212> TYPE: DNA
<213> ORGANISM: Artificial Sequence
<220> FEATURE:
<223> OTHER INFORMATION: A synthetic primer or barcode

<400> SEQUENCE: 14
actcgattcg at                                                         12

<210> SEQ ID NO 15
<211> LENGTH: 21
<212> TYPE: DNA
<213> ORGANISM: Artificial Sequence
<220> FEATURE:
<223> OTHER INFORMATION: A synthetic primer or barcode

<400> SEQUENCE: 15
catgctgcct cccgtaggag t                                               21

<210> SEQ ID NO 16
<211> LENGTH: 12
<212> TYPE: DNA

```
<213> ORGANISM: Artificial Sequence
<220> FEATURE:
<223> OTHER INFORMATION: A synthetic primer or barcode

<400> SEQUENCE: 16
acacgagcca ca                                                    12

<210> SEQ ID NO 17
<211> LENGTH: 21
<212> TYPE: DNA
<213> ORGANISM: Artificial Sequence
<220> FEATURE:
<223> OTHER INFORMATION: A synthetic primer or barcode

<400> SEQUENCE: 17
catgctgcct cccgtaggag t                                          21

<210> SEQ ID NO 18
<211> LENGTH: 12
<212> TYPE: DNA
<213> ORGANISM: Artificial Sequence
<220> FEATURE:
<223> OTHER INFORMATION: A synthetic primer or barcode

<400> SEQUENCE: 18
agactgcgta ct                                                    12

<210> SEQ ID NO 19
<211> LENGTH: 21
<212> TYPE: DNA
<213> ORGANISM: Artificial Sequence
<220> FEATURE:
<223> OTHER INFORMATION: A synthetic primer or barcode

<400> SEQUENCE: 19
catgctgcct cccgtaggag t                                          21

<210> SEQ ID NO 20
<211> LENGTH: 12
<212> TYPE: DNA
<213> ORGANISM: Artificial Sequence
<220> FEATURE:
<223> OTHER INFORMATION: A synthetic primer or barcode

<400> SEQUENCE: 20
acatgatcgt tc                                                    12

<210> SEQ ID NO 21
<211> LENGTH: 21
<212> TYPE: DNA
<213> ORGANISM: Artificial Sequence
<220> FEATURE:
<223> OTHER INFORMATION: A synthetic primer or barcode

<400> SEQUENCE: 21
catgctgcct cccgtaggag t                                          21

<210> SEQ ID NO 22
<211> LENGTH: 12
<212> TYPE: DNA
<213> ORGANISM: Artificial Sequence
<220> FEATURE:
<223> OTHER INFORMATION: A synthetic primer or barcode

<400> SEQUENCE: 22
accgcagagt ca                                                    12
```

```
<210> SEQ ID NO 23
<211> LENGTH: 21
<212> TYPE: DNA
<213> ORGANISM: Artificial Sequence
<220> FEATURE:
<223> OTHER INFORMATION: A synthetic primer or barcode

<400> SEQUENCE: 23
catgctgcct cccgtaggag t                                              21

<210> SEQ ID NO 24
<211> LENGTH: 12
<212> TYPE: DNA
<213> ORGANISM: Artificial Sequence
<220> FEATURE:
<223> OTHER INFORMATION: A synthetic primer or barcode

<400> SEQUENCE: 24
acttgtagca gc                                                        12

<210> SEQ ID NO 25
<211> LENGTH: 21
<212> TYPE: DNA
<213> ORGANISM: Artificial Sequence
<220> FEATURE:
<223> OTHER INFORMATION: A synthetic primer or barcode

<400> SEQUENCE: 25
catgctgcct cccgtaggag t                                              21

<210> SEQ ID NO 26
<211> LENGTH: 12
<212> TYPE: DNA
<213> ORGANISM: Artificial Sequence
<220> FEATURE:
<223> OTHER INFORMATION: A synthetic primer or barcode

<400> SEQUENCE: 26
agcgctgatg tg                                                        12

<210> SEQ ID NO 27
<211> LENGTH: 21
<212> TYPE: DNA
<213> ORGANISM: Artificial Sequence
<220> FEATURE:
<223> OTHER INFORMATION: A synthetic primer or barcode

<400> SEQUENCE: 27
catgctgcct cccgtaggag t                                              21

<210> SEQ ID NO 28
<211> LENGTH: 12
<212> TYPE: DNA
<213> ORGANISM: Artificial Sequence
<220> FEATURE:
<223> OTHER INFORMATION: A synthetic primer or barcode

<400> SEQUENCE: 28
acattcagcg ca                                                        12

<210> SEQ ID NO 29
<211> LENGTH: 21
<212> TYPE: DNA
<213> ORGANISM: Artificial Sequence
<220> FEATURE:
```

<223> OTHER INFORMATION: A synthetic primer or barcode

<400> SEQUENCE: 29
catgctgcct cccgtaggag t                                             21

<210> SEQ ID NO 30
<211> LENGTH: 12
<212> TYPE: DNA
<213> ORGANISM: Artificial Sequence
<220> FEATURE:
<223> OTHER INFORMATION: A synthetic primer or barcode

<400> SEQUENCE: 30
agatcggctc ga                                                       12

<210> SEQ ID NO 31
<211> LENGTH: 21
<212> TYPE: DNA
<213> ORGANISM: Artificial Sequence
<220> FEATURE:
<223> OTHER INFORMATION: A synthetic primer or barcode

<400> SEQUENCE: 31
catgctgcct cccgtaggag t                                             21

<210> SEQ ID NO 32
<211> LENGTH: 12
<212> TYPE: DNA
<213> ORGANISM: Artificial Sequence
<220> FEATURE:
<223> OTHER INFORMATION: A synthetic primer or barcode

<400> SEQUENCE: 32
acatcactta gc                                                       12

<210> SEQ ID NO 33
<211> LENGTH: 21
<212> TYPE: DNA
<213> ORGANISM: Artificial Sequence
<220> FEATURE:
<223> OTHER INFORMATION: A synthetic primer or barcode

<400> SEQUENCE: 33
catgctgcct cccgtaggag t                                             21

<210> SEQ ID NO 34
<211> LENGTH: 12
<212> TYPE: DNA
<213> ORGANISM: Artificial Sequence
<220> FEATURE:
<223> OTHER INFORMATION: A synthetic primer or barcode

<400> SEQUENCE: 34
actcacggta tg                                                       12

<210> SEQ ID NO 35
<211> LENGTH: 21
<212> TYPE: DNA
<213> ORGANISM: Artificial Sequence
<220> FEATURE:
<223> OTHER INFORMATION: A synthetic primer or barcode

<400> SEQUENCE: 35
catgctgcct cccgtaggag t                                             21

```
<210> SEQ ID NO 36
<211> LENGTH: 12
<212> TYPE: DNA
<213> ORGANISM: Artificial Sequence
<220> FEATURE:
<223> OTHER INFORMATION: A synthetic primer or barcode

<400> SEQUENCE: 36
agctatccac ga                                                          12

<210> SEQ ID NO 37
<211> LENGTH: 21
<212> TYPE: DNA
<213> ORGANISM: Artificial Sequence
<220> FEATURE:
<223> OTHER INFORMATION: A synthetic primer or barcode

<400> SEQUENCE: 37
catgctgcct cccgtaggag t                                                21

<210> SEQ ID NO 38
<211> LENGTH: 12
<212> TYPE: DNA
<213> ORGANISM: Artificial Sequence
<220> FEATURE:
<223> OTHER INFORMATION: A synthetic primer or barcode

<400> SEQUENCE: 38
accacataca tc                                                          12

<210> SEQ ID NO 39
<211> LENGTH: 21
<212> TYPE: DNA
<213> ORGANISM: Artificial Sequence
<220> FEATURE:
<223> OTHER INFORMATION: A synthetic primer or barcode

<400> SEQUENCE: 39
catgctgcct cccgtaggag t                                                21

<210> SEQ ID NO 40
<211> LENGTH: 12
<212> TYPE: DNA
<213> ORGANISM: Artificial Sequence
<220> FEATURE:
<223> OTHER INFORMATION: A synthetic primer or barcode

<400> SEQUENCE: 40
aggtgtgatc gc                                                          12

<210> SEQ ID NO 41
<211> LENGTH: 21
<212> TYPE: DNA
<213> ORGANISM: Artificial Sequence
<220> FEATURE:
<223> OTHER INFORMATION: A synthetic primer or barcode

<400> SEQUENCE: 41
catgctgcct cccgtaggag t                                                21

<210> SEQ ID NO 42
<211> LENGTH: 12
<212> TYPE: DNA
<213> ORGANISM: Artificial Sequence
<220> FEATURE:
<223> OTHER INFORMATION: A synthetic primer or barcode
```

<400> SEQUENCE: 42
acgtctgtag ca                                                          12

<210> SEQ ID NO 43
<211> LENGTH: 21
<212> TYPE: DNA
<213> ORGANISM: Artificial Sequence
<220> FEATURE:
<223> OTHER INFORMATION: A synthetic primer or barcode

<400> SEQUENCE: 43
catgctgcct cccgtaggag t                                                21

<210> SEQ ID NO 44
<211> LENGTH: 12
<212> TYPE: DNA
<213> ORGANISM: Artificial Sequence
<220> FEATURE:
<223> OTHER INFORMATION: A synthetic primer or barcode

<400> SEQUENCE: 44
agagtcctga gc                                                          12

<210> SEQ ID NO 45
<211> LENGTH: 21
<212> TYPE: DNA
<213> ORGANISM: Artificial Sequence
<220> FEATURE:
<223> OTHER INFORMATION: A synthetic primer or barcode

<400> SEQUENCE: 45
catgctgcct cccgtaggag t                                                21

<210> SEQ ID NO 46
<211> LENGTH: 12
<212> TYPE: DNA
<213> ORGANISM: Artificial Sequence
<220> FEATURE:
<223> OTHER INFORMATION: A synthetic primer or barcode

<400> SEQUENCE: 46
aagagatgtc ga                                                          12

<210> SEQ ID NO 47
<211> LENGTH: 21
<212> TYPE: DNA
<213> ORGANISM: Artificial Sequence
<220> FEATURE:
<223> OTHER INFORMATION: A synthetic primer or barcode

<400> SEQUENCE: 47
catgctgcct cccgtaggag t                                                21

<210> SEQ ID NO 48
<211> LENGTH: 12
<212> TYPE: DNA
<213> ORGANISM: Artificial Sequence
<220> FEATURE:
<223> OTHER INFORMATION: A synthetic primer or barcode

<400> SEQUENCE: 48
acactagatc cg                                                          12

<210> SEQ ID NO 49
<211> LENGTH: 21

```
<212> TYPE: DNA
<213> ORGANISM: Artificial Sequence
<220> FEATURE:
<223> OTHER INFORMATION: A synthetic primer or barcode

<400> SEQUENCE: 49
catgctgcct cccgtaggag t                                              21

<210> SEQ ID NO 50
<211> LENGTH: 12
<212> TYPE: DNA
<213> ORGANISM: Artificial Sequence
<220> FEATURE:
<223> OTHER INFORMATION: A synthetic primer or barcode

<400> SEQUENCE: 50
aggacgcact gt                                                        12

<210> SEQ ID NO 51
<211> LENGTH: 21
<212> TYPE: DNA
<213> ORGANISM: Artificial Sequence
<220> FEATURE:
<223> OTHER INFORMATION: A synthetic primer or barcode

<400> SEQUENCE: 51
catgctgcct cccgtaggag t                                              21

<210> SEQ ID NO 52
<211> LENGTH: 12
<212> TYPE: DNA
<213> ORGANISM: Artificial Sequence
<220> FEATURE:
<223> OTHER INFORMATION: A synthetic primer or barcode

<400> SEQUENCE: 52
agagagcaag tg                                                        12

<210> SEQ ID NO 53
<211> LENGTH: 21
<212> TYPE: DNA
<213> ORGANISM: Artificial Sequence
<220> FEATURE:
<223> OTHER INFORMATION: A synthetic primer or barcode

<400> SEQUENCE: 53
catgctgcct cccgtaggag t                                              21

<210> SEQ ID NO 54
<211> LENGTH: 12
<212> TYPE: DNA
<213> ORGANISM: Artificial Sequence
<220> FEATURE:
<223> OTHER INFORMATION: A synthetic primer or barcode

<400> SEQUENCE: 54
acgcgatact gg                                                        12

<210> SEQ ID NO 55
<211> LENGTH: 21
<212> TYPE: DNA
<213> ORGANISM: Artificial Sequence
<220> FEATURE:
<223> OTHER INFORMATION: A synthetic primer or barcode

<400> SEQUENCE: 55
```

```
catgctgcct cccgtaggag t                                              21

<210> SEQ ID NO 56
<211> LENGTH: 12
<212> TYPE: DNA
<213> ORGANISM: Artificial Sequence
<220> FEATURE:
<223> OTHER INFORMATION: A synthetic primer or barcode

<400> SEQUENCE: 56
agagcaagag ca                                                        12

<210> SEQ ID NO 57
<211> LENGTH: 21
<212> TYPE: DNA
<213> ORGANISM: Artificial Sequence
<220> FEATURE:
<223> OTHER INFORMATION: A synthetic primer or barcode

<400> SEQUENCE: 57
catgctgcct cccgtaggag t                                              21

<210> SEQ ID NO 58
<211> LENGTH: 12
<212> TYPE: DNA
<213> ORGANISM: Artificial Sequence
<220> FEATURE:
<223> OTHER INFORMATION: A synthetic primer or barcode

<400> SEQUENCE: 58
aatcagtctc gt                                                        12

<210> SEQ ID NO 59
<211> LENGTH: 21
<212> TYPE: DNA
<213> ORGANISM: Artificial Sequence
<220> FEATURE:
<223> OTHER INFORMATION: A synthetic primer or barcode

<400> SEQUENCE: 59
catgctgcct cccgtaggag t                                              21

<210> SEQ ID NO 60
<211> LENGTH: 12
<212> TYPE: DNA
<213> ORGANISM: Artificial Sequence
<220> FEATURE:
<223> OTHER INFORMATION: A synthetic primer or barcode

<400> SEQUENCE: 60
agcttgacag ct                                                        12

<210> SEQ ID NO 61
<211> LENGTH: 21
<212> TYPE: DNA
<213> ORGANISM: Artificial Sequence
<220> FEATURE:
<223> OTHER INFORMATION: A synthetic primer or barcode

<400> SEQUENCE: 61
catgctgcct cccgtaggag t                                              21

<210> SEQ ID NO 62
<211> LENGTH: 12
<212> TYPE: DNA
<213> ORGANISM: Artificial Sequence
```

```
<220> FEATURE:
<223> OTHER INFORMATION: A synthetic primer or barcode

<400> SEQUENCE: 62
actacagcct at                                                              12

<210> SEQ ID NO 63
<211> LENGTH: 21
<212> TYPE: DNA
<213> ORGANISM: Artificial Sequence
<220> FEATURE:
<223> OTHER INFORMATION: A synthetic primer or barcode

<400> SEQUENCE: 63
catgctgcct cccgtaggag t                                                    21

<210> SEQ ID NO 64
<211> LENGTH: 12
<212> TYPE: DNA
<213> ORGANISM: Artificial Sequence
<220> FEATURE:
<223> OTHER INFORMATION: A synthetic primer or barcode

<400> SEQUENCE: 64
acagtgcttc at                                                              12

<210> SEQ ID NO 65
<211> LENGTH: 21
<212> TYPE: DNA
<213> ORGANISM: Artificial Sequence
<220> FEATURE:
<223> OTHER INFORMATION: A synthetic primer or barcode

<400> SEQUENCE: 65
catgctgcct cccgtaggag t                                                    21
```

MICROBIOME BASED SYSTEMS, APPARATUS AND METHODS FOR THE EXPLORATION AND PRODUCTION OF HYDROCARBONS

This application is a continuation of U.S. application Ser. No. 15/087,552, filed Mar. 31, 2016, which is a continuation of U.S. application Ser. No. 14/586,865, filed Dec. 30, 2014, which claims the benefit of U.S. Provisional Application No. 61/922,734, filed Dec. 31, 2013, and U.S. Provisional Application No. 61/944,961, filed Feb. 26, 2014, and is a continuation-in-part of U.S. application Ser. No. 14/585,078, filed Dec. 29, 2014, which claims the benefit of U.S. Provisional Application No. 61/922,734, filed Dec. 31, 2013, and U.S. Provisional Application No. 61/944,961, filed Feb. 26, 2014, each of which is incorporated herein by reference in its entirety.

This invention was made with Government support under SBIR award number 1416179 by the National Science Foundation. The Government has certain rights in this invention.

BACKGROUND OF THE INVENTION

Field of the Invention

The present inventions relate to novel and unique apparatus, systems, and methods for monitoring, analyzing, planning and controlling the exploration and production of natural resources, including energy resources, such, as geothermal and hydrocarbons. There has been a continuous need for a better understanding of the factors and conditions that influence and relate to the exploration and production of hydrocarbons, such as natural gas and oil. Thus, great efforts have been made in areas such as geologic evaluation, seismic, pressure sensing, radiation, sonic, logging while drilling, ("LWD"), measuring while drilling ("MWD"), and combinations thereof MWD/LWD, which efforts have almost exclusively focused on traditional sensing, analysis and control methodologies.

The art of exploring and producing hydrocarbons, however, has largely ignored the microbial and genetic information that is present in, or associated with, hydrocarbon exploration and production including such information that is associated with a borehole, borehole fluids, borehole cuttings, a formation, a reservoir, a pay zone and an oil field. While efforts have been made to evaluate a particular microbial present in an oil or natural gas well, these efforts have largely focused on identification of a particular microbe, e.g., through DNA analysis, for the purposes of eliminating undesirable microbes and increasing beneficial ones. Further, analysis and work has taken place to genetically engineer microbes to meet, or fulfill, a particular function in hydrocarbon production and clean up. However, it is believed that prior to the present inventions, the use of microbial and genetic information, has never been used, and was not able to be used, for the purposes of monitoring, analyzing, planning and controlling the exploration and production of hydrocarbons.

Thus, and in general, the present inventions provide apparatus, systems and methods for determining and characterizing the microbiome associated with hydrocarbon exploration and production, obtaining such microbiome information, converting such information into a form that is useful in the exploration and production of hydrocarbons, and using such information in the exploration and production of hydrocarbons, and combinations and variations of these. In view of the ubiquitous nature of genetic material and microorganisms, the present inventions provide, among other things, the ability to control, enhance, plan, monitor, and predict performance of, hydrocarbon exploration and production activities.

The terms microbiome, microbiome information, microbiome data, and similar such terms are used herein in the broadest possible sense, unless expressly stated otherwise, and would include: a census of currently present microorganisms, both living and nonliving, which may have been present months, years, millennia or longer ("the microbiota"); a census of components of the microbiome other than bacteria and archaea, e.g., viruses and microbial eukaryotes; population studies and characterizations of microorganisms, genetic material, and biologic material; a census of any detectable biological material; and information that is derived or ascertained from genetic material, biomolecular makeup, fragments of genetic material, DNA, RNA, protein, carbohydrate, metabolite profile, fragment of biological materials and combinations and variations of these.

As used herein, the terms historic microbiome information and historic microbiome data are to be given their broadest possible meaning, unless specified otherwise, and includes publicly available databases, e.g., the Earth Microbiome Project, the Human Microbiome Project, American Gut, GreenGenes, the Ribosomal Database Project, the International Nucleotide Sequence Database Collaboration (INSDC), American Gut, etc., regarding the microbiome. It would also include databases that are based upon real-time microbiome data and derived microbiome data. These databases may be cloud-based, locally-based, or hosted on remote systems other than cloud-based systems.

As used herein, the terms real-time microbiome information and real-time microbiome data are to be given their broadest possible meaning, unless specified otherwise, and includes microbiome information that is collected or obtained at a particular industrial setting during an industrial activity, which would include for example sampling and determining the microbiome present in a pipeline flow, in returns from drilling a borehole, in hydraulic fracturing fluid, agricultural runoff or soil samples taken during a planting or harvesting.

As used herein, the terms derived microbiome information and derived microbiome data are to be given their broadest possible meaning, unless specified otherwise, and includes any real-time, historic, and combinations of these, microbiome information that has been computationally linked or used to create a relationship such as for example evaluating the microbiome of hydraulic fracturing fluid before, during, and after hydraulic fracturing stages, evaluating the microbiome between planting and harvesting, and evaluating the historic microbiome of deep core samples with the microbiome of hydrocarbon product delivered from the well. Thus, derived microbiome information provides information about the industrial process setting or activity that may not be readily ascertained from non-derived information.

As used herein, the terms predictive microbiome information and predictive microbiome data are to be given their broadest possible meaning, unless specified otherwise, and includes information that is based upon combinations and computational links or processing of historic, predictive, real-time, and derived microbiome information, data, and combinations, variations and derivatives of these, which information predicts, forecasts, directs, or anticipates a future occurrence, event, state, or condition in the industrial setting, or allows interpretation of a current or past occurrence. Thus, by way of example, predictive microbiome information would include: a determination and comparison of real-time microbiome information and the derived microbiome information of an exploratory process to identify a hydrocarbon source; a comparison of real-time microbiome information collected during the advancement of a borehole to predict a perforation or hydraulic fracturing pattern; a determination and comparison of derived microbiome information and historic microbiome information of a chemical processing plant to identify an enhanced efficiency in the process; and, a comparison and analysis of historic microbiome data from, for example, core samples and derived microbiome information from well cutting returns to characterize a formation.

Real-time, derived, and predicted data may be collected and stored, and thus, become historic data for an ongoing or future process, setting, or application.

As used herein, unless specified otherwise, the terms "hydrocarbon exploration and production", "exploration and production activities", "E&P", and "E&P activities", and similar such terms are to be given their broadest possible meaning, and include surveying, geological analysis, well planning, reservoir planning, reservoir management, drilling a well, workover and completion activities, hydrocarbon production, flowing of hydrocarbons from a well, collection of hydrocarbons, secondary and tertiary recovery from a well, the management of flowing hydrocarbons from a well, and any other upstream activities.

As used herein, unless specified otherwise, the term "earth" should be given its broadest possible meaning, and includes, the ground, all natural materials, such as rocks, and artificial materials, such as concrete, that are or may be found in the ground.

As used herein, unless specified otherwise "offshore" and "offshore drilling activities" and similar such terms are used in their broadest sense and would include drilling activities on, or in, any body of water, whether fresh or salt water, whether manmade or naturally occurring, such as for example rivers, lakes, canals, inland seas, oceans, seas, such as the North Sea, bays and gulfs, such as the Gulf of Mexico. As used herein, unless specified otherwise the term "offshore drilling rig" is to be given its broadest possible meaning and would include fixed towers, tenders, platforms, barges, jack-ups, floating platforms, drill ships, dynamically positioned drill ships, semi-submersibles and dynamically positioned semi-submersibles. As used herein, unless specified otherwise the term "seafloor" is to be given its broadest possible meaning and would include any surface of the earth that lies under, or is at the bottom of, any body of water, whether fresh or salt water, whether manmade or naturally occurring.

As used herein, unless specified otherwise, the term "borehole" should be given it broadest possible meaning and includes any opening that is created in the earth that is substantially longer than it is wide, such as a well, a well bore, a well hole, a micro hole, a slimhole and other terms commonly used or known in the arts to define these types of narrow long passages. Wells would further include exploratory, production, abandoned, reentered, reworked, and injection wells. They would include both cased and uncased wells, and sections of those wells. Uncased wells, or section of wells, also are called open holes, or open hole sections. Boreholes may further have segments or sections that have different orientations, they may have straight sections and arcuate sections and combinations thereof. Thus, as used herein unless expressly provided otherwise, the "bottom" of a borehole, the "bottom surface" of the borehole and similar terms refer to the end of the borehole, i.e., that portion of the borehole furthest along the path of the borehole from the borehole's opening, the surface of the earth, or the borehole's beginning. The terms "side" and "wall" of a borehole should to be given their broadest possible meaning and include the longitudinal surfaces of the borehole, whether or not casing or a liner is present, as such, these terms would include the sides of an open borehole or the sides of the casing that has been positioned within a borehole. Boreholes may be made up of a single passage, multiple passages, connected passages, (e.g., branched configuration, fishboned configuration, or comb configuration), and combinations and variations thereof.

As used herein, unless specified otherwise, the term "advancing a borehole", "drilling a well", and similar such terms should be given their broadest possible meaning and include increasing the length of the borehole. Thus, by advancing a borehole, provided the orientation is not horizontal and is downward, e.g., less than 90°, the depth of the borehole may also be increased.

Boreholes are generally formed and advanced by using mechanical drilling equipment having a rotating drilling tool, e.g., a bit. For example, and in general, when creating a borehole in the earth, a drilling bit is extending to and into the earth and rotated to create a hole in the earth. To perform the drilling operation the bit must be forced against the material to be removed with a sufficient force to exceed the shear strength, compressive strength or combinations thereof, of that material. The material that is cut from the earth is generally known as cuttings, e.g., waste, which may be chips of rock, dust, rock fibers and other types of materials and structures that may be created by the bit's interactions with the earth. These cuttings are typically removed from the borehole by the use of fluids, which fluids can be liquids, foams or gases, or other materials know to the art.

The true vertical depth ("TVD") of a borehole is the distance from the top or surface of the borehole to the depth at which the bottom of the borehole is located, measured along a straight vertical line. The measured depth ("MD") of a borehole is the distance as measured along the actual path of the borehole from the top or surface to the bottom. As used herein unless specified otherwise the term depth of a borehole will refer to MD. In general, a point of reference may be used for the top of the borehole, such as the rotary table, drill floor, well head or initial opening or surface of the structure in which the borehole is placed.

As used herein, unless specified otherwise, the term "drill pipe" is to be given its broadest possible meaning and includes all forms of pipe used for drilling activities; and refers to a single section or piece of pipe. As used herein the terms "stand of drill pipe," "drill pipe stand," "stand of pipe," "stand" and similar type terms should be given their broadest possible meaning and include two, three or four sections of drill pipe that have been connected, e.g., joined together, typically by joints having threaded connections. As used herein the terms "drill string," "string," "string of drill pipe," string of pipe" and similar type terms should be given their broadest definition and would include a stand or stands joined together for the purpose of being employed in a borehole. Thus, a drill string could include many stands and many hundreds of sections of drill pipe.

As used herein, unless specified otherwise, the terms "blowout preventer," "BOP," and "BOP stack" should be given their broadest possible meanings, and include devices positioned at or near the borehole surface, e.g., the surface of the earth including dry land or the seafloor, which are used to contain or manage pressures or flows associated with a borehole and other combinations and assemblies of flow and pressure management devices to control borehole pressures, flows or both and, in particular, to control or manage emergency flow or pressure situations.

As used herein, unless specified otherwise, the terms "drill bit", "bit", "drilling bit" or similar such terms, should be given their broadest possible meaning and include all tools designed or intended to create a borehole in an object, a material, a work piece, a surface, the earth or a structure including structures within the earth, and would include bits used in the oil, gas and geothermal arts, such as fixed cutter and roller cone bits, as well as, other types of bits, such as, rotary shoe, drag-type, fishtail, adamantine, single and multi toothed, cone, reaming cone, reaming, self-cleaning, disc, three-cone, rolling cutter, crossroller, jet, core, impreg and hammer bits, and combinations and variations of the these.

As used herein, unless specified otherwise, the terms "workover," "completion" and "workover and completion" and similar such terms should be given their broadest possible meanings and would include activities that place at or near the completion of drilling a well, activities that take place at or near the commencement of production from the well, activities that take place on the well when the well is a producing or operating well, activities that take place to reopen or reenter an abandoned or plugged well or branch of a well, and would also include for example, perforating, cementing, acidizing, fracturing, pressure testing, the removal of well debris, removal of plugs, insertion or replacement of production tubing, forming windows in casing to drill or complete lateral or branch wellbores, cutting and milling operations in general, insertion of screens, stimulating, cleaning, testing, analyzing and other such activities.

As used herein, unless specified otherwise, the terms "formation," "reservoir," "pay zone," and similar terms, are to be given their broadest possible meanings and would include all locations, areas, and geological features within the earth that contain, may contain, or are believed to contain, hydrocarbons.

As used herein, unless specified otherwise, the terms "field," "oil field" and similar terms, are to be given their broadest possible meanings, and would include any area of land, sea floor, or water that is loosely or directly associated with a formation, and more particularly with a resource containing formation, thus, a field may have one or more exploratory and producing wells associated with it, a field may have one or more governmental body or private resource leases associated with it, and one or more field(s) may be directly associated with a resource containing formation.

Drilling and Completing Wells

In the production of natural resources from formations, reservoirs, deposits, or locations within the earth a well or borehole is drilled into the earth to the location where the natural resource is believed to be located. These natural resources may be a hydrocarbon reservoir, containing natural gas, crude oil and combinations of these; the natural resource may be fresh water; it may be a heat source for geothermal energy; or it may be some other natural resource that is located within the ground.

These resource-containing formations may be at or near the surface, at or near the sea floor, a few hundred feet, a few thousand feet, or tens of thousands of feet below the surface of the earth, including under the floor of a body of water, e.g., below the sea floor. In addition to being at various depths within the earth, these formations may cover areas of differing sizes, shapes and volumes.

Unfortunately, and generally, when a well is drilled into these formations the natural resources rarely flow into the well at rates, durations and amounts that are economically viable. This problem occurs for several reasons, some of which are understood, others of which are not as well understood, and some of which may not yet be known. These problems can relate to the viscosity of the natural resource, the porosity of the formation, the geology of the formation, the formation pressures, and the openings that place the resource recovery conduit, e.g., production tubing, in the well in fluid communication with the formation, to name a few.

Typically, and by way of general illustration, in drilling a well an initial borehole is made into the earth, e.g., surface of land or seabed, and then subsequent and smaller diameter boreholes are drilled to extend the overall depth of the borehole. Thus, as the overall borehole gets deeper its diameter becomes smaller; resulting in what can be envisioned as a telescoping assembly of holes with the largest diameter hole being at the top of the borehole closest to the surface of the earth.

Thus, by way of example, the starting phases of a subsea drill process may be explained in general as follows. Once the drilling rig is positioned on the surface of the water over the area where drilling is to take place, an initial borehole is made by drilling a 36" hole in the earth to a depth of about 200-300 ft. below the seafloor. A 30" casing is inserted into this initial borehole. This 30" casing may also be called a conductor. The 60" conductor may or may not be cemented into place. During this drilling operation a riser is generally not used and the cuttings from the borehole, e.g., the earth and other material removed from the borehole by the drilling activity are returned to the seafloor. Next, a 26" diameter borehole is drilled within the 30" casing, extending the depth of the borehole to about 1,000-1,500 ft. This drilling operation may also be conducted without using a riser. A 20" casing is then inserted into the 30" conductor and 26" borehole. This 20" casing is cemented into place. The 20" casing has a wellhead secured to it. (In other operations an additional smaller diameter borehole may be drilled, and a smaller diameter casing inserted into that borehole with the wellhead being secured to that smaller diameter casing.) A BOP is then secured to a riser and lowered by the riser to the sea floor; where the BOP is secured to the wellhead, From this point forward all drilling activity in the borehole takes place through the riser and the BOP.

For a land based drill process, the steps are similar, although the large diameter tubulars, 30"-20" are typically not used. Thus, and generally, there is a surface casing that is typically about 13⅜" diameter. This may extend from the surface, e.g., wellhead and BOP, to depths of tens of feet to hundreds of feet. One of the purposes of the surface casing is to meet environmental concerns in protecting ground water. The surface casing should have sufficiently large diameter to allow the drill string, product equipment such as ESPs and circulation mud to pass by. Below the casing one or more different diameter intermediate casings may be used. (It is understood that sections of a borehole may not be cased, which sections are referred to as open hole.) These can have diameters in the range of about 9" to about 7", although larger and smaller sizes may be used, and can extend to depths of thousands and tens of thousands of feet. Inside of the casing and extending from a pay zone, or production zone of the borehole up to and through the wellhead on the surface is the production tubing. There may be a single production tubing or multiple production tubings in a single borehole, with each of the production tubing endings being at different depths.

Typically, when completing a well, it is necessary to perform a perforation operation, and also in some instances perform a hydraulic fracturing, or fracing operation. In general, when a well has been drilled and casing, e.g., a metal pipe, is run to the prescribed depth, the casing is typically cemented in place by pumping cement down and into the annular space between the casing and the earth. The casing, among other things, prevents the hole from collapsing and fluids from flowing between permeable zones in the annulus. (In some situations only the metal casing is present, in others there may be two metal casing present one inside of the other, there may be more that two metal casing present each inside of the other, in still others the metal casing and cement are present, and in others there could be other configurations of metal, cement and metal; and in others there may be an open hole, e.g., no casing, liner or cement is present, at the location of interest in the borehole.) Thus, this casing forms a structural support for the well and a barrier to the earth.

While important for the structural integrity of the well, the casing and cement present a problem when they are in the production zone. Thus, in addition to holding back the earth, they also prevent the hydrocarbons from flowing into the well and from being recovered. Additionally, the formation itself may have been damaged by the drilling process, e.g., by the pressure from the drilling mud, and this damaged area of the formation may form an additional barrier to the flow of hydrocarbons into the well. Similarly, in most situations where casing is not needed in the production area, e.g., open hole, the formation itself is generally tight, and more typically can be very tight, and thus, will not permit the hydrocarbons to flow into the well. In some situations the formation pressure is large enough that the hydrocarbons readily flow into the well in an uncased, or open hole. Nevertheless, as formation pressure lessens a point will be reached where the formation itself shuts-off, or significantly reduces, the flow of hydrocarbons into the well. Also the low formation pressure could prevent fluid from flowing from the bottom of the borehole to the surface, requiring the use of artificial lift.

To overcome this problem of the flow of hydrocarbons into the well being blocked by the casing, cement and the formation itself, openings, e.g., perforations, are made in the well in the area of the pay zone. Generally, a perforation is a small, about ¼" to about 1" or 2" in diameter hole that extends through the casing, cement and damaged formation and goes into the formation. This hole creates a passage for the hydrocarbons to flow from the formation into the well. In a typical well a large number of these holes are made through the casing and into the formation in the pay zone.

Generally, in a perforating operation a perforating tool or gun is lowered into borehole to the location where the production zone or pay zone is located. The perforating gun is a long, typically round tool, that has a small enough diameter to fit into the casing or tubular and reach the area within the borehole where the production zone is believed to be. Once positioned in the production zone a series of explosive charges, e.g., shaped charges, are ignited. The hot gases and molten metal from the explosion cut a hole, i.e., the perf or perforation, through the casing and into the formation. These explosive-made perforations may only extend a few inches, e.g., 6" to 18" into the formation. In hard rock formations the explosive perforation device may only extend an inch or so, and may function poorly, if at all. Additionally, because these perforations are made with explosives they typically have damages areas, which include loose rock and perforation debris along the bottom of the hole, and a damaged zone extending annularly around the hole. Beyond the damaged zone is a virgin zone extending annularly around the damaged zone. The damaged zone, which typically encompasses the entire hole, generally, greatly reduces the permeability of the formation. This has been a long-standing and unsolved problem, among others, with the use of explosive perforations. The perforation holes are made to get through one group of obstructions to the flow of hydrocarbons into the well, e.g., the casing, and in doing so they create a new group of these obstructions, e.g., the damaged area encompassing the perforation holes.

The ability of, or ease with which, the natural resource can flow out of the formation and into the well or production tubing (into and out of, for example, in the case of engineered geothermal wells, and some advanced recovery methods for hydrocarbon wells) can generally be understood as the fluid communication between the well and the formation. As this fluid communication is increased several enhancements or benefits may be obtained: the volume or rate of flow (e.g., gals per minute) can increase; the distance within the formation out from the well where the natural resources will flow into the well can be increase (e.g., the volume and area of the formation that can be drained by a single well is increased and it will thus take less total wells to recover the resources from an entire field); the time period when the well is producing resources can be lengthened; the flow rate can be maintained at a higher rate for a longer period of time; and combinations of these and other efficiencies and benefits.

Fluid communication between the formation and the well can be greatly increased by the use of hydraulic fracturing techniques. The first uses of hydraulic fracturing date back to the late 1940s and early 1950s. In general, hydraulic fracturing treatments involve forcing fluids down the well and into the formation, the fluids enter the formation and crack open the rock, e.g., force the layers of rock to break apart or fracture. These fractures create channels or flow paths that may have cross sections of a few millimeters, to several millimeters, to several centimeters, and potentially larger. The fractures may also extend out from the well in all directions for a few feet, several feet and tens of feet or further. It should be remembered that no wellbore or branch of a wellbore is perfectly vertical or horizontal. The longitudinal axis of the well bore in the reservoir will most likely be on an angle to both the vertical and the horizontal directions. The borehole could be sloping up or down or on occasion be mostly horizontal. The section of the well bore located within the reservoir, i.e., the section of the formation containing the natural resources, can be called the pay zone. For example, in the recovery of shale gas and oil the wells are typically essentially horizontal in the reservoir.

Generally, in a hydraulic fracturing operation a mixture of typically a water based fluid with sand or other small particles, e.g., proppants, is forced into the well and out into the formation (if the well is perforated the fracturing fluid is forced out and through one or more of the perforations and into the formation). The fluids used to perform hydraulic fracture can range from very simple to multicomponent formulations, e.g., water, water containing gelling agents to increase the viscosity of the fracturing fluid. Additionally, these fluids, e.g., fracing fluids or fracturing fluids, typically carry with them propping agents (proppants). Proppants are small particles, e.g., grains of sand or other material, that are flowed into the fractures and hold open the fractures when the pressure of the fracturing fluid is reduced and the fluid is removed to allow the resource, e.g., hydrocarbons, to flow into the well. In this manner the proppants hold open the fractures, keeping the channels open so that the hydrocarbons can more readily flow into the well. Additionally, the fractures greatly increase the surface area from which the hydrocarbons can flow into the well. Proppants may not be needed, or generally may not be used when acids are used to create a frac and subsequent channel in a carbonate rich reservoir where the acids dissolve part or all of the rock leaving an opening for the formation fluids to flow to the wellbore.

Typical fluid volumes in a propped fracturing treatment of a formation in general can range from a few thousand to a few million gallons, Proppant volumes can be several thousand cubic feet, and can approach several hundred thousand cubic feet. For example, for a single well 3-5 million gallons of water may be used and pressures may be in the range of about 500 psi and greater, at least about 1,000 psi, about 5,000 psi to about 10,000 psi, as high as 15,000 psi and potentially higher. As the fracturing fluid and proppants are forced into the formation at high injection rate, the bottom hole pressure increases enough to overcome the stresses and the rock tensile strength so that the formations breaks or fractures. Sometimes the breaks occur along planes of weakness that are called joints. Naturally occurring joints in the formation may also be opened, expanded and propagated by the fluid. In order to keep these newly formed and enlarged fractures, cracks or joints open, once the pressure and fluid are removed, the proppants are left behind. They in essence hold open, i.e., "prop" open, the newly formed and enlarged fractures, cracks, or joints in the formation.

SUMMARY

Accordingly, there has been a long-standing and unfulfilled need for better abilities to monitor, analyze, plan and control the exploration and production of natural resources, and in particular, the exploration and production of hydrocarbon resources. Traditional monitoring and control applications have significant failings and have not fully met these continuing needs. Accordingly, the present inventions, among other things, solve these needs by providing the articles of manufacture, devices and processes taught, disclosed and claimed herein.

Thus, there is provide a method of enhancing the production of hydrocarbons from a well, the method including: obtaining a first microbiome information at time $t_1$ from hydrocarbons produced from a well, the well having a first production zone, and a second production zone; performing an evaluation on the first microbiome information, the evaluation including: a relationship based processing having a related genetic material component and an industrial setting component; and, a bioinformatics stage; whereby a microbiome finger print is obtained for each production zone of the well at time $t_1$; obtaining a second microbiome information at time $t_2$ from hydrocarbons produced from the well; performing an evaluation on the second microbiome information, the evaluation including: a relationship based processing having a related genetic material component and an industrial setting component; and, a bioinformatics stage; whereby a second microbiome finger print is obtained for each production zone of the well at time $t_2$; and, comparing the first microbiome finger print and the second microbiome finger print; whereby any change in the amount of hydrocarbons produced from each zone is identified.

Additionally, there is provided the present systems, operations and methods having one or more of the following features: wherein, the first microbiome information, the second microbiome information, or both the first and the second microbiome information are selected from the group consisting of historic microbiome information, real time microbiome information, derived microbiome information and predictive microbiome information; wherein, the historic microbiome information is selected from the group consisting of the Earth Microbiome Project, the Human Microbiome Project, American Gut, GreenGenes, the Ribosomal Database Project, the International Nucleotide Sequence Database Collaboration (INSDC), and American Gut; wherein, the industrial setting component is selected from the group consisting of GPS data; location data, system component identification, subsystem component identification, pump station true vertical depth of a well, pH, measured depth of a well, processing stage, geological parameter, formation permeability, viscosity, porosity, pressure, flow, and temperature; wherein, the bioinformatics stage includes submitting the microbiome information to QIIME processing; wherein, the bioinformatics stage includes: compiling metadata mapping; barcode decoding; OTU picking; constructing phylogentic trees; constructing a BIOM table; and UniFac and PCoA; wherein, the bioinformatics stage includes: compiling metadata mapping; barcode decoding; OTU picking; constructing phylogentic trees; constructing a BIOM table; and UniFac and PCoA; wherein, the bioinformatics stage includes: compiling metadata mapping; barcode decoding; OTU picking; constructing phylogentic trees; constructing a BIOM table; and UniFac and PCoA; wherein, the bioinformatics stage includes: compiling metadata mapping; OTU picking; constructing phylogentic trees; constructing a BIOM table; and UniFac and PCoA; wherein, the bioinformatics stage includes: compiling metadata mapping; OTU picking; constructing a BIOM table; and UniFac and PCoA; and wherein, the bioinformatics stage includes: constructing a BIOM table; and UniFac and PCoA.

Yet further, there is provided the present systems, operations and methods having one or more of the following features: wherein a zone in the well is shut down based at least in part on the comparison (e.g., comparing the first microbiome finger print and the second microbiome finger print; whereby any change in the amount of hydrocarbons produced from each zone is identified); wherein a zone in the well is shut down based at least in part on the comparison; wherein a zone in the well is shut down based at least in part on the comparison; wherein a new production zone in the well is opened based at least in part on the comparison; wherein a new production zone in the well is opened based at least in part on the comparison; and wherein a new production zone in the well is opened based at least in part on the comparison.

Moreover, there is provided a method of monitoring the production of hydrocarbons from a well, the method including: obtaining a microbiome information from hydrocarbons produced from a well having a plurality of production zones; and, performing an evaluation on the microbiome information; whereby a microbiome finger print is produced for at least two of the plurality of production zones.

Additionally there is provided the present systems, operations and methods having one or more of the following features: wherein the microbiome information comes from a single sample of hydrocarbons; wherein the microbiome information comes from a plurality of samples of hydrocarbons; wherein the evaluation includes: a relationship based processing having a related genetic material component and an industrial setting component; and, a bioinformatics stage; wherein, the industrial setting component is selected from the group consisting of GPS data; location data, system component identification, subsystem component identification, pump station true vertical depth of a well, measured depth of a well, processing stage, geological parameter, formation permeability, viscosity, porosity, pressure, flow, and temperature; wherein, the bioinformatics stage includes submitting the microbiome information to QIIME processing; and wherein, the bioinformatics stage includes: compiling metadata mapping; barcode decoding; OTU picking; constructing phylogentic trees; constructing a BIOM table; and UniFac and PCoA.

Further there is provided a method of enhancing the production of hydrocarbons from an oil field, the method including: obtaining a first microbiome information from hydrocarbons produced from a first well in an oil field having a plurality of wells at time $t_1$; obtaining a second microbiome information from hydrocarbons produced from a second well in an oil field having a plurality of wells at about time $t_2$; wherein time $t_1$ and $t_2$ can be the same or different day; performing an evaluation on the first microbiome information, the evaluation including: a relationship based processing having a related genetic material component and an industrial setting component; and, a bioinformatics stage; whereby a microbiome finger print is obtained for the first well at time $t_1$; performing an evaluation on the second microbiome information, the evaluation including; a relationship based processing having a related genetic material component and an industrial setting component; and, a bioinformatics stage; whereby a microbiome finger print is obtained for the second well at time $t_2$; obtaining a second microbiome information from hydrocarbons produced from the first well in the oil field at time $t_{1+n}$; obtaining a second microbiome information from hydrocarbons produced from the second well in the oil field at about time $t_{2+n}$; wherein $n$ can be the same or different number of days; performing an evaluation on the second microbiome information from the first well, the evaluation including: a relationship based processing having a related genetic material component and an industrial setting component; and, a bioinformatics stage; whereby a microbiome finger print is obtained for the first well at time $t_{1+n}$; performing an evaluation on the second microbiome information from the second well, the evaluation including: a relationship based processing having a related genetic material component and an industrial setting component; and, a bioinformatics stage; whereby a microbiome finger print is obtained for the second well at time $t_{2+n}$; and analyzing the microbiome finger prints and based at least in part on the analysis performing an activity in the oil field.

Still further there is provided the present systems, operations and methods having one or more of the following features: wherein the activity in the oil field includes changing the well spacing for the oil field; wherein the activity in the oil field includes drilling a new well; wherein the activity in the oil field includes determining a microbiome well spacing for the oil field and drilling a new well base at least in part on the microbiome well spacing; and wherein the activity in the oil field includes restimulating a well.

Additionally there is provided a method of controlling the production of hydrocarbons from a well including: analyzing a fluid from a well to provide a first microbiome information; associating the first microbiome information with an operation condition of the well; obtaining a second microbiome information; associating the second microbiome information with the first microbiome information; and, evaluating the first microbiome information, the associated condition, and the second microbiome information, the evaluation including QIIME processing, the QIIME processing including constructing a phylogentic tree, constructing a BIOM table, UniFac, and PCoA; whereby the evaluation identifies a production characteristic of the well; and, controlling the production of hydrocarbons from the well based at least in part upon the identified production characteristic.

Moreover there is provided the present systems, operations and methods having one or more of the following features: wherein the identified production characteristic is selected from the group consisting of water cut, zone production, change in zone production, and non-biologic change in production.

Additionally there is provided a method of forming a borehole in the earth for the recovery of hydrocarbons, the method including: locating a rig at a well site; circulating a fluid in a borehole at the well site, whereby material from within the borehole is removed from the borehole by the fluid; obtaining a sample of the fluid; analyzing the sample; obtaining microbiome information of the sample; and, performing an evaluation on the microbiome information, whereby the evaluation provides directing information to direct the formation of the borehole.

Still further there is provided the present systems, operations and methods having one or more of the following features: wherein the analysis includes extracting material including genetic material selected from the group consisting of a SSU rRNA gene 16S, SSU rRNA gene 18S, LSU rRNA gene 23S, LSU rRNA gene 28S, ITS in the rRNA operon, and ITS in the rRNA cpn60; wherein, the microbiome information is selected from the group consisting of historic microbiome information, real time microbiome information, derived microbiome information, predictive microbiome information; wherein the analysis includes selection and sequencing of the material; wherein the information relates to a pay zone; wherein the information relates to a pay zone; wherein the analysis includes preparation of libraries; wherein directing the formation of the borehole including a modification to the drilling plan; wherein directing the formation of the borehole including locating the borehole in a particular position within formation; wherein directing the formation of the borehole including locating the borehole in a particular position within formation; and, wherein directing the formation of the borehole including an activity selected from the group consisting of placing a plug, creating a brank, side tracking, determining the depth of the borehole, a casing plan, determining the location of perforations, determining the placement of perforations, following a lateral hydrocarbon containing formation, and secondary recovery from the borehole.

Still further there is provided a method of forming a borehole in the earth for the recovery of hydrocarbons, the method including: creating a borehole in the earth at the well site; advancing the borehole and circulating a drilling fluid, whereby material from within the borehole is removed from the borehole by the drilling fluid; obtaining a sample of the drilling fluid; analyzing the sample; obtaining microbiome information of the sample; and, performing an evaluation on the microbiome information, whereby the evaluation provides directing information to direct the formation of the borehole.

Further there is provided the present systems, operations and methods having one or more of the following features: wherein the sample for analysis consists essential of material removed from within the borehole; wherein the solids are essentially separated from the drilling fluid, and the analysis is performed on at least one of the separated solids or fluid; wherein the analysis includes providing a phylogenetic tree; wherein the analysis includes a correction step; wherein the analysis includes an extraction procedure selected from the group consisting of beating, sonicating, freezing and thawing, and chemical disruption; wherein the analysis includes amplification of at least a portion of the material; wherein the microbiome information includes information obtained from variable regions of the 16S rRNA; wherein the variable regions are selected from the group consisting of V2, V4, and V6; and wherein directing the formation of the borehole including an activity selected from the group consisting of placing a plug, creating a brank, side tracking, determining the depth of the borehole, a casing plan, determining the location of perforations, determining the placement of perforations, following a lateral hydrocarbon containing formation, and secondary recovery from the borehole.

Yet additionally there is provided a method of evaluating and planning an oil field to optimize the placement of wells and recovery of hydrocarbons from the field, the method including: obtaining microbiome information of a plurality of samples from selected locations in a hydrocarbon containing formation beneath the field of the sample; and, performing an evaluation on the microbiome information, whereby the evaluation provides directing information to direct the placement of wells in the field.

Further there is provided the present systems, operations and methods having one or more of the following features: wherein the analysis includes providing a phylogenetic tree; wherein the analysis includes providing a genetic barcode to a sample of the material; wherein the microbiome information includes a OTU; wherein the microbiome information defines a biogeographical pattern; wherein the microbiome information includes information obtained from variable regions of the 16S rRNA; wherein the variable regions are selected from the group consisting of V2, V4, and V6; wherein the evaluation includes forming an n-dimensional plot, where n is selected from the group of integers consisting of 3, 4, 5, 6, 8, 9, 10, 11, 12, 13, and 14; wherein the evaluation includes measuring a change in gene sequences and using the measured change as a molecular clock in the evaluation to determine the related nature of material; and, wherein the evaluation includes measuring a change selected from the group consisting of a change in gene sequences, and change in gene sequences and using the measured change as a molecular clock in the evaluation to determine the related nature of material.

Still further there is provided a method of hydraulically fracturing a formation for the recovery of hydrocarbons, the method including: obtaining microbiome information of a sample of fracturing fluid; and, performing an evaluation on the microbiome information, whereby the evaluation provides directing information to direct a fracturing operation in the well.

Additionally there is provided a method of forming a borehole in the earth for the recovery of hydrocarbons, the method including: obtaining microbiome information from a sample of a circulation fluid from a borehole; and, performing an evaluation on the microbiome information, whereby the evaluation provides directing information to direct the recovery of a material from the borehole.

There is additionally provided a port on a drilling fluid return line, the port having a pressure reducing value, and a nipple for the sterile attachment to a sampling container.

Still further there is provided an oil field microbiometric sequencing field unit including: sample collection containers; personal protective equipment; pipettors; electrophoresis equipment; fluorometric measuring devices; centrifuges; PCR hoods; thermocylers; cooling and heating unit for 96 well plates; DNA/RNA extraction reagents; quantification reagents for genetic material; liquid-handling robot; sequencer; compute resources; and, high speed data transmission capabilities.

Additionally there is provided the present systems, operations and methods having one or more of the following features: wherein the directing information includes oil saturation and permeability data; wherein the directing information includes well wettability data; wherein the directing information includes data for a well feature, the well feature selected from the group consisting of oil viscosity, temperature, pressure, porosity, oil saturation, water saturation, and compressibility; wherein the directing information includes subsurface flow communication and reservoir connectivity data; wherein the directing information includes propensity for producing oil versus gas data; wherein the directing information includes data about the production zone that improves vertical and aerial conformance; wherein the directing information includes chemical and physical properties of a treatment fluid; wherein the directing information includes chemical and physical properties of a production fluid; wherein the directing information includes environmental impact data; wherein the directing information includes data for a high resolution subsurface geologic map of a production zone; wherein the directing information includes oil-water contact level data; wherein the directing information includes data on the likelihood of oil coning or cusping; wherein the directing information includes lease valuation data; wherein the directing information includes recovery factor data; wherein the directing information includes predictive data regarding the existence of $H_2S$ in a well; wherein the directing information includes predictive data for a future potential oil reservoir; wherein the directing information includes oil saturation and permeability data; wherein the directing information includes well wettability data; wherein the directing information includes data for a well feature, the well feature selected from the group consisting of oil viscosity, temperature, pressure, porosity, oil saturation, water saturation, and compressibility; wherein the directing information includes subsurface flow communication and reservoir connectivity data; wherein the directing information includes propensity for producing oil versus gas data; wherein the directing information includes data about the production zone that improves vertical and aerial conformance; wherein the directing information includes chemical and physical properties of a treatment fluid; wherein the directing information includes chemical and physical properties of a production fluid; wherein the directing information includes environmental impact data; wherein the directing information includes data for a high resolution subsurface geologic map of a production zone; wherein the directing information includes oil-water contact level data.

Yet further there is provided the present systems, operations and methods having one or more of the following features: wherein the directing information is selected from the group consisting of oil saturation data, permeability data, well wettability data, oil viscosity data, temperature data, porosity data, water saturation data, compressibility data, subsurface flow communication data, reservoir connectivity data, vertical conformance data, aerial conformance data, oil coning data, oil cusping data, lease valuation data, recovery factor data, and $H_2S$ data.

Still further there is provided the present systems, operations and methods having one or more of the following features: wherein the directing information is selected from the group consisting of oil saturation data, permeability data, well wettability data, oil viscosity data, temperature data, porosity data, water saturation data, compressibility data, subsurface flow communication data, reservoir connectivity data, vertical conformance data, aerial conformance data, oil coning data, oil cusping data, lease valuation data, recovery factor data, and $H_2S$ data.

BRIEF DESCRIPTION OF THE DRAWINGS

FIG. 9 is a graph and illustration of an embodiment of a matrix in accordance with the present inventions.

DESCRIPTION OF THE PREFERRED EMBODIMENTS

Figures 1, 1A:
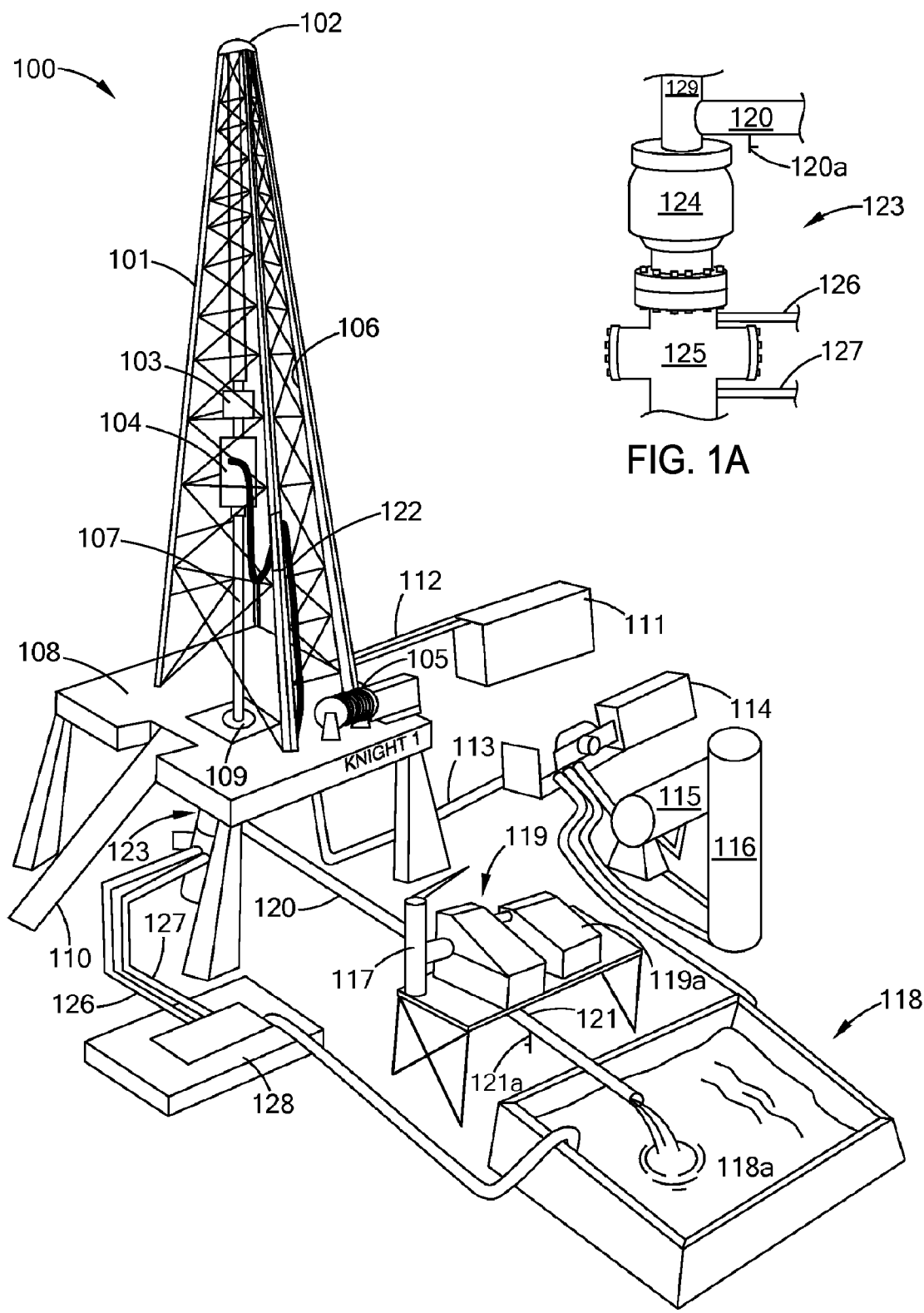
FIG. 1 is a perspective view of an embodiment of a drilling site in accordance with the present inventions.
FIG. 1A is a perspective view of an embodiment of the bell nipple arrangement of the embodiment of FIG. 1.

In general, the present inventions relate to methods, systems and processes for the utilization of microbial and DNA-related information as well as the determination and relative characterization of microbes and genetic material for use in the exploration and production of natural resources in industrial settings. These industrial settings include the exploration, determination, and recovery of natural resources, including minerals, and energy sources, such as hydrocarbons including oil and natural gas. Further, specific fields for these industrial settings for the present invention would include, for example, energy exploration and production including all phases of well planning, construction, completion, production, intervention and workover, and decommissioning including perforation and hydraulic fracturing and reservoir management.

Thus, microbes and genetic material exist in energy, hydrocarbon, and in particular oil and natural gas exploration and production, settings, sites or environments. Such microbes and genetic material range from historic, e.g., archaeological sources, from the surface to deep within the earth, the air, and essentially within any location that has not been sterilized (and even in such settings genetic material that may be useful for analysis may be present). These microbes and their genetic material provide a significant yet largely untapped source of information for monitoring, planning, developing, enhancing improving, and conducting natural resource exploration and production, energy exploration and production, and in particular the exploration and production of hydrocarbons.

In general, the present inventions further relate to systems and methods for determining and characterizing the rnicrobiomes of natural resource exploration and production settings, energy exploration and production settings, and in particular, settings relating to the exploration and production of hydrocarbons; and in particular determining through relationship-based processing, which include custom and unique analytics tools and algorithms, data management, cleansing, filtering, and quality control, which in turn provide information about these energy exploration and production industrial settings. Such characterized information, for example, can have, and be used for, predictive, historical, analytic, development, control and monitoring purposes.

The relationship-based processing utilizing microbiome information may include historic microbiome information, real-time-based microbiome information, derived microbiome information, and predictive microbiome information, and combinations and variations of these. Further, this relationship-based processing utilizes these various types of microbiome information in combination with other data and information such as GPS data; traditional industrial automation data, e.g., LWD, MWD, flow rate, temperature, formation pressure; geologic data; and geological data.

This information, data, processing algorithms support software, such as human machine interface (HMI) programs and graphic programs, and databases, may be cloud-based, locally-based, hosted on remote systems other than cloud-based systems, contained in or associated with a field unit, and combinations and variations of these.

Thus, real-time, derived, and predicted data may be collected and stored and thus become historic data for an ongoing process, setting, or application. In this manner, the collection, use, and computational links can create a real-time situation in which machine learning can be applied to further enhance and refine the industrial activities or processes. Further, real-time, derived, predictive, and historic data can be, and preferably is, associated with other data and information. Thus, the microbiome information can be associated with GPS data; location data, e.g., MD, TVD LWD, MWD; formation information; particular components and subsystems in a drilling, fracturing, intervention or other oil field system a stage of a hydraulic fracturing operation; geological parameters including formation permeability and porosity.

Thus, real-time, derived, historic, and predictive microbiome information may be further combined or processed with these other sources of information and data regarding the industrial setting or process, e.g., hydrocarbon exploration and production, to provide combined, derived, and predictive information. In this manner, the microbiome information is used in combination with other data and information to provide for unique and novel ways to conduct industrial operations, to develop or plan industrial operations, to refine and enhance existing industrial operations and combinations of these and other activities.

Preferably, these various types of information and data are combined where one or more may become metadata for the other. In this manner, information may be linked in a manner that provides for rapid, efficient, and accurate processing to provide useful information relating to the industrial setting. Thus for example, in forming a well, the MD location down hole may be linked as metadata to the real-time microbiome information during drilling and compared with similarly linked meta-data obtained during hydraulic fracturing. Thus for a further example in the hydrocarbon exploration and production setting, GPS data, geologic data, TVD data and MD data may be used as metadata associated with real-time microbiome data obtained from well cutting returns. This metadata linked real-time microbiome data is then analyzed during the advancement of the borehole to determine the characterization of the formation and a perforation and hydraulic fracturing plan to improve production. Thus, for an example in an exploration and production hydrocarbon setting, microbiome data obtained from well cutting returns may be used as metadata and associated with real-time GPS data, geologic data, and measured total depth data. This metadata-linked historic microbiome data is then analyzed during the advancement of the borehole, potentially in conjunction with real-time data, to determine the characterization of the formation and a perforation and hydraulic fracturing plan to improve production.

Additionally, microbiome data can be associated with publically available, proprietary and combinations of both, information about formations and natural resource. Thus, for example a large energy company having considerable information about the value, size and location of its oil field reserves, could combine its proprietary information with microbiome information, and greatly enhance, among other things, the accuracy of the evaluation of its holdings, as well as, the ability to recover greater amounts of those holdings from the earth. Further, such microbiome information could be combined with publically available information and provide enhanced ability to value the holdings of the energy company, and thus, form a basis for investment decisions in the that energy company. This use of microbiome information in economic analysis may be directed to may other situations, in addition to a single energy company. Thus, this microbiome economic analysis could be applied to all lease holders for a particular oil field, it could be applied to an oil field to assist in determining a value for the reserves in that field, it could be applied to entities associated with a particular country, or geographic area and it could be applied to industrial setting in addition to the oil field, and energy exploration and production.

Thus it is understood that microbiome information may be used as metadata or may be the underlying information with which the metadata is associated. Further, in creating larger databases it may be advantageous to have the ability to disassociate some metadata from the underlying information. In this manner, historic microbiome information may be collected which has far greater utilization in which companies or individuals are more willing to participate or contribute yet which provides the ability to be utilized in further and improved derived and predictive activities.

In general, historic microbiome data may be obtained from known databases or it may be obtained from conducting population studies or censuses of the microbiome for the particular industrial setting. Thus samples of biological materials are collected and characterized. This characterized information is then processed and stored. Preferably, the data is processed and stored in a manner that provides for ready and efficient access and utilization in subsequent steps, often using auxiliary data structures such as indexes or hashes.

In general, real-time microbiome data may be obtained from conducting population studies or censuses of the microbiome as it exists at a particular point in time, or over a timeseries, for the particular industrial setting. Thus samples of biological materials are collected and characterized. This characterized information is then processed and stored. Preferably, the data is processed and utilized in subsequent steps or may be stored as historic data in a manner that provides for ready and efficient access and utilization in subsequent steps.

Generally, microbiome information may be contained in any type of data file that is utilized by current sequencing systems or that is a universal data format such as for example FASTQ (including quality scores), FASTA (omitting quality scores), GFF (for feature tables), etc. This data or files may then be combined using various software and computational techniques with identifiers or other data, examples of such software and identifiers for the combining of the various types of this information include the NOM file format and the MI(x)S family of standards developed by the Genomic Standards Consortium. For example, information from a programmable logic controller (PLC) in an industrial setting may be combined with microbial information for storage or further processing. Similarly, information from measuring-while-drilling (MWD), logging-while-drilling (LWD), and M/LWD which is provided in known formats and has known user interfaces may be combined with microbiome information for display and analysis in subsequent processing. Additionally by way of example, in agricultural settings, data from a harvesting combine regarding yield, microbiome information, and commodities price information may be displayed or stored or used for further processing. The combination and communication of these various systems can be implemented by various data processing techniques, conversions of files, compression techniques, data transfer techniques, and other techniques for the efficient, accurate, combination, signal processing and overlay of large data streams and packets.

In general, real-time, historic, and combinations and variations of this microbiome information is analyzed to provide a census or population distribution of various microbes. Unlike conventional identification of a particular species that is present, the analysis of the present invention determines in an n-dimensional space (a mathematical construct having 2, 3, 5, 12, 1000, or more dimensions), the interrelationship of the various microbes present in the system, and potentially also interrelationship of their genes, transcripts, proteins and/or metabolites. The present inventions provide further analysis to this n-dimensional space information, which analysis renders this information to a format that is more readily usable and processable and understandable. Thus, for example, by using the techniques of the present invention, the n-dimensional space information is analyzed and studied for patterns of significance pertinent to a particular industrial setting and then converted to more readily usable data such as for example a 2-dimensional color-coded plot for presentation through a HMI (Human-Machine Interface).

Additionally, the n-dimensional space information may be related, e.g., transformed or correlated with, physical, environmental, or other data such as the presence of a mineral or the geologic time period and conditions under which a particular formation was created, either by projection into the same spatial coordinates or by relation of the coordinate systems themselves, or by feature extraction or other machine learning or multivariate statistical techniques. This related n-dimensional space information may then be further processed into a more readily usable format such as a 2-dimensional representation. Further, this 2-dimensional representation and processing may, for example, be based upon particular factors or features that are of significance in a particular industrial setting. The 2-dimensional information may also be further viewed and analyzed for determining particular factors or features of significance for a system. Yet further, either of these types of 2-dimensional information may be still further processed using for example mathematical transformation functions to return them to an n-dimensional space which mathematical functions which may be based upon known or computationally determined factors or features.

Thus the present inventions provide for derived and predicted information that can be based upon the computational distillation of complex n-dimensional space microbiome information, which may be further combined with other data. This computationally distilled data or information may then be displayed and used for operational purposes in the industrial setting, it may be combined with additional data and displayed and used for operational purposes in the industrial setting, it may be alone or in combination with additional information subjected to trend, analysis, to determine features or factors of significance, it may be used for planning and operational purposes in combinations and variations of these and other utilizations.

Turning to FIG. 1 there is shown an embodiment of a drilling rig site for the drilling of an oil well. Thus, the drilling rig 100 has a derrick 101, having a crown block 102, a traveling block 103, a top drive, 104, a drawworks 105, a drill line 106, and a rotary table 109. The derrick 101 is positioned upon an elevated rig floor 108. (It being understood that this is a simplified representation of a drilling rig, and that other components, that are known to the art, such as monkey board, dog house, elevators, pumps, manifolds, lines, iron roughnecks, kellys, etc., may be present. Further, other types of drilling rigs, such as masts, and rams, etc., may be used.) The drilling rig 100 has a pipe handling system 110 for bring drilling pipe and drilling strings from a holding area to the rig floor 108. The drilling rig 100, has a drill string 107 positioned in the top drive 104, and extending through the rotatory table 109, the bell nipple 129, below the rig floor 108 (and better seen in FIG. 1A), a BOP 123, and down into a borehole (not shown in the figure). Turning the FIG. 1A there is shown the embodiment of the BOP 123 and bell nipple 129 that are located below the rig floor 108. The bell nipple 129 is attached by for example a bolted flange to a flange on an annular preventer 124, which is connected, by bolted flanges, to one or more ram shears, e.g., 125. Ram shears would include any mechanical devices that clamp, grab, hold, cut, sever, crush, or combinations thereof, a tubular within a BOP stack, such as shear rams, blind rams, variable rams, variable pipe rams, blind-shear rams, pipe rams, casing shear rams, and preventers such as Hydril's HYDRIL PRESSURE CONTROL COMPACT Ram, Hydril Pressure Control Conventional Ram, HYDRIL PRESSURE CONTROL QUICK-LOG, and HYDRIL PRESSURE CONTROL SENTRY Workover, SHAFFER ram preventers, and ram preventers made by Cameron.

The BOP 123 has choke 127 and kill 126 lines. These lines are associated with a manifold assembly 128, and are used to provide drilling mud, e.g., heavy mud, into the well to address pressure management, including situations, such as a well kick, and emergency pressure and flow situations.

An electrical generator 111, supplies power to the rig by various electrical lines, e.g., electric race way 112.

During drilling the top drive 104 rotates the drill string 107 that has a drill bit (not shown) at its distal end, and which is engaged against the bottom of the borehole to advance the borehole. Weight is provided to the drill bit (weight-on-bit ("WOB")) through for example the use on drilling collars.

During drilling, as well as at other times when the well is being circulated, drilling mud is pumped by mud pump assembly 114 to drilling mud line 113 which is connected to flexible inlet mud hose 122, which provide the mud to the top drive, where the mud is directed down the interior of the drill string 107. The mud is pumped down the drill string 107, to the drill bit and out the drill bit, where is carries away the cuttings from the advancement of the borehole. The drilling mud, mixed with the cuttings, returns up the annulus between the borehole wall and the drill string. (Note the mud or any drilling or sampling fluid can also be circulated while the bit is not rotating, and the circulation can be a reverse circulation as well.) The returning drilling mud and cuttings can be sampled, for example, from mud return line 120, at for example sample point 120a. Sample point 120a may be located anywhere along the mud return line 120 that is safe and convenient to obtain the samples.

Mud return line 120 delivers the mud and cuttings to a shaker or screen assembly 119, which begin the separation and clean of the drilling mud. A sample of the removed solids can be obtained from sample point 119a. Gas from the mud is separated from by the mud/gas separator 117. The drilling mud is then delivered by line 121 to a mud pit, (e.g., holding pond, tanks, etc.) 118. Samples may be taken from sample point 118a.

The mud handling system additionally has water storage tanks 115, mud holding tanks 116 (as well as other holding tanks, chemical storage, etc., not shown in the figure).

Drilling mud (which should be given its broadest definition and will include all types of drilling fluids) can generally be liquid, gas, and foam. Different types of drilling mud may be used during the formation of a borehole, depending upon the conditions and requirements for drilling the well. Drilling mud can include: freshwater systems; saltwater systems (e.g., brine); oil- or synthetic-based systems (e.g., diesel), and pneumatic systems (e.g., air, mist, foam, gas) "fluid" systems. Water-based muds are the most widely used systems. Oil-based systems and synthetic bases systems are typically invert-emulsion having an oil or synthetic base fluid as the continuous (or external) phase, and brine as the internal phase.

Water-based drilling muds may generally be fresh water, seawater, brine, saturated brine, or a formate brine. The type of fluid selected depends on anticipated well conditions or on the specific interval of the well being drilled. For example, the surface interval typically is drilled with a low-density water- or seawater-based mud that contains few commercial additives. These systems incorporate natural clays in the course of the drilling operation. Some commercial bentonite or attapulgite also may be added to aid in fluid-loss control and to enhance hole-cleaning effectiveness.

Water based system typically can be nondispersed systems and dispersed systems.

Nondispersed sytems generally are simple gel-and-water systems used for tophole drilling are nondispersed, as are many of the advanced polymer systems that contain little or no bentonite. The natural clays that are incorporated into nondispersed systems are managed through dilution, encapsulation, and/or flocculation. A properly designed solids-control system can be used to remove fine solids from the mud system and help maintain drilling efficiency. The low-solids, nondispersed (LSND) polymer systems rely on high- and low-molecular-weight long-chain polymers to provide viscosity and fluid-loss control. Low-colloidal solids are encapsulated and flocculated for more efficient removal at the surface, which in turn decreases dilution requirements. Specially developed high-temperature polymers are available to help overcome gelation issues that might occur on high-pressure, high-temperature (HP/HT) wells. With proper treatment, some LSND systems can be weighted to 17.0 to 18.0 ppg and run at 350° F. and higher.

Dispersed systems, generally, are water-based systems that are treated with chemical dispersants that are designed to deflocculate clay particles to allow improved rheology control in higher-density muds. Widely used dispersants include lignosulfonates, lignitic additives, and tannins. Dispersed systems typically require additions of caustic soda (NaOH) to maintain a pH level of 10.0 to 11.0. Dispersing a system can increase its tolerance for solids, making it possible to weight up to 20.0 ppg. The commonly used lignosulfonate system relies on relatively inexpensive additives and is familiar to most operator and rig personnel. Additional commonly used dispersed muds include lime and other cationic systems.

Generally, saltwater drilling fluids often are used for shale inhibition and for drilling salt formations. They also are known to inhibit the formation of ice-like hydrates that can accumulate around subsea wellheads and well-control equipment, blocking lines and impeding critical operations. Solids-free and low-solids systems can be formulated with high-density brines, such as: calcium chloride; calcium bromide; zinc bromide; potassium and cesium formate; and polymer drilling fluids Generally, polymer drilling fluids are used to drill reactive formations where the requirement for shale inhibition is significant. Shale inhibitors frequently used are salts, glycols and amines, all of which are incompatible with the use of bentonite. These systems typically derive their viscosity profile from polymers such as xanthan gum and fluid loss control from starch or cellulose derivatives. Potassium chloride is an inexpensive and highly effective shale inhibitor that is widely used as the base brine for polymer drilling fluids in many parts of the world. Glycol and amine-based inhibitors can be added to further enhance the inhibitive properties of these fluids.

Typically, barite can be used to increase system density, and specially treated organophilic bentonite is the primary viscosifier in most oil-based systems. The emulsified water phase also contributes to fluid viscosity. Organophilic lignitic, asphaltic and polymeric materials are added to help control HP/HT (High pressure/High temperature) fluid loss. Oil-wetting is essential for ensuring that particulate materials remain in suspension. The surfactants used for oil-wetting also can work as thinners. Oil-based systems usually contain lime to maintain an elevated pH, resist adverse effects of hydrogen sulfide ($H_2S$) and carbon dioxide ($CO_2$) gases, and enhance emulsion stability.

Typically, shale inhibition is one of the key benefits of using an oil-based system. The high-salinity water phase helps to prevent shales from hydrating, swelling, and sloughing into the wellbore. Most conventional oil-based mud (OBM) systems are formulated with calcium chloride brine, which appears to offer the best inhibition properties for most shales.

Generally, the ratio of the oil percentage to the water percentage in the liquid phase of an oil-based system is called its oil/water ratio. Oil-based systems generally function well with an oil/water ratio in the range from 1/99 to 99/1, but typically may be 65/35 and may generally have an observed range from 70/30 to 90/10.

The foregoing description of drilling mud is a general description, and it is recognized that other types and forms of drilling muds are known, and may be developed, formulated or used.

Figure 2:
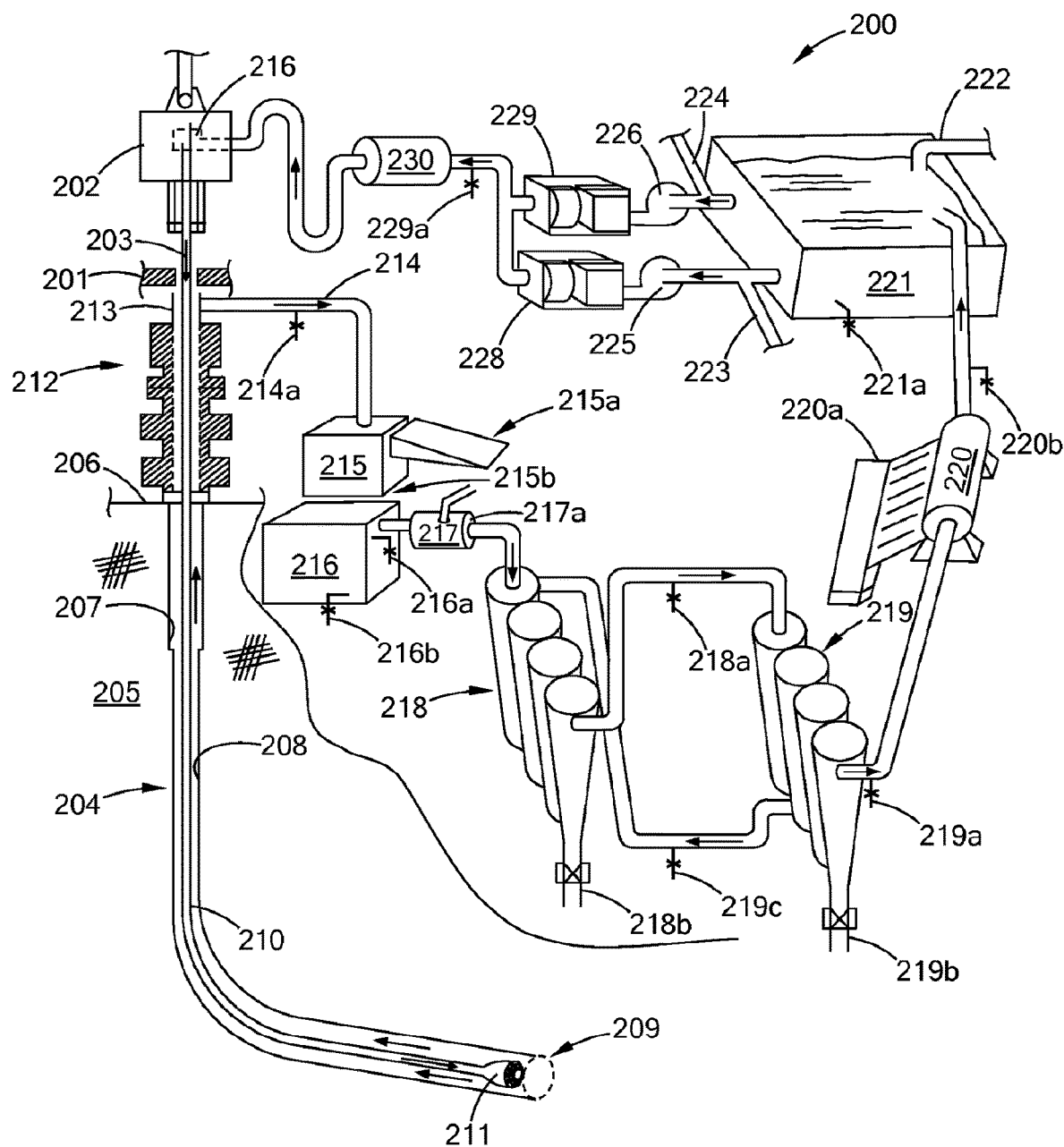
FIG. 2 is a cross-sectional and perspective view of an embodiment of a borehole and drilling mud handling system in accordance with the present inventions.

Turning to FIG. 2 there is shown a cross section and perspective view of a bore hole and drilling mud system. Thus, the top drive 202 has a passage 216 for providing drilling mud into the drill pipe 203 that is located in the top drive 202 and which drill pipe 203 is the top pipe in drill string 210. Drill string 210 extends from the top drive 202 below the rig floor 201 into a diverting apparatus 213, e.g., a bell nipple, into the BOP 212, and then into bore hole 204. Bore hole 204 is located in a formation 205 below the surface of the earth 206. The bore hole 204 has an upper casing 207, and an intermediate casing 208, The drill string 210 has a drill bit 211 that is engaged against and drilling the bottom 209 of the bore hole 204.

The flow of the drilling mud is shown by the various arrows in FIG. 2. Thus, the drilling mud flows down the interior of the drill string 210, through and out of the drill bit 211, where it carries away the cuttings and moves up the borehole 204 in the annulus formed between the borehole walls and the drill string. The returning drilling mud and cuttings travel up through the BOP and directed by the diverting assembly 213 into of return line 214. Return line 214 delivers the drilling mud and cuttings to the mud system 200.

A sample port 214a to obtain a sample for microbiometnc analysis of the returns is provided in line 214. Line 214 delivers the returns, e.g., drilling mud and cuttings, to a shaker, or shaker table or system, 219, having sampling ports 215a and 215b. The shaker table 215 separates solid from the drilling mud. Thus, sample port 215a would have sample material that of high solids, and sample point 215b would have liquid drilling fluid that has had a substantial amount of the solids removed from it. From the shaker the drilling mud is deliver into a settling pit or tank 216, which also has a sampling ports 216a, and 216b. Where sample material 216b is lower in the tank 216 and thus would provide a sample of heavier materials that have settled out, and sample port 216a is higher in the tank 216 and thus would provide lighter weight materials.

The drilling mud is then delivered to degasser 217, having sampling port 217a. From the degasser 217 the drilling mud is delivered to a primary cyclonic cleaner bank 218 and to a secondary cyclonic cleaner bank 219. Sample ports 218a, 218b, 219a, 219b, 219c are associated with the two cleaner banks, to obtain samples of the drilling mud and the various materials that are being separated from the drilling. The drilling mud is then delivered to a mud centrifuge 220, which has a sample collection point 220a. From the centrifuge 220 the mud is delivered to a mud pit 221, having a sample port 221a, Drilling mud from the mud pit 220 flow into centrifugal pumps 225, 226, which feed mud pumps 228, 229 (which can be duplex, or triplex pump assemblies). Various, feed or make up lines 223, 226, 222 are provided to add material, chemicals, fluids, etc., to the drilling mud.

The mud pumps 228, 229 pump the mud through a pulse dampener 230 and from there it is delivered to the top drive and drill string. A sample port 229a is provided in the high pressure line leaving the mud pumps.

It being understood that the mud handling system 200 is only an illustrative system, and that other pumps, tanks, lines, and other equipment, and variations thereof, may be used at a drilling site.

These various sample ports can be used to provide samples of different materials for microbiometeric analysis. These ports, and the obtained samples may also be used for other types of, e.g., conventional or traditional, monitoring and analysis, such as pressure, temperature, solids, etc. In this manner both traditional and microbiometric information can be obtained in integrated or associated. Further in this manner as information is obtained about the microbiome for a particular well, or even a particular MD for the bore hole, different or multiple sample points can be used. These sample points can be associated with other information and the derived and predicative data and information can be enhances and expanded. These types of information from multiple wells in a field, or associated with a reservoir, or even a formation or rock type, can then further be associated, to provided addition data and information, e.g., historic, real time, derived and predictive.

Figure 3:
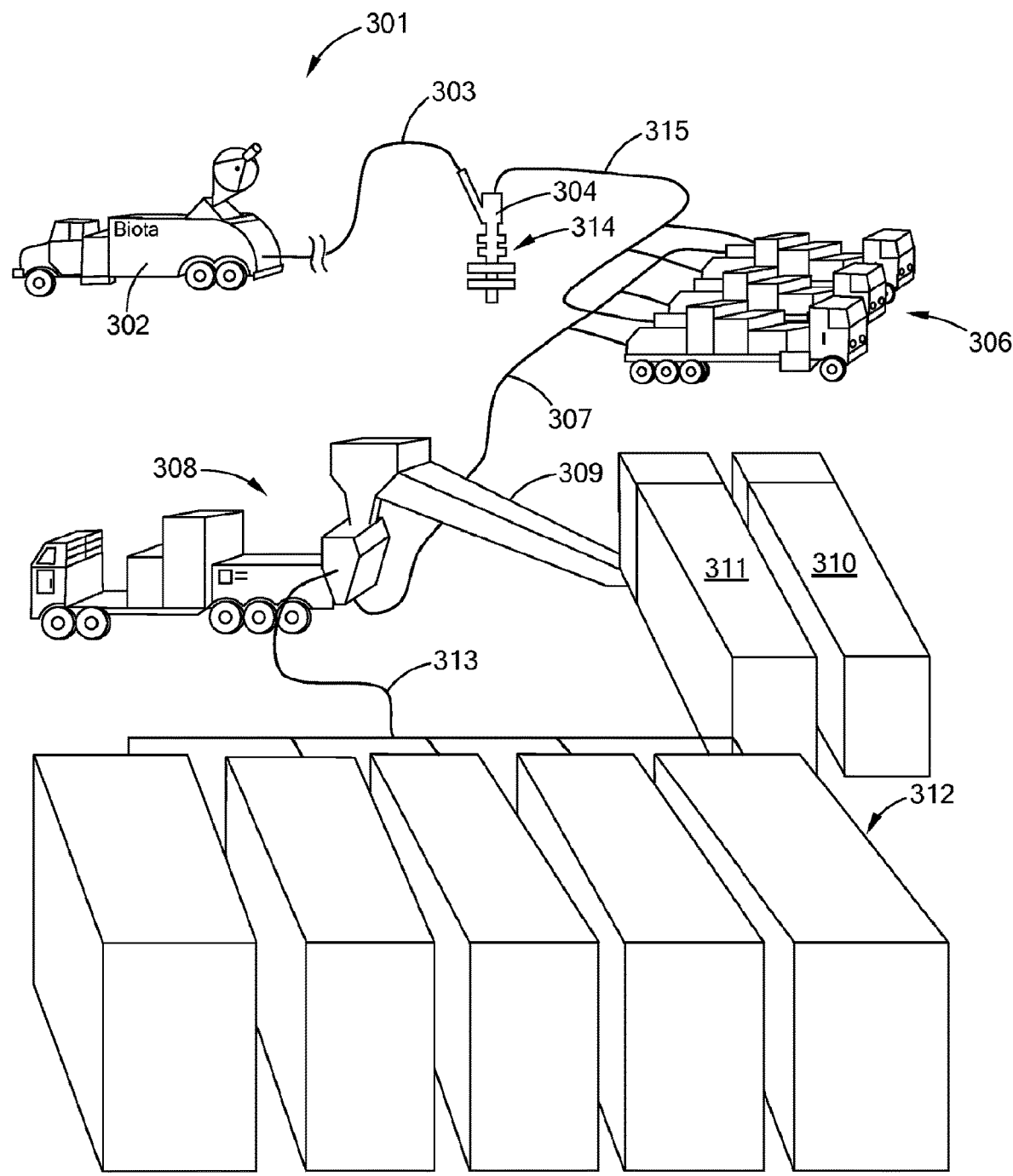
FIG. 3 is a perspective view of an embodiment of an embodiment of a hydraulic fracturing site in accordance with the present inventions.

Turning now to FIG. 3 there is shown a perspective view of a hydraulic fracturing site 301. Thus, positioned near the well head 314 there is a microbiometric field sampling and analysis unit 302, pumping trucks 306, proppant storage containers 310, 311, a proppant feeder assembly 309, a mixing truck 308, and fracturing fluid holding units 312. It is understood that FIG. 3 is an illustration and simplification of a fracturing site. Such sites may have more, different, and other pieces of equipment such as pumps, holding tanks, mixers, and chemical holding units, mixing and addition equipment, lines, valves and transferring equipment, as well as control and monitoring equipment.

The microbiometric field sampling and analysis unit has a sampling line 303, that in the figure is shown as attaching to a sampling port on the well head 314 through an adapter 304. The sampling line 303 may not be used and samples can be collected from various sample points and carried to the field unit 302. Additionally, multiple sample lines may be used. Further the field unit may be at any hydrocarbon exploration or production site, such as the drilling site of the embodiments of FIG. 1 or FIG. 2. Additionally, one or more analysis and sampling field units could be located at an oil field. Thus, the unit(s) may have sampling lines that allow for continuous monitoring of for example conventional information such as pressure or temperature, while taking samples for microbiometric analysis. The field units may also have other lead lines, data line, sample lines and the lake for having data transmitted to unit for compilation, storage, integration and use. Further, the unit can have satellite or other forms of remote wireless communication, including data, capabilities. The presence of the field unit, while in many situations could be preferable, is not required, as samples could be transported to a field lab, regional lab, or another on site or off site facility.

The adapter 314 has a high pressure line 305 that transfers high pressure fracturing fluid from the pump trucks 306 into the well. The fracturing adapter 314 has packers or other pressure managing apparatus. The well head 314 may also have further well control devices associated with it, such as a BOP.

Fracturing fluid from holding units 312 is transferred through lines 313 to mixing truck 308, where proppant from storage containers 310, 311 is feed by assembly 309 and mixed with the fracturing fluid. The fracturing fluid and proppant mixture is the transferred to the pump trucks 306, by line 307, where the pump trucks 306 pump the fracturing fluid into the well by way of line 305.

Samples may be collected from the fracturing fluid as it recovered from the well, or returns from the borehole, for microbiometric analysis.

Further, fluids from a well bore, (e.g., hydrocarbons, oil, gas, washes, secondary recovery fluids, etc.) may be sampled and used for microbiometric analysis in other types of oil filed operations, such as workover, completion and workover and completion activities, which would by way of example include activities that place at or near the completion of drilling a well, activities that take place at or the near the commencement of production from the well, activities that take place on the well when the well is producing or operating well, activities that take place to reopen or reenter an abandoned or plugged well or branch of a well, and would also include for example, perforating, cementing, acidizing, fracturing, pressure testing, the removal of well debris, removal of plugs, insertion or replacement of production tubing, forming windows in casing to drill or complete lateral or branch wellbores, cutting and milling operations in general, insertion of screens, stimulating, cleaning, testing, analyzing and other such activities.

Microbiometric sampling and analysis may also take place during secondary, tertiary and other types of enhanced recovery activities. Including all types of sweeping, flooding, thermal, microbial, polymeric, chemical and other recovery methods know to those of skill in the art or later developed.

The sampling for these oil field activities may take place along the lines of the embodiments of FIGS. 1, 2 and 3, with the use of sample ports at various locations up hole to obtain sample from fluids leaving the borehole, or from holding and separation tanks or stations for such fluids.

Further, coil tubing, cap strings, tube within a tube, and other typed of small tubulars, (that preferable can be inserted into the borehole, casing, production tubing, etc., with little to no effect of flow therein) or other sample lines may be inserted deep within the borehole, or a tubular within the borehole, to a particular and predetermined location to obtain specific samples of materials for microbiometric analysis from those locations.

In the production of natural resources from formations within the earth a well or borehole is drilled into the earth to the location where the natural resource is believed to be located. These natural resources may be a hydrocarbon reservoir, containing water, natural gas, gas condensate, crude oil and combinations of these; it may be a heat source for geothermal energy; or it may be some other natural resource that is located within the ground.

These resource-containing formations may be a few hundred feet, a few thousand feet, or tens of thousands of feet below the surface of the earth, including under the floor of a body of water, e.g., below the sea floor. In addition to being at various depths within the earth, these formations may cover areas of differing sizes, shapes and volumes.

Unfortunately, and generally, when a well is drilled into these formations the natural resources rarely flow into the well at rates, durations and amounts that are economically viable. This problem occurs for several reasons, some of which are well understood, others of which are not as well understood, and some of which may not yet be known.

Among other things, it is these previously unknown and poorly understood reasons for uneconomical flow, sub-par flow and no flow, that the microbiome information obtained and utilized by the present inventions, including real-time, historic, derived and predictive microbiome information can shed light on, and provide ways to avoid, or improve such undesirable flows. Further, the microbiome information can be used to also better understand economically successful flows of hydrocarbons from well, and through this understanding the present inventions will provide derived and more preferably predictive microbiome information to replicate, or otherwise obtain, those flows in other wells and field. Similarly, such microbiome information can be used for well planning and reservoir management purposes.

The ability, or ease, by which the natural resource can flow out off the formation and into the well or production tubing (into and out of, for example, in the case of engineered geothermal well) can generally be understood as the fluid communication between the well and the formation. As this fluid communication is increased several enhancements or benefits may be obtained: the volume or rate of flow (e.g., gals per minute) can increase; the distance within the formation out from the well where the natural resources will flow into the well can be increase (e.g., the volume and area of the formation that can be drained by a single well is increased and it will thus take less total wells to recover the resources from an entire field); the time period when the well is producing resources can be lengthened; the flow rate can be maintained at a higher rate for a longer period of time; the oil/water ratio can increase that results in lower separation and energy costs; and combinations of these and other efficiencies and benefits.

Fluid communication between the formation and the well can be greatly increased by the use of hydraulic fracturing techniques. The first uses of hydraulic fracturing date back to the late 1940s and early 1950s. In general hydraulic fracturing treatments involve forcing fluids down the well and into the formation, where the fluids enter the formation and crack, e.g., force the layers of rock to break apart or fracture. These fractures create channels or flow paths that may have cross sections of a few micron's, to a few millimeters, to several millimeters in size, and potentially larger. The fractures may also extend out from the well in all directions for a few feet, several feet and tens of feet or further. It should be remembered that the longitudinal axis of the well in the reservoir may not be vertical: it may be on an angle (either slopping up or down) or it may be horizontal. For example, in the recovery of shale gas the wells are typically essentially horizontal in the reservoir. The section of the well located within the reservoir, i.e., the section of the formation containing the natural resources, can be called the pay zone. As the fracturing fluids extend out from the well they will capture, e.g., pick up, dissolve (especially if acidizing), and carry along biological and genetic material that is found in the formation and exposed to the fracturing fluid by the breaking open of the rocks. This liquid solution of brine, fracturing fluid, water, other chemicals, and biological and genetic material following a hydraulic fracturing operation is known as "Flowback".

Typical fluid volumes in a propped fracturing treatment of a formation in general can range from a few thousand to a few million gallons. Proppant volumes can approach several thousand cubic feet. In general the objective of a proppant fracturing is to have uniform proppant distribution. In this manner a uniformly conductive fracture along the wellbore height and fracture half-length can be provided.

The fluids used to perform hydraulic fracture can range from very simple, e.g., water, to very complex. Additionally, these fluids, e.g., fracing fluids or fracturing fluids, typically carry with them proppants. Proppants are small particles, e.g., grains of sand, that are flowed into the fractures and hold, e.g., "prop" or hold open the fractures when the pressure of the fracturing fluid is reduced and the fluid is removed to allow the resource, e.g., hydrocarbons, to flow into the well. In this manner the proppants hold open the fractures, keeping the channels open so that the hydrocarbons can more readily flow into the well. Additionally, the fractures greatly increase the surface area from which the hydrocarbons can flow into the well.

The composition of the fluid, the characteristics of the proppant, the amount of proppant, the pressures and volumes of fluids used, the number of times, e.g., stages, when the fluid is forced into the formation, and combinations and variations of these and other factors may be preselected and predetermined for specific fracturing jobs, based upon the microbiome information, including real-time, historic, derived and predictive microbiome information alone or more preferably in conjunction with information about the formation, geology, perforation type, nature and characteristics of the natural resource, formation pressure, and other non-microbiome data points, things or information.

The fluids used to perform hydraulic fracture can range from very simple, e.g., water, to very complex. Additionally, these fluids, e.g., fracing fluids or fracturing fluids, typically carry with them proppants; but not in all cases, e.g., when fracing carbonate formations with acids. Proppants are small particles, e.g., grains of sand, aluminum shot, sintered bauxite, ceramic beads, resin coated sand or ceramics, that are flowed into the fractures and hold, e.g., "prop" or hold open the fractures when the pressure of the fracturing fluid is reduced and the fluid is removed to allow the resource, e.g., hydrocarbons, to flow into the well. In this manner the proppants hold open the fractures, keeping the channels open so that the hydrocarbons can more readily flow into the well. Additionally, the fractures greatly increase the surface area from which the hydrocarbons can flow into the well. Typically fracturing fluids, used for example in shale gas stimulations, consist primarily of water but also have other materials in them. The number of other materials, e.g., chemical additives used in a typical fracture treatment varies depending on the conditions of the specific well being fractured. Generally, for shale gas, a typical fracture treatment will use very low concentrations of from about 2 to about 15 additives. Each component serves a specific, engineered purpose to meet anticipated well and formation conditions.

Generally the predominant fluids being used for fracture treatments in the shale plays are water-based fracturing fluids mixed with friction-reducing additives, e.g., slick water, or slick water fracs. Overall the concentration of additives in most slick water fracturing fluids is generally about 0.5% to 2% with water making up 98% to 99.5%. The addition of friction reducers allows fracturing fluids and proppant to be pumped to the target zone at a higher rate and reduced pressure than if water alone were used.

In addition to friction reducers, other such additives may be, for example, biocides to prevent microorganism growth and to reduce biofouling of the fractures; oxygen scavengers and other stabilizers to prevent corrosion of metal pipes; and acids that are used to remove drilling mud damage within the near-wellbore.

Further these chemicals and additives could be one or more of the following, and may have the following uses or address the following needs: diluted Acid (≈15%), e.g., hydrochloric acid or muriatic acid, which may help dissolve minerals and initiate cracks in the rock; a biocide, e.g., glutaraldehyde, which eliminates bacteria in the water that produce corrosive byproducts; a breaker, e.g., ammonium persulfate, which allows a delayed break down of the gel polymer chains; a corrosion inhibitor, e.g., N,N-dimethyl formamide, which prevents the corrosion of pipes and equipment; a crosslinker, e.g., borate salts, which maintains fluid viscosity as temperature increases; a friction reducer; e.g., polyacrylamide or mineral oil, which minimizes friction between the fluid and the pipe; guar gum or hydroxyethyl cellulose, which thickens the water in order to help suspend the proppant; an iron control, e.g., citric acid, which prevents precipitation of metal oxides; potassium chloride, which creates a brine carrier fluid; an oxygen scavenger, e.g., ammonium bisulfite, which removes oxygen from the water to reduce corrosion; a pH adjuster or buffering agent, e.g., sodium or potassium carbonate, which helps to maintain the effectiveness of other additives, such as, e.g., the crosslinker; scale inhibitor, e.g., ethylene glycol, which prevents scale deposits in pipes and equipment; and a surfactant, e.g., isopropanol, which is used to increase the viscosity of the fracture fluid.

Generally and for example, in ascertaining microbiome information the selection and sequencing of particular regions or portions of genetic or genetically encoded materials may be used, including for example, the SSU rRNA gene (16S or 18S), the LSU rRNA gene (23S or 28S), the ITS in the rRNA operon, cpn60, and various other segments consisting of base pairs, peptides or polysaccharides for use in characterizing the microbial community and the relationships among its constituents.

Figure 16:
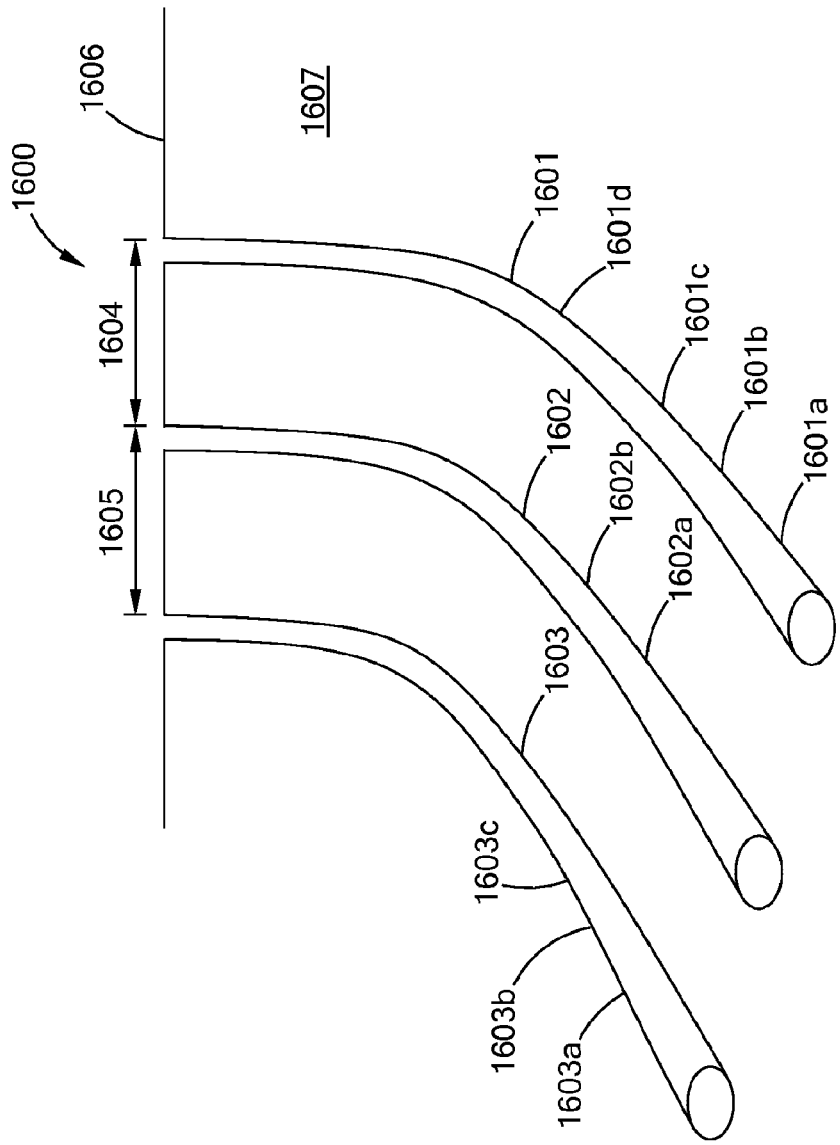
FIG. 16 is a cross sectional perspective view of an embodiment of an oil field in accordance with the present inventions.

Turning to FIG. 16, there is shown a schematic view of a perspective cross section of an oil field 1600. The of field 1600 has a surface of the earth 1606 and a formation 1607 below the surface of the earth 1606. The oil field 1600 has three wells, 1601, 1602, 1603, that are producing hydrocarbons, e.g., oil, natural gas, or both. It being understood that the oil field could have less, or more wells, that are producing or not producing.

The wells 1601, 1602, 1603 extend down and into the formation 1607. The wells have zones that are producing hydrocarbons, e.g., production zones. Typically, these zones have been perforated and hydraulically fractured as well as having other completion activities performed on them. Thus, well 1601 has zones 1601a, 1601b, 1601c. Well 1602 has zones 1602a, 1602b. Well 1603 has zones 1603a. 1603b, 1603c, and 1603d. It being understood that a well could have more and less zones, and that they zone can be of varying distance along the borehole.

During planning and production from the well the placement of the zones, closing of zones and opening of new zones is a factor in enhancing the production and efficiency of the well. These factors can in some situations greatly affect the economics of a well and oil field. The present microbiome techniques and analysis can provide information and data, e.g., microbiome finger prints, finger prints, about the well, production, and the performance of specific zones in the well. These finger prints can be used to determine the relative production from a specific zone, and thus for example if a zone needs to be closed, reworked, or a new zone needs to be opened. Further these finger prints can be used to determine and analyze the decline in production. Thus, for example, if the the finger prints shows that all zones are still producing evenly, e.g., there ratio of production from the zones had not materially changed, yet production for the well is declining, it could indicate that a particular treatments, reworking or other activities are need to increase production. The analysis and information from the present microbiome techniques and information can be used to determine whether a decline in production, failure to produce is based upon the formation, or a mechanical, or structure problem with the well, completion activities and both.

The wells 1601, 1602, 1603 have a spacing between them, shown by double arrows 1604, 1605. The analysis and information from the present microbiome techniques and information can be used to determine the optimum spacing for a particular oil field.

Thus, in an embodiment of activities to enhance the production of hydrocarbons from well 1603, microbiome information is obtained from the hydrocarbons being produced, this first microbiome information is obtained, e.g., the sample is obtained, at time $t_1$ from hydrocarbons produced from a well. The present microbiome evaluations are performed on this sample and information, e.g., a finger print, for each production zone 1603a, 1603b, 1603c, of the well 1603 at time $t_1$. At a later point in time, a second microbiome information from the well 1603 is obtained from a sample of hydrocarbons produced from the well, the second sample is taken at time $t_2$. Time $t_1$ and $t_2$ can be space in time by one day, two days, a week, a month, six months or other time period. The time $t_1$, $t_2$, $t_n$ can be based on changes in production, thus the sampling is driven by an event. The sampling may also be part of, and preferably, is part of a route sample and microbiome monitoring and analysis for the well. In this manner a substantial history of information and data can be built for the well, and the oil field.

In this manner, the microbiome information that is used can be historic microbiome information, real time microbiome information, derived microbiome information, predictive microbiome information and combinations and variations of these. The historic microbiome information, in embodiments can be from the Earth Microbiome Project, the Human Microbiome Project, American Gut, GreenGenes, the Ribosomal Database Project, the International Nucleotide Sequence Database Collaboration (INSDC), American Gut, stored real time data from the well, and combinations and variations of these.

Preferably, in embodiments of this evaluation of field 1600 and the wells 1601, 1602, 1603 the evaluation links or relates microbiome information and data with industrial setting, e.g., factors, information about the well, such as for example GPS data, location data, system component identification, subsystem component identification, pump station true vertical depth of a well, pH, measured depth of a well, processing stage, geological parameter, formation permeability, viscosity, porosity, pressure, flow, temperature, and combinations and variations of these and other other information.

Thus, by way of example the evaluations can provide comparison data over time, e.g., directing information, that will lead to, support, or form a basis in whole or in part for well, and filed activities, such as workover and completion activities, stimulation activities, well placement, well shut down, well shut in, zone shut down, reworking a well, reworking a zone, refracturing a well, well spacing, drilling a new well and combinations and variations of these and exploration and production activities.

In other embodiments the data and information obtained for these analysis and in particular these analysis over time, e.g., comparison data, directing information, predictive, derived, historic and combinations and variations of these and other types of data for or relating to: oil saturation and permeability; wettability; oil viscosity, temperature, pressure, porosity, oil or water saturation, and compressibility; subsurface flow communication and reservoir connectivity; propensity for producing oil versus gas; production zone that improves vertical and aerial conformance; chemical and physical properties of the treatment and produced fluids; environmental impact of the hydraulic fracturing; being transformed into a high resolution subsurface geologic map of a production zone; oil-water contact levels in a well; likelihood of oil coning or cusping; commercial valuation of new leases or the commercial valuation of existing leases; the recovery factor of the existing and potential future wells as well as the effectiveness of any enhanced oil recovery techniques; existence of $H_2S$ in existing and potential future wells; existence of current or future potential leaks the oil pipelines; existence or future potential reservoirs; oil saturation and permeability; subsurface flow communication and reservoir connectivity; and combinations and variations of these and other factors.

In an embodiment of the present activities the monitoring of and production of hydrocarbons from a well can be conducted by obtaining a microbiome information from hydrocarbons produced from a well having a plurality of production zones; and, performing an evaluation on the microbiome information. This analysis provides information, e.g., a microbiome finger print that is produced and specific form a plurality of production zones. Thus, information about each production zone and relative information about all of the production zones can be obtained. For example the relative production rates from each zone can be determined. Preferably, this multiple zone information can be obtained from a single sample of hydrocarbons from the well, multiple samples may be used as well.

In an embodiment a method of enhancing the production of hydrocarbons from an oil field microbiome information is obtained from hydrocarbons produced from a first well, e.g., 1603, in an oil field, e.g., 1600, having a plurality of wells at time $t_1$. Microbiome information is obtained from hydrocarbons produced from a second well, e.g., 1602, in field 1600 at about time $t_2$. The times $t_1$ and $t_2$ can be the same or different time or day, and can extend over longer and shorter periods of time. There can be more samples taken of any number of times and time periods. The present evaluations and techniques are performed including for example a relationship based processing having a related genetic material component and an industrial setting component, and also for example including a bioinformatics stage, which produces a microbiome finger print for the first well 1603 at time $t_1$, and the second well 1602 at time $t_2$. This process can than be repeated for the wells over time $t_n$ to $t_{n+1}$ and for other wells as well. The information, e.g. finger prints, from these processes are analyzed and then based at least in part on the analysis an activity in the oil field is performed.

In a preferred embodiment the analysis of the fluid from well 1603 includes for example extracting material comprising genetic material selected from the group consisting of a SSU rRNA gene 16S, SSU rRNA gene 18S, LSU rRNA gene 23S, LSU rRNA 28S, ITS in the rRNA operon, and ITS in the rRNA cpn60. In a preferred embodiment the microbiome information can include for example information obtained from variable regions of the 16S rRNA. This variable regions may be for example selected from the group consisting of V2, V4, and V6.

The information obtained from the present analysis, e.g., directing information, can be used to direct activities in the oil field, such as for example: placing a plug, creating a brank, side tracking, determining the depth of the borehole, a casing plan, determining the location of perforations, determining the placement of perforations, following a lateral hydrocarbon containing formation, and secondary recovery from the borehole.

In general, an embodiment of a method of the present invention may include one or more of the following steps which may be conducted in various orders: sample preparation including obtaining the sample at the designated location, and manipulating the sample; extraction of the genetic material and other biomolecules from the microbial communities in the sample; preparation of libraries with identifiers such as an appropriate barcode such as DNA libraries, metabolite libraries, and protein libraries of the material; sequence elucidation of the material (including, for example, DNA, RNA, and protein) of the microbial communities in the sample; processing and analysis of the sequencing and potentially other molecular data; and exploitation of the information for industrial uses.

Figure 4:
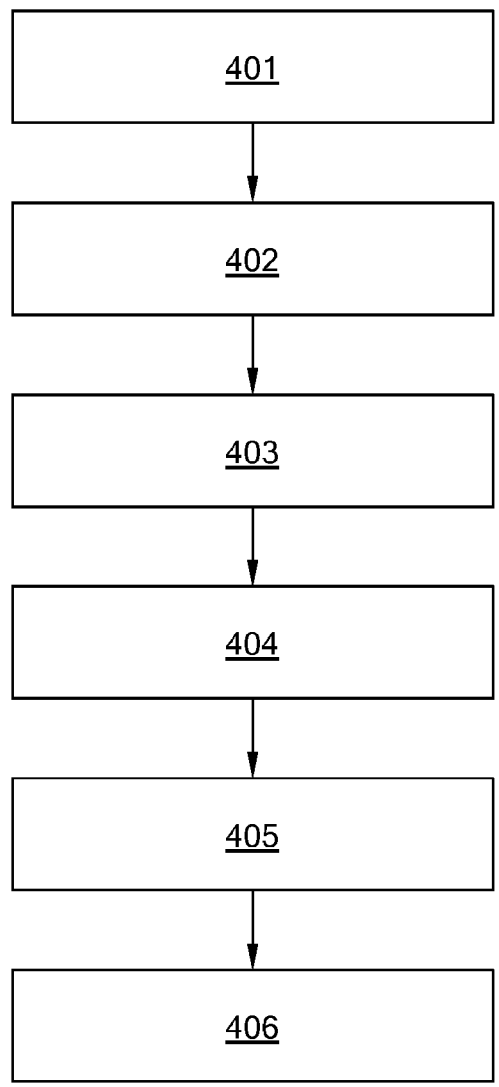
FIG. 4 is a flow chart of an embodiment of a process in accordance with the present inventions.

For example, turning to FIG. 4, there is shown an example of a flowchart setting forth various embodiments of these processes applied across various industrial settings. Thus, sampling 401 is performed. The sampling may be for example from an agricultural, petroleum, mineral, food, surfaces, air, water, human source or subject. The samples can include for example solid samples such as soil, sediment, rock, metal counters, and food. The samples can include for example liquid samples such as petroleum, surface water, and subsurface water. The samples can include for example complex fluid and fluid mixtures such as drilling mud, and fracturing fluid. The sample once obtained has the genetic material isolated or obtained from the sample 402, which for example can be DNA, RNA, proteins and fragments of these.

A library is prepared 403 from the genetic material. In this stage of the process the library can be prepared by use of amplification, shotgun, whole molecule techniques among others. Additionally, amplification to add adapters for sequencing, and barcoding for sequences can be preformed. Shotgun by sonication, enzymatic cleavage may be performed. Whole molecules can also be sued to sequence all DNA in a sample.

Sequencing 404 is performed. Preferably, the sequencing is with a high-throughput system, such as for example 454, lllunina, PacBio, or IonTorrent.

Sequence analysis 405 is prepared. This analysis preferably can be performed using tools such as QIIME Analysis Pipeline, Machine learning, and UniFrac. Preferably, there is assigned a sequence to the sample via barcode, for among other things quality control of sequence data.

The analysis 405, is utilized in an industrial application 406. The applications can include for example, cosmetics, agriculture, animal husbandry, pharmaceuticals, space exploration, oil, petroleum, geothermal, alternative energy, and production in factories.

Figure 5:
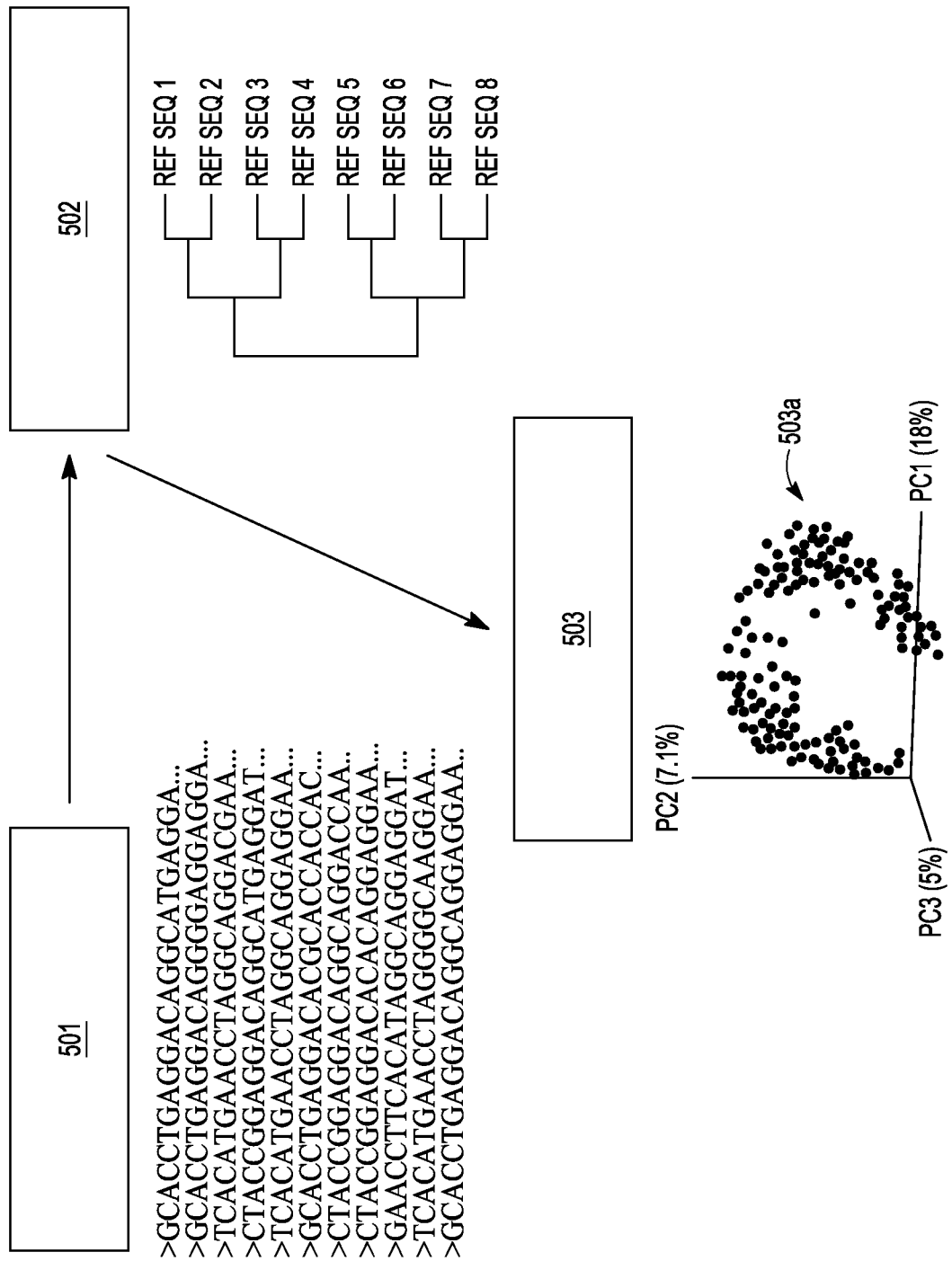
FIG. 5 is a flow chart of an embodiment of a process in accordance with the present inventions.

Turning to FIG. 5, there is illustrated an embodiment of the general processing and analysis of the biomolecular material, which is step 405 of FIG. 4. Thus as generally shown in FIG. 5, and as explained in greater detail below, generally, the processing and analysis further involves matching 501 the sequences to the samples, aligning the sequences to each other, and using the aligned sequences to build a phylogenetic tree 502, further distilling the data to form an n-dimensional plot and then a two or three dimensional plot or other graphical displays, including displays of the results of machine learning and multivariate statistical routines, and using the two or three-dimensional plot or other graphical displays to visualize patterns of the microbial communities in a particular sample over time 503.

Although HMI-type presentation of this information is presently preferred, it should be understood that such plots may be communicated directly to a computational means such as a large computer or computing cluster for performing further analysis to provide predictive information. Thus the matched sequence samples 501 would be an example of real-time or historic microbiome information, the phylogenetic tree 502 would be an example of derived microbiome information, and portions of the graphical displays 203 which have derived microbial information combined with other data would be an example of predictive microbiome information. Thus, for example, if the information 503 related to exploration and production of hydrocarbons a uniquely colored section 503a (grey scale used for purposes of patent figures) would indicate areas of higher oil saturation and thus predictive information of where greater hydrocarbon production would occur. It should be understood that the information section 503, if not otherwise predictive of future processes or activities, would merely be derived data.

Generally, a phylum is a group of organisms at the formal taxonomic level of Phylum based on sequence identity, physiology, and other such characteristics. There are approximately fifty bacterial phyla, which include Actinobacteria, Protecbacteria, and Firmicutes. Phylum is the classification that is a level below Kingdom, in terms of classifications of organisms. For example, or *E. coli* the taxonomy string is Kingdom: Bacteria; Phylum: Proteobacteria; Class: Gammaproteobacteria; Order: Enterobacteriales; Family: Enterobacteriaceae; Genus: *Escherichia*; and Species: *coli*.

Generally, phylogeny refers to the evolutionary relationship between a set of organisms. This relationship can be based on morphology, biochemical features, and/or nucleic acid (DNA or RNA) sequence. One can measure the changes in gene sequences and use that as a molecular clock to determine how closely or distantly the sequences, and hence the organisms that contain them, are related.

Generally, different methods of microbiotic classification exist. Two general methods are that of phylotypes whereby sequences are classified upon reference taxonomic outlines to classify sequences to taxonomic bins; and that of operational taxonomic unit ("OTU") based methods where sequences are classified based on their similarity to each other (for instance an 97% similarity OTUs are roughly analogous to "species" classification). Phylotypes can also be defined at other taxonomic levels and these other levels are sometimes critical for identifying microbial community features relevant to a specific analysis. Because short DNA, RNA or protein sequences ("reads") can be used, these sequences may not accurately identify many organisms to the level of species, or even strain (the most detailed level of phylogenetic resolution, which is sometimes important because different strains can have different molecular functions). In cases where a "phylotype" matches a sequence or group of sequences from a known organism in the databases, it can used to say that a particular sequence is from an organism like, for example, *E. coli*.

Generally, a taxon is a group of organisms at any level of taxonomic classification. Here, taxon (plural: taxa) is a catchall term used in order to obviate the usage of the organism names repeatedly and to provide generality across taxonomic levels.

Microbial community diversity and composition may vary considerably across industrial environments and settings, and the present inventions link and or correlate these changes to biotic or abiotic factors and other factors and conditions in the industrial environment to create derived and predictive information. Thus these patterns of microbial communities for example geological patterns of microbial communities or patterns of microbial communities in an industrial system (microbiosystem metrics) which are determined by the present invention can give rise to predictive information for use in the industrial setting.

Examinations of microbial populations, e.g., a census, may provide insights into the physiologies, environmental tolerances, and ecological strategies of microbial taxa, particularly those taxa which are difficult to culture and that often dominate in natural environments. Thus, this type of derived data is utilized in combination with other data in order to form predictive information.

Microbes are diverse, ubiquitous, and abundant, yet their population patterns and the factors driving these patterns were prior to the present inventions not readily understood in industrial settings and thus it is believed never effectively used for the purposes for ascertaining predictive information. Microorganisms, just like macroorganisms (i.e., plants and animals), exhibit no single shared population pattern. The specific population patterns shown by microorganisms are variable and depend on a number of factors, including, the degree of phylogenetic resolution at which the communities are examined (e.g., *Escherichia*), the taxonomic group in question, the specific genes and metabolic capabilities that characterize the taxon, and the taxon's interactions with members of other taxa. Thus, such population patterns can be determined in industrial settings and utilized as derived data for the purposes of ascertaining predictive information.

However, for certain environments, common patterns may emerge if the biogeography (e.g., microbial populations for example as determined from a census), of that particular environment is specifically examined. In particular, the structure and diversity of soil bacterial communities have been found to be closely related to soil environmental characteristics such as soil pH. A comprehensive assessment of the biogeographical patterns of, for example, soil bacterial communities requires 1) surveying individual communities at a reasonable level of phylogenetic detail (depth), and 2) examining a sufficiently large number of samples to assess spatial patterns (breadth). The studies of biogeographical patterns is not limited to soil, and will be extended to other environments, including but not limited to, any part of a living organisms, bodies of water, ice, the atmosphere, energy sources, factories, laboratories, farms, processing plants, hospitals, and other locations, systems and areas.

It should be understood that the use of headings in this specification is for the purpose of clarity, and are not limiting in any way, Thus, the processes and disclosures described under a heading should be read in context with the entirely of this specification, including the various examples. The use of headings in this specification should not limit the scope of protection afford the present inventions.

Generally, samples will be collected in a manner ensuring that microbes from the target source are the most numerous in the samples while minimizing the contamination of the sample by the storage container, sample collection device, the sample collector, other target or other non-target sources that may introduce microbes into the sample from the target source. Further, samples will be collected in a manner to ensure the target source is accurately represented by single or multiple samples at an appropriate depth (if applicable) to meet the needs of the microbiome analysis, or with known reference controls for possible sources of contamination that can be subtracted by computational analysis. Precautions should be taken to minimize sample degradation during shipping by using commercially available liquids, dry ice or other freezing methods for the duration of transit. If appropriate tests are completed, to show that there is no impact of shipping method or temperature, samples may also be shipped at ambient temperature.

Preferably, precautions, adjustments and general biological material sampling techniques and most preferably best practices, can be taken or included in the sample collection methodology to provided greater assurances that the collected samples accurately represent the microbiome from oil and gas wells. As noted in this specification, the collection containers must be suitable for molecular biological sample recovery, environmental sample recovery and combinations and variations of these. In general, similar care must be taken when sampling well material. Many microbial communities residing in oil and gas fields may be of low biomass (e.g., relatively few organisms are present per unit volume or unit of mass) the introduction of organisms from non-target sources as well as changes in environment may become issues, and in some situations are important considerations, in managing the resulting data. For instance, samples collected by untrained individuals may result in the introduction of microbes from sources including, but not limited to, those residing on human skin, surface soils or deeper sediments, drilling mud and injection water. Mitigating the introduction of these microbes into the target samples can be effectively accomplished by the use of personal protective equipment including, but not limited to, disposable examination gloves, surgical type face masks and sterile collection containers when each new type of sample from the well or at the drill site is collected.

The use of external materials used to drill and produce hydrocarbons from a well is inevitable and these sources should be included in a thorough assessment of subsurface microbial communities. Liquids such as water or combinations of water and other liquids, proppant-loaded slurries, acid solutions can be sampled to identify microbes which reside in these sources so they are not confused with microbes of the sub surface. Similar care as noted above can also be taken when sampling these sources prior to their injection into the well. The use of personal protective equipment to limit contact between the sample collector and the sample in many cases will be the most preferred practice due to low biomass in many of these sources. The use of disposable examination gloves cleaned with alcohol or by other means, for instance, during the collection of a similar sample type or a group of samples from the same source can aid in mitigate the introduction of non-target microbes. New gloves and other personal protective equipment should be changed for each new or different sample source.

Managing potential sources of non-target microbes can also be accomplished by monitoring the microbial content of drilling mud (oil or water based), injection water, well cuttings, flowback or produced water, formation fluid (oil and water mixes), and oil produced from the well, among others. Those sources which are injected into the well either for exploration or production of hydrocarbons should be sampled by trained personnel wearing appropriate personal protective equipment and collected into containers as described above prior to introduction into the bore hole or production well. Preferably, samples from each potential source should be collected as close to the well head (as inflow or outflow) as possible to identify the potential contribution of each source to the target and/or core microbial community.

For example, samples can be collected in sterile, DNA/DNase/RNA/RNase-free primary containers with leak resistant caps or lids and placed in a second leak resistant vessel to limit any leakage during transport. Appropriate primary containers can include any plastic container with a tight fitting lid or cap that is suitable for work in microbiology or molecular biology considered to be sterile and free of microbial DNA (or have as little as possible) at minimum. (However, it should be noted that human DNA contamination, depending upon the markers or specific type microbe that is being looked at may not present a problem.) The primary container can also be comprised of metal, clay, earthenware, fabric, glass, plastic, wood, etc. So long as the container may be sterilized and tested to ensure that it is ideally DNADNase/RNA/RNase-free (or at least contains levels of nucleic acid much lower than the biomass to be studied, and low enough concentration of nuclease that the nucleic acids collected are not degraded), and can be closed with a tight-fitting and leak resistant lid, cap or top, then it can be used as a primary container.

The primary container with the sample can then be placed into a secondary container, if appropriate. Appropriate secondary containers can include plastic screw top vessels with tight fitting lids or caps and plastic bags such as freezer-grade zip-top type bags. The secondary container can also be comprised of metal, clay, earthenware, fabric, glass, plastic, wood, etc. So long as the container can be closed or sealed with a tight-fitting and leak resistant lid, cap or top, then it can be used as a secondary container. The secondary container can also form a seal on itself or it can be fastened shut for leak resistance.

The samples should generally be collected with minimal contact between the target sample and the sample collector to minimize contamination. The sample collector, if human, should generally collect the target sample using gloves or other barrier methods to reduce contamination of the samples with microbes from the skin as discussed above. The sample can also be collected with instruments that have been cleaned and/or sterilized. The sample collector, if machine, should be cleaned and sterilized with UV light and/or by chemical means prior to each sample collection. If the machine sample collector requires any maintenance from a human or another machine, the machine sample collector must be additionally subjected to cleaning prior to collecting any samples.

Thus, for example, the outflow of mud return line (120/121) before the mud is deposited into the mud pit (118a—preferably at asterisk labeled 214a in FIG. 2) is collected, because preferably the sample should be as fresh as can be sample from the well. Likewise, the sample may also be collected, but then kept on ice, or frozen (and/or kept ambient—if deemed acceptable to processes) between sampling and shipping. The sample is drawn off through valve placed at 214a into sterile container by trained personnel wearing sterile exam gloves. The container is filled to a predetermined volume with well outflow material and a preservative may or may not be added, the sample may be frozen immediately, shipped and combinations and variations of these. For example the sample container can be filled to a predetermined volume with well outflow material, a preservative added and the sample is cooled and shipped later. Automatic sampling can be accomplished by diverter valve placed at 214*a* into rack that moves sample collection tubes (with or without preservative added) to collect samples across given time span or to collect any samples.

Monitoring microbial communities from the sub surface during a hydraulic fracturing operation can consist of samples taken from the high pressure inflow line (FIG. 3, element 315), preferably as close to the frac adapter (element 304) as possible and from the umbilical (element 303) into containers described above. The microbial content of hydraulic fracturing fluid constituents (e.g., water, sand, inorganic and organic chemicals, acids, bases, etc.) can also be monitored prior to their mixing and injection into the borehole. Pressure reducers/valves may need to be installed to collect samples for analysis on element 315. Outflow from the bore hole can be transmitted to a mobile analysis unit via element 303 for immediate analysis or preserved and shipped to lab for analysis.

Tracers for insertion into the well and then monitoring upon recovery from the well may also be employed. Further, specific samples may be taken, by way of an ESP or other pump type, or tube placed at a specific location in a well to monitor activity there.

Two broad classes of control samples, among others, preferably should be collected to monitor the introduction of microbes into the target prior to the initiation of drilling or mixing of chemicals. The first class of samples are to monitor the solids and liquids injected, detailed above, into the borehole or well including individual components of hydraulic fracturing fluid, water, sand, inorganic and organic chemicals or any other solid or liquid material that is injected or is collected from an exploratory or production well. The second class of control samples should be derived from local environment which can include but not be limited to; surface or subsurface soils, surface or subsurface water, well tailings, hoses, holding tanks, mixing tanks, pumps, and well casings. Control samples of liquids or free-flowing solids (e.g. sand, bentonite, surface soil or well tailings) can be collected in appropriate containers (e.g., as described above) and preserved if necessary. Control samples from surfaces such as pumps, well casings, and hoses may be collected on sterile swabs suitable for bacterial specimen collection and preserved if necessary.

For manual sampling, the sampling kit could include but not be limited to; collection containers, secondary containers, personal protective equipment, preservative, indelible marking pens or pre-printed labels and a shipping container. The number of collection containers and other components should preferably fit neatly into the shipping container and if necessary multiple sampling kits should be used when many samples are to be collected. Collection on sterile swabs can be done directly from surfaces or the swab submerged in samples collected in appropriate sterile sampling containers described above.

Automated sampling can be done at specified, regular intervals using an automated sampling device attached to a diverter line that attaches to a hose, tube, pipe, or tank carrying the material to be sampled. The diverter line preferably should be changed periodically to minimize the buildup of microbial biofilms, which may add an additional source of contamination onto the target sample and/or source of data regarding current or historical conditions of the fluid flowing through the diverter. Samples should be collected in sterile containers that may or may not contain a known volume of preservative. Once collected, the samples should be removed from the automated sampler and stored or shipped for analysis.

After the sample is collected and placed in a primary and secondary container, the samples will be preserved. One method of preservation is by freezing on dry ice or liquid nitrogen to between 4° C. to −80° C. Another method of preservation is the addition of preservatives such as RNAstable®, LifeGuard™ or another commercial preservative, and following the respective instructions. So long as the preservation method will allow for the microbial nucleic acid to remain stable upon storage and upon later usage, then the method can be used.

The samples preferably should be shipped in an expedient method to the testing facility. In another embodiment, the testing of the sample can be done on location. The sample testing should be performed within a time period before there is substantial degradation of the microbial material within the sample or such that the microbial fraction changes due to the alteration in the local environment (due to, for instance, the sample container). So long as the sample remains preserved and there is no substantial degradation of the microbial material any method of transport in a reasonable period of time is sufficient.

Tracers, may also be added to the inflow of a sampling catchment to identify the organisms present in the system that are not from the target source. The tracer can be microorganisms or anything that will allow for analysis of the flow path. For example, in an oil setting, a tracer can be used to calibrate the effectiveness of a flooding operation (water, $CO_2$, chemical, steam, etc.). The tracer can be used to determine factors such as the amount of injection fluid flowing through each zone at the production wellbore and the path of the injection fluid flow from the injection site to the production bore. Fixed and stained bacteria could be added to any fluid that is injected into the well. Fixed cells are dead and thus will not impact the metabolic activity of the target microbial communities. Under circumstances in which there are changes in the microbial tracers, using high throughput sequencing methods and analysis, like that included in this specification, the ability to account for these changes exists. Bacterial stains include but are not limited to DAPI (4',6-diamidino-2-phenylindole), SYBR Green, PicoGreen and bacteria stained with these dyes would indicate which injection fluid is found along the fractures or the reservoir. Further, tracers such as potassium bromide may be added to any fluid to track the flow of through the fractures or reservoir.

DNA/RNA Extraction

The extraction of genetic material will be performed using methods with the ability to separate nucleic acids from other, unwanted cellular and sample matter in a way to make the genetic material suitable for amplification, library construction and combinations and variations of these. For example, this can be done with methods including one or more of the following, but not limited to, mechanical disruption such as bead beating, sonicating, freezing and thawing cycles; chemical disruption by detergents, acids, bases, and enzymes; other organic or inorganic chemicals. Isolation of the genetic material can be done through methods including one or more of the following, but not limited to, binding and elution from silica matrices, washing and precipitation by organic or inorganic chemicals, electroelution or electrophoresis or other methods capable of isolating genetic material. Furthermore, due to the specific physical or chemical properties of a sample, for example heavy clay or humus, extra methods such as 'pre-treatments' could be used to aid in the isolation of genetic material.

Extractions will be done in an environment suitable to exclude microbes residing in the air or on other surfaces in the work area where the extraction is taking place. Care will be taken to ensure that all work surfaces and instruments are cleaned to remove unwanted microbes, nucleases and genetic material. Cleaning work surfaces and instruments can include, but is not limited to, spraying and/or wiping surfaces with a chlorine bleach solution, commercially available liquids such as DNAse AWAY™ or RNase AWAY™ or similar substances that are acceptable in routine decontamination of molecular biology work areas. Furthermore, aerosol barrier pipette tips used in manual, semi-automated or automated extraction process will be used to limit transfer of genetic material between instruments and samples.

Controls for Reagents for extractions and/or primary containers (when appropriate) will be tested to ensure they are free of genetic material. Testing of the reagents includes, but is not limited to performing extraction "blanks" where only the reagents are used in the extraction procedure. When necessary primary collection containers may also be tested for the presence of genetic material serving as one type of 'negative control' in PCR of the genetic material of the sample. In either case, testing the blank or negative control may be accomplished, but not limited to, spectrophotometric, fluorometric, electrophoretic, PCR or other assays capable of detecting genetic material. followed by testing the blank for the presence of genetic material by, but not limited to, spectrophotometric, fluorometric, electrophoretic, PCR or other assays capable of detecting genetic material.

The mobile extraction lab should preferably contain DNAse/RNase AWAY, paper towels, pipettors, aerosol barrier pipet Ups, centrifuge, PCR enclosure, reagents, personal protective equipment, vacuum pump, consumables (tubes, plates, etc), ice machine, water bath or heated dry block, and waste disposal vessels enclosed in a container in which filtered air creates positive pressure. Further pre-assembled extraction 'packs' containing clean pipettors, aerosol barrier pipet tips, reagents, personal protective equipment, consumables (tubes, plates, etc) and waste disposal vessels can be shipped to sites where a mobile lab is located. A full-service mobile lab, preferably, should contain the above items in addition to, for example, PCR primers, PCR master mix, thermocyclers, liquid-handling robot, 96 well fluorometer, high sensitivity DNA assay apparatus such as qBit, a Agilent BioAnalyzer, electrophoresis equipment, DNA sequencer and necessary compute resources or high-speed network link to such compute resources. The lab preferably should also contain all reagents and kits necessary to perform genetic extractions and any necessary laboratory tests. Generally, the extraction can be one of the more critical aspects of sample prep that will require skilled labor and potential training.

The methods, techniques and systems described herein can be useful in a plethora of oil field settings. The scope of the information obtained can vary, based on the type of goal to be obtained. For example, an embodiment of the methods can be applied on a macro scale, such as, sampling and analysis from all wells through out the world. Embodiments of the methods can also be applied on a regional scale, for example, sampling and analysis of wells in a region of the United States, or for a particular formation or field. Further, embodiments of the method can be applied on a local scale, for example, sampling and analysis of a lease area. Further, the method can be applied on a well-based scale, for example, sampling and analysis of a producing well, or particular producing wells in a field. The following examples are provided to illustrate various devices, tools, configurations and activities. These examples are for illustrative purposes, and should not be viewed as limiting, and do not otherwise limit, the scope of the present inventions.

Example 1—Collection and Extraction of DNA

Specific examination of microbial biogeography requires collection of samples, using the above general guidelines for sample containers, at a predetermined depth using a device to obtain a roughly equivalent amount of sample from each sampling location at the target location(s). The number of samples to be collected will be determined by the spatial and temporal scales over which microbial communities vary, the effect size of different factors that affect the community, and the range of conditions that need to be tested to ensure that the relevant diversity of the microbial communities is adequately represented in the samples. Further, samples can be analyzed individually or combined to produce a composite sample to represent the target sites. Samples should be preserved by storing on ice and shaded from sunlight while in transit from the field. Samples can remain at approximately 4° C. for 1-3 days for shipping or can be frozen at −20° C. or −80° C. and shipped on dry ice. If and only if, it is deemed appropriate samples can also be shipped at ambient temperature. Samples frozen at −80° C. can be stored indefinitely. DNA can be extracted by any method suitable for isolating the genetic material from the soil, oil, water, mixtures, and combinations and variations of these.

Example 2—Crude Oil Sample From Production Well

Triplicate samples from three wells each from three different possible formations at three time points (t0, t0 plus one week, and t0 plus one month) will be collected. The wells will be matched (as much as is possible) for geological features including production zone and distance between the surface and the oil/water interface, and physical and chemical features of the fluid (e.g., temperature, viscosity, pressure, and hydrocarbon composition). One sample from the corresponding collection tanks will be gathered when each of these samples are collected. These will be known as the "baseline" samples.

Triplicate samples will also be collected from the wellhead of six wells (n=18), three each from two different single-production-zone wells. These wells will preferably may be matched with the wells sampled for the baseline samples, but thought to be from different production zones. Triplicate samples will be collected from the wellheads of five wells, each producing from different, known combinations of production zones (n=15).

Personal protective equipment will be donned to reduce contamination as described above. Oil samples will be collected in appropriate sterile 50 ml conical tubes containing (which could contain a preservative if deemed necessary, such as 10 ml RNAlater, DNAlater or other similar type of material) and then placed in secondary containment to prevent leakage during transit and preserve the microbes in the sample.

Once the sample(s) are received at an analysis facility or a mobile analysis station, DNA extractions are perfumed. For example for single extractions: (Step 1) 135-150 µl (this amount should be calibrated and optimized based on the numbers of microorganisms contained in the samples and the kit or protocol used) sample will be placed in a Bead tube of the DNA extraction kit. (Step 2) 60 µL of Solution C1 will then be added to the sample in the Bead Tube and heated to 65° C. for 10 minutes. (Step 3) The sample will then be shaken on a vortexer at maximum speed for 2 minutes using the vortex adapter. After shaking the sample will be centrifuged for 1 minute at 10,000×g and the supernatant transferred to a clean tube provided with the extraction kit. (Step 4) To the supernatant, 250 µl of Solution C2 will be added and mixed by inverting 5 times and placed on ice for 5 minutes. The sample will then be centrifuged for 1 minute at 10,000×g and the supernatant transferred to a new tube provided by with the extraction kit. (Step 5) To the supernatant, 200 µl of Solution C3 will be added and mixed by inverting 5 times and placed on ice for 5 minutes. The sample will then be centrifuged for 1 minute at 10,000×g and 700 µl the supernatant transferred to a new tube provided by with the extraction kit. (Step 6) To the supernatant, 1200 µl of Solution C4 will be added and inverted 5 times to mix. (Step 7) 625 µl of the sample +C4 solution will be loaded on to a Spin Filter provided with the extraction kit and centrifuged for 1 minute at 10,000×g. The Spin Filter will be removed from the catch tube and the eluate discarded followed by replacement of the Spin Filter into the catch tube. Step 7 will be repeated until the entire volume of sample+C4 has been passed through the Spin Filter. After the final volume of eluate has been discarded, (Step 8) the Spin Filter will be placed back into the catch tube to which 500 µl Solution C5 will be added to the spin Filter and centrifuged for 30 seconds at 10,000×g. The eluate in the catch tube will be discarded and the Spin Filter placed into the catch tube and centrifuged for an additional 1 minute 10,000×g. (Step 9) The Spin Filter will be placed in a new catch tube to which 100 Solution C6 will be added to Spin Filter and allowed to incubate at room temperature for 1 minute. The Spin filter will then be centrifuged for 30 seconds at 10,000×g and the eluted DNA stored at −20° C. or −80° C. until needed.

In an embodiment for DNA extractions from a large number of samples, a multiple high throughput DNA extraction kit or protocol can be followed. An example of such a protocol can have the following steps: (Step 1) 135-150 µL of oil (this amount should be calibrated and optimized based on the numbers of microorganisms contained in the samples and the kit or protocol used) from each sample will be placed in each well of a Bead plate of the DNA extraction kit and 750 µL of Bead Solution is then added to each well. (Step 2) 60 µL of Solution C1 will then be added to each sample, the plate is then sealed using a Square Well Mat or other means, and then heated to 65° C. for 10 minutes, (Step 3) The Bead plate is placed between aluminum plate adaptors and shaken on a 96 well plate shaker at speed 20 for 2 minutes. After shaking the Bead plate will be centrifuged for 6 minutes at 4500×g. (Step 4) A 96 well plate (call this Plate #1) is prepared by adding 250 µl aliquots of Solution 02 into each well. Plate #1 is then covered with Sealing Tape. The Square Well Mat on the Bead plate is removed after centrifugation. (Step 5) After removal of the Sealing Tape from Plate #1, the supernatant from the Bead plate (~400-500 µL) is transferred to Plate #1, and pipetted several times to mix with the solution already in Plate #1. (Step 6) The Sealing Tape is reapplied to Plate #1, which is then incubated at 4° C. for 10 minutes and then centrifuged at room temperature for 6 minutes at 4500×g. While centrifuging, 200 µl Solution C3 is aliquoted into each well of a new 96 well plate (call it Plate #3), then covered with Sealing Tape. (Step 7) Sealing Tape is removed from Plate #1 and the supernatant is removed (~600 µl; avoiding the pellet) and placed into the wells of another new 96 well plate (call it Plate #2). (Step 8) Plate #2 is sealed with Sealing Tape and the plate is centrifuged at room temperature for 6 minutes at 4500×g. (Step 9) After removing the sealing tape from Plates #2 and #3, the entire volume of supernatant (~600 µl) is transferred from Plate #2 to Plate #3; this volume is pipetted up and down 4 times. (Step 10) After the application of Sealing Tape to Plate #3, it is incubated at 4° C. for 10 minutes, and then centrifuged at room temperature for 6 minutes at 4500×g. (Step 11) The supernatant (~750 µl, avoiding the pellet) from Plate #3 is transferred to a new plate (call it Plate #4). (Step 12) After the application of Sealing Tape to Plate #4, it is centrifuged at room temperature for 6 minutes at 4500×g. While centrifuging, aliquot 650 µl of Solution C4 to the wells of a new 2 mL collection plate (call it Plate #5). (Step 13) The supernatant (up to 650 µl max) is then transferred to Plate #5. (Step 14) Add 650 µl Solution C4 again to Plate #5, which is pipetted to mix thoroughly. (Step 15) The Spin Plate filter is then placed on a new 2 mL collection plate (call it Plate #6) and 650 µl from Plate #5 is placed into each well of the Spin Plate. Centrifuge Tape is applied to the Spin Plate. (Step 16) The Spin Plate is centrifuged at room temperature for 5 minutes at 4500×g. The flow through is discarded. The Spin Plate is placed back on Plate #6. (Step 17) Steps 15-16 are repeated until all the supernatant has been processed through the Spin Plate filter and then Spin Plate is placed back on Plate #6. (Step 18) 500 µl of Solution C5-D is added to each well of the Spin Plate and Centrifuge Tape is applied to the Spin Plate. (Step 19) The plates are then centrifuged at room temperature for 5 minutes at 4500×g. The flow through is discarded and the Spin Plate placed back on Plate #6. (Step 20) The plates are centrifuged for 6 minutes at 4500×g. Flow through is again discarded. (Step 21) The Spin Plate is placed on the Microplate included in the kit and 100 µl of Solution C6 is added to each well of the Spin Plate. Centrifuge Tape is applied and the plates are set to rest for 10 minutes at room temperature. (Step 22) The plates are centrifuged at room temperature for 7 minutes at 4500×g. The Centrifuge Tape is then removed and thrown away. The wells of the Microplate are then covered with the Elution Sealing Mat from the kit. DNA is ready for any future work.

Example 3—Subsurface Sediment From Exploration Borehole

At the target site, samples will be collected from the material brought to the surface by the drill with the depth of the sample estimated from the length of drill inserted into the borehole. Personal protective gear should be donned to reduce contamination factors discussed above. Approximately 50-100 g of sediment from the drill will be collected using an ethanol sterilized metal spatula and placed into a sterile whirl type bag or large grab of soil will be made using a sterile whirl pack bag that is inside out (for instance the bag is used as it another glove) and stored in cooler with ice (or not depending on the environmental temperature). The metal spatulas will be wiped clean and ethanol sterilized in between the collection of each sample. The sample temperature should not be kept any warmer than the environment the samples were collected from, ideally between 4° C. and −80° C. for storage and shipment, and or ambient temperatures if deemed allowable.

Once the sample(s) are received at an analysis facility or mobile testing station, DNA will be extracted using, for example, a commercial extraction kit kit with some modifications, for example, the MoBio™ PowerSoil® DNA extraction. For example for single extractions: (Step 1) approximately 0.1 g (this amount should be calibrated and optimized based on the numbers of microorganisms contained in the samples and the kit or protocol used) of soil from each sample will be placed in a Bead tube. (Step 2) 60 µL of Solution will then be added to the sample in the Bead Tube and heated to 65° C. for 10 minutes. (Step 3) The sample will then be shaken on a vortexer at maximum speed for 2 minutes using the MoBio™ vortex adapter. After shaking the sample will be centrifuged for 1 minute at 10,000×g and the supernatant transferred to a clean tube provided with the extraction kit. (Step 4) To the supernatant, 250 µl of Solution C2 will be added and mixed by inverting 5 times and placed on ice for 5 minutes. The sample will then be centrifuged for 1 minute at 10,000×g and the supernatant transferred to a new tube provided by with the extraction kit, (Step 5) To the supernatant, 200 µl of Solution C3 will be added and mixed by inverting 5 times and placed on ice for 5 minutes. The sample will then be centrifuged for 1 minute at 10.000×g and 700 µl the supernatant transferred to a new tube provided by with the extraction kit. (Step 6) To the supernatant, 1200 µl of Solution C4 will be added and inverted 5 times to mix. (Step 7) 625 µl of the sample+C4 solution will be loaded on to a Spin Filter provided with the extraction kit and centrifuged for 1 minute at 10,000×g. The Spin Filter will be removed from the catch tube and the eluate discarded followed by replacement of the Spin Filter into the catch tube. Step 7 will be repeated until the entire volume of sample+C4 has been passed through the Spin Filter. After the final volume of eluate has been discarded, (Step 8) the Spin Filter will be placed back into the catch tube to which 500 µl Solution C5 will be added to the Spin Filter and centrifuged for 30 seconds at 10,000×g. The eluate in the catch tube will be discarded and the Spin Filter placed into the catch tube and centrifuged for an additional 1 minute 10,000×g. (Step 9) The Spin Filter will be placed in a new catch tube to which 100 µl Solution C6 will be added to Spin Filter and allowed to incubate at room temperature for 1 minute. The Spin filter will then be centrifuged for 30 seconds at 10,000×g and the eluted DNA stored at −20° C. until needed.

In an embodiment DNA extractions from a large number of samples, a commercial protocol or kit with some minor modifications could be followed, for example the high throughput MoBio™ PowerSoil® protocol. Pretreatments to used prior to extraction protocol, to remove excess salts, chemicals, and/or metals may be necessary. An example of a sample protocol could include (Step 1) approximately 0.1 g (this amount should be calibrated and optimized based on the numbers of microorganisms contained in the samples and the kit or protocol used) of soil/water/sediment from each sample will be placed in each well of a Bead plate of the DNA extraction kit and 750 µL of Bead Solution is then added to each well. (Step 2) 60 µL of Solution C1 will then be added to each sample the plate is then sealed using a Square Well Mat or other means, and then heated to 65° C. for 10 minutes, (Step 3) The Bead plate is placed between aluminum plate adaptors and shaken on a 96 well plate shaker at speed 20 for 2 minutes. After shaking the Bead plate will be centrifuged for 6 minutes at 4500×g. (Step 4) A 96 well plate (call this Plate #1) is prepared by adding 250 µl aliquots of Solution C2 into each well. Plate #1 is then covered with Sealing Tape. The Square Well Mat on the Bead plate is removed after centrifugation. (Step 5) After removal of the Sealing Tape from Plate #1, the supernatant from the Bead plate (~400-500 µL) is transferred to Plate #1, and pipetted several times to mix with the solution already in Plate #1. (Step 6) The Sealing Tape is reapplied to Plate #1, which is then incubated at 4° C. for 10 minutes and then centrifuged at room temperature for 6 minutes at 4500×g. While centrifuging, 200 µl Solution C3 is aliquoted into each well of a new 96 well plate (call it Plate #3), then covered with Sealing Tape. (Step 7) Sealing Tape is removed from Plate #1 and the supernatant is removed (~600 µl; avoiding the pellet) and placed into the wells of another new 96 well plate (call it Plate #2), (Step 8) Plate #2 is sealed with Sealing Tape and the plate is centrifuged at room temperature for 6 minutes at 4500×g. (Step 9) After removing the Sealing Tape from Plates #2 and #3, the entire volume of supernatant (~600 µl) is transferred from Plate #2 to Plate #3; this volume is pipetted up and down 4 times. (Step 10) After the application of Sealing Tape to Plate #3, it is incubated at 4° C. for 10 minutes, and then centrifuged at room temperature for 6 minutes at 4500×g. (Step 11) The supernatant (~750 µl, avoiding the pellet) from Plate #3 is transferred to a new plate (call it Plate #4). (Step 12) After the application of Sealing Tape to Plate #4, it is centrifuged at room temperature for 6 minutes at 4500×g. While centrifuging, aliquot 650 µl of Solution C4 to the wells of a new 2 mL collection plate (call it Plate #5). (Step 13) The supernatant (up to 650 µl max) is then transferred to Plate #5. (Step 14) Add 650 µl Solution C4 again to Plate #5, which is pipetted to mix throughly. (Step 15) The Spin Plate filter is then placed on a new 2 mL collection plate (call it Plate #6) and 650 µl from Plate #5 is placed into each well of the Spin Plate. Centrifuge Tape is applied to the Spin Plate. (Step 16) The Spin Plate is centrifuged at room temperature for 5 minutes at 4500×g. The flow through is discarded. The Spin Plate is placed back on Plate #6. (Step 17) Steps 15-16 are repeated until all the supernatant has been processed through the Spin Plate filter and then Spin Plate is placed back on Plate #6. (Step 18) 500 µl of Solution C5-D is added to each well of the Spin Plate and Centrifuge Tape is applied to the Spin Plate. (Step 19) The plates are then centrifuged at room temperature for 5 minutes at 4500×g. The flow through is discarded and the Spin Plate placed back on Plate #6. (Step 20) The plates are centrifuged for 6 minutes at 4500×g. Flow through is again discarded. (Step 21) The Spin Plate is placed on the Microplate included in the kit and 100 µl of Solution C6 is added to each well of the Spin Plate. Centrifuge Tape is applied and the plates are set to rest for 10 minutes at room temperature. (Step 22) The plates are centrifuged at room temperature for 7 minutes at 4500×g. The Centrifuge Tape is then removed and thrown away. The wells of the Microplate are then covered with the Elution Sealing Mat from the kit. DNA is ready for any future work.

Example 4—Drilling and Hydraulic Fracturing Fluid Collection

Drilling fluid, fracing fluid, oil-water mixtures or any liquid-solid slurry may be collected in large volume sterile containers that follow the teachings of this specifications. Steps will be taken to ensure that a minimum of oil will be involved in the filtration of any water components, as well as additional analyses to subtract out the oil portion of the results, may be warranted. The phases should be allowed to separate and the clear portion can be filtered through 0.22 um membrane filters to capture the microbes present in the sample. Samples with high loads of sand, bentonite, etc can be centrifuged at low speed (less than 1000 rcf) and the supernatant filtered through 0.22 um filters to capture microbes present in the sample. Filters can be stored from 4 to −80 C.

Example 5—Filter Sample Handing

The filters containing microbes should be carefully cut into small strips using ethanol-sterilized scissors and forceps on a sterile work surface such an petri dish located in a suitable clean work environment. Once cut, a portion of the strips can be loaded into the MoBio bead tube or into a well on a 96 well bead plate. DNA extraction can proceed as noted in above for either single or high-throughput extraction methods. The remaining filter strips can be stored at −20 to −80° C. for future use if desired.

Library Preparation

Amplification

Genetic material from the samples will be subjected to polymerase chain reaction (PCR) to amplify the gene of interest and encode each copy with barcode unique to the sample. Generally, PCR exponentially amplifies a single or a few copies of a piece of DNA across several orders of magnitude, generating thousands to millions, or more, of copies of a particular DNA sequence using a thermostable DNA polymerase. PCR will be used to amplify a portion of specific gene from the genome of the microbes present in the sample. Any method that can amplify genetic material quickly, accurately, and precisely can be used for library preparation.

The PCR primer will be designed carefully to meet the goals of the sequencing method. For instance, the PCR primer will contain a length of nucleotides specific to the target gene, may contain an adapter that will allow the amplicon, also known as the PCR product, to bind and be sequenced on a high-throughput sequencing platform, and additional nucleotides to facilitate sequencing. The portion of the gene with adapters, barcode and necessary additional nucleotides is known as the "amplicon." it being understood that future systems may not use, or need, adaptors.

The microbial ribosome is made up component proteins and non-coding RNA molecules, one of which is referred to as the 16S ribosomal RNA (or 16S rRNA), The 16S subunit is a component of the small subunit (SSU) of bacterial and archaeal ribosomes. It is 1.542 kb (or 1542 nucleotides) or another specified length. The gene encoding the 16S subunit is referred to as the 16S rRNA gene. The 16S rRNA gene is used for reconstructing phylogenies because it is highly conserved between different species of bacteria and archaea, meaning that is an essential (stable) part of the organisms who encode it in their genomes and it can be easily identified in genomic sequences, but it additionally contains regions that are highly unique (but most likely changed incrementally) and are used for classification sake, in other words there is a phylogenetic signature in the sequence of the gene. As a result of these same properties, batch sequencing of all of the 16S rRNA gene sequence in a sample containing many microbial taxa are informative about which microbial taxa are present. These studies are made possible by the remarkable observation that a small fragment of the 16S rRNA gene can be sufficient as a proxy for the full-length genomic sequence for many microbial community analyses, including those based on a phylogenetic tree.

Sequencing read accuracy and precision can affect the outcomes of any analysis including phylogenetic trees produced from those sequences. Some sequencing machines provide software that could be used to infer phylogenetic trees. For example, although the phylogenetic trees produced from approximately 250-base reads from the 454 Life Sciences™ (Roche) GS FLX instrument are relatively inaccurate, they are still much better, as has been identified and is known to the art, than the "star phylogeny," (phylogeny that assumes all species are equally related), that all non-phylogenetic methods for comparing communities use implicitly (e.g., by counting how many species are shared). However, such trees should, at most, be used as a guide to community comparisons and not for inferring true phylogenetic relationships among reads. Advances in sequencing technology, such as the availability of 400-base reads with the Titanium™ kit from Roche; the Illumina™ platforms which can produce 450 Gb per day, and in the course of a 10.8 day run produces 1.6 billion 100-base paired-end reads (HiSeq2000) or for single-day experiments can generate 1.5 Gb per day from 5 million 150-base paired-end reads (MiSeq™), or in the future, the availability of instruments providing 1500-base single-molecule reads, as reported by Pacific Biosciences™, will also improve the accuracy/productivity of existing methods for building phylogenetic trees and classifying functions of metagenomic reads.

Although metagenomics and other alternative techniques provide insight into all of the genes (and potentially gene functions and gene activities) present in a given community, 16S rRNA-based studies are extremely valuable given that they can be used to discover and record unexplored biodiversity and the ecological characteristics of either whole communities or individual microbial taxa at an even lower relative cost. 16S rRNA phylogenies tend to correspond well to trends in overall gene content. Therefore the ability to relate trends at the species level to host or environmental parameters has proven immensely powerful to understanding the relationships between the microbes and the world.

Alternative microbiome measurement techniques provide important information that is complementary to 16S rRNA or other marker-gene data: metagenomics provides genome content for the entire microbiome; transcriptomics measures gene expression by microbes, indicating which genes are actually being used by the microbes; proteomics measures actual production of enzymes and other functional proteins in the microbiome; metabolomics directly measures metabolite content in a sample.

Generally, analysis of ribosomal genes either by themselves or in combination (SSU, LSU, ITS) will be used for the determination and characterization of microbes in industrial settings where the only requirement for choosing the particular gene for amplification is that the gene is at least somewhat conserved between different species of microbes. For instance, the amplification, sequencing and analysis of the small subunit ("SSU") of the ribosomal gene (16S rRNA gene) would be used for bacteria and archaea while analysis of the eukarytotes such as nematodes, ciliates and amoeba would analyze the small subunit ribosomal gene (18S rRNA gene) common in these organisms. Further, LSU. ITS and the mitochondrial marker such as Cytb or cox1, may also be used and could provide enhanced performance. Fungal populations may also be characterized by the intragenic transcribed spacer gene ("ITS gene") in addition to 18S rRNA gene. Furthermore, the large subunit ribosomal gene ("LSU") could be analyzed alone or in combination with portions of the SSU in a single amplicon. The genetic material for any analysis could be derived from DNA or cDNA (i.e., complementary DNA) produced from the reverse transcription of RNA isolated from the target sample or samples.

Complete marker genes, such as the examples used above, generally cannot, because of their length, be sequenced using high-throughput methods. However, the use of PacBio or Moleculo technologies can provide the ability to obtain such a complete sequence with high fidelity. Therefore, typically a shorter region of the marker gene sequence must be selected to act as proxy. Currently, there is no consensus on a single best region, and consequently different groups are sequencing different or multiple regions. This diversity of methods hinders direct comparisons among studies. Standardization on a single region would be helpful on this front. Of the nine variable regions in the 16S rRNA gene, several of the more popular regions include the regions surrounding V2, V4, and V6. Generally, a combination of variable and moderately conserved regions appears to be optimal for performing analyses at different phylogenetic depths. Both the choice of region and the design of the primers are crucial, and poor design of primers as well as the use of different primers can lead to radically different experimental conclusions. Additionally, primer bias due to differential annealing leads to the over- or underrepresentation of specific taxa can lead to some groups being missed entirely if they match the consensus sequence poorly. Issues of primer bias can be important. For example, although some widely used primers such as 8F, 337F, 338R, 515F, 915F, 930R, 1046R, and 1061R match >95% of the sequences in Ribosome Database Project (RDP) from all of the major bacterial phyla in the normal human gut (Firmicutes, Bacteroidetes, Actinobacteria, Verrucomicrobia, and Proteobacteria), others miss specific divisions. For example, 784F is biased against Verrucornicrobia; 967F matches <5% of Bacteroidetes; and 1492R matches 61% of Actinobacteria, 54% of Proteobacteria, and fewer than half of the other divisions. Comparisons of relative abundance among different studies should thus be treated with caution. However, meta-analyses of presence/absence data from different studies is particularly useful for revealing broad trends, even when different studies use different primers.

As more sequence data and better taxonomic assignments become available, improved primer sets, with better coverage (including primers for archaea and eukaryotes), will likely provide a substantial advantage over present degenerate primer techniques (where a mixture of different primers that allow variation at one or more nucleotide in the sequence). Specifically, 16S rRNA and 18s rRNA reads from metagenomic studies provide a source of sequences that is not subject to PCR primer bias (although other biases are present) and therefore covers taxa that are missed by existing but popular primer sets, although in practice exploiting this information has been quite challenging. Another promising approach is the use of miniprimers, which, together with an engineered DNA polymerase, may allow greater coverage of desired groups. Likewise nested PCR techniques could be used for example, and not limited to identify specific motifs, sequences, genes, organisms, and/or any combination of these.

Furthermore, improvements in the ability to produce high quantities of primers (e.g. millions of individual primers) and appropriate reaction conditions will enable amplification of high quantities of regions (e.g. millions of individual regions), which may be distinct to each microbe or targeted at multiple sites obtained from existing databases or from shotgun sequencing. Such an application could be used to improved discrimination and/or prediction for a particular environment and target parameter (e.g. oil saturation in a reservoir). For example, we might determine that a collection of genes related to hydrocarbon reduction or oxidation are predictive of oil/water saturation, and then design primer sets against all of such genes identified via shotgun sequencing of a series of samples obtained from wells with varying oil/water saturation levels. Likewise, it might also be possible to design a chip on which primers and/or partial gene sequences could be based and amplify those genes of interest.

The primers designed for amplification will be well-suited for the phylogenetic analysis of sequencing reads. Thus, the primer design will be based on the system of sequencing, e.g., chain termination (Sanger) sequencing or high-throughput sequencing. Within the system, there are also many options on the method. For example, for high-throughput sequencing, the sequencing can be performed by, but is not limited to, 454 Life Sciences™ Genome Sequencer FLX (Roche) machine or the Illumina™ platforms (MiSeq™ or HiSeq™). These will be described more in the Sequencing section below.

Barcoding

High-throughput sequencing, described below, has revolutionized many sequencing efforts, including studies of microbial community diversity. High-throughput sequencing is advantageous because it eliminates the labor-intensive step of producing clone libraries and generates hundreds of thousands of sequences in a single run. However, two primary factors limit culture-independent marker gene-based analysis of microbial community diversity through high-throughput sequencing: 1) each individual run is high in cost, and 2) separating samples from a single plate across multiple runs is difficult. For example, analysis of multiple libraries on the 454™/Roche sequencers has room for up to a maximum of only 16 independent samples, which have to be physically segregated using manifolds on the sequencing medium. These separation manifolds block wells on the sequencing plate from accommodating bead-bound DNA template molecules, and thus limit the number of output sequences.

A solution to these limitations is barcoding. For barcoding, a unique tag will be added to each primer(s) before PCR amplification. Because each sample will be amplified with a known tagged (barcoded) primer(s), an equimolar mixture of PCR-amplified DNA can be sequenced from each sample and sequences can be assigned back to samples based on these unique barcodes. The presence of these assigned barcodes allow for independent samples to be combined for sequencing, with subsequent bioinformatic separation of the sequencer output. By not relying on physical separators, this procedure maximizes sequence space and multiplexing capabilities. This technique will be used to process many samples (eg 25, 200, 1000, and above,) and is mostly only limited by the number of barcoded primers used and the desired coverage (due to the total sequences expected from the given machine or method, and the reagents and/or cycles possible for the given machine used in sequencing) in a single high-throughput sequencing run. This number will be increased depending on advances in high-throughput sequencing technology, without limit to the number of samples to be sequenced in a single high-throughput sequencing run.

Barcodes, or unique DNA sequence identifiers, have traditionally been used in different experimental contexts, such as sequence-tagged mutagenesis (STM) screens where a sequence barcode acts as an identifier or type specifier in a heterogeneous cell-pool or organism-pool. However, STM barcodes are usually 20-60 bases (or nucleotides, nt) long, are pre-selected or follow ambiguity codes, and exist as one unit or split into pairs. Such long barcodes are not particularly compatible with available high-throughput sequencing platforms because of restrictions on read length.

Although very short (2- or 4-nt) barcodes can be used with high-throughput sequencing platforms, a more definitive assignment of samples and/or for enhanced multiplexing capabilities can be accomplished by lengthening the barcodes or variations in the fixed forward and reverse linkers used to generate the initial cDNA libraries. Shorter barcodes also have a steeper trade-off between number of possible barcodes and the minimum number of nucleotide variations between individual barcodes.

Existing barcoding methods have limits both in the number of unique barcodes used and in their ability to detect sequencing errors that change sample assignments (this robustness is especially important for sample assignment because the 5' end of the read (sequence for one strand of nucleic acid in a sample) is somewhat more error-prone). Barcodes based on error-correcting codes, which are widely used in devices in other technologies like telecommunications and electronics, will be applied for high-throughput sequencing barcoding purposes.

For example, a class of error-correcting codes called Hamming codes, which use a minimum amount of redundancy and will be simple to implement using standard linear algebra techniques. Hamming codes, like all error-correcting codes, employ the principle of redundancy and add redundant parity bits to transmit data over a noisy medium. Sample identifiers will be encoded with redundant parity bits. Then the sample identifiers will be "transmitted" as codewords. Each base (A, T, G, C) will be encoded using 2 bits and using 8 bases for each codeword. Therefore, 16-bit codewords will be transmitted. The codeword and bases is not limited to these numbers, as any number of bits and codewords can be designed by a person of ordinary skill in the art. The design of the barcode is based on the goals of the method. Hamming codes are unique in that they use only a subset of the possible codewords, particularly those that lie at the center of multidimensional spheres (hyperspheres) in a binary subspace. Single bit errors fall within hyperspheres associated with each codeword, and thus they can be corrected. Double bit errors do not fall within hyperspheres associated with each codeword, and thus they can be detected but not corrected.

Other encoding schemes, such as Golay codes, will also be used for barcoding. Golay codes of 12 bases can correct all triple-bit errors and detect all quadruple-bit errors. The extended binary Golay code encodes 12 bits of data in a 24-bit word in such a way that any 3-bit errors can be corrected or any 7-bit errors can be detected. The perfect binary Golay code, has codewords of length 23 and is obtained from the extended binary Golay code by deleting one coordinate position (conversely, the extended binary Golay code is obtained from the perfect binary Golay code by adding a parity bit). In standard code notation the codes have parameters corresponding to the length of the codewords, the dimension of the code, and the minimum Hamming distance between two codewords, respectively.

In mathematical terms, the extended binary Golay code consists of a 12-dimensional subspace W of the space $V=F_2^{24}$ of 24-bit words such that any two distinct elements of W differ in at least eight coordinates. Equivalently, any non-zero element of W has at least eight non-zero coordinates. The possible sets of non-zero coordinates as w ranges over W are called codewords. In the extended binary Golay code, all code words have the Hamming weights of 0, 8, 12, 16, or 24. Up to relabeling coordinates, W is unique.

Figure 6:
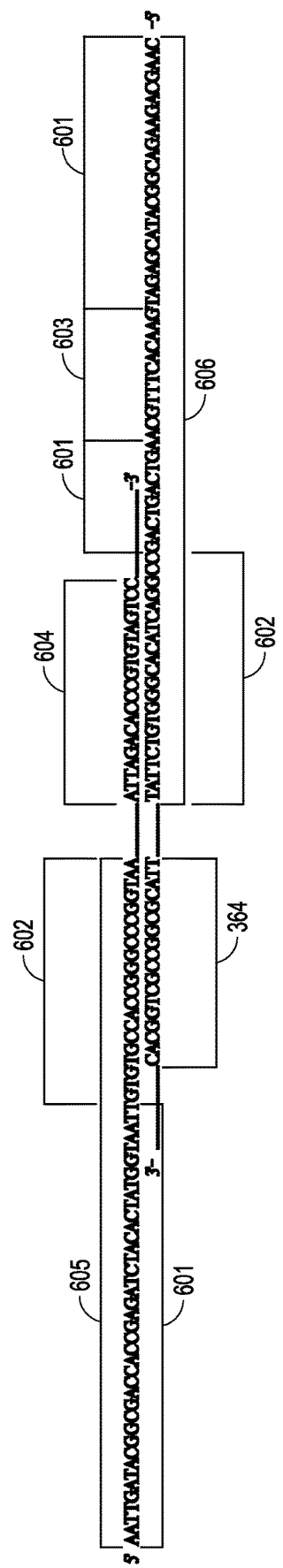
FIG. 6 is an illustration of an embodiment of barcoded primers for high-throughput sequencing in accordance with the present inventions.

FIG. 6 shows an example of the general design for barcoded primers for high-throughput sequencing. The primer will be designed to include nucleotides specific for the sequencing platform 601; nucleotides specific for the gene of interest 602; nucleotides for the Golay barcode 603; and the nucleotides of the gene 604. Upon amplification, one contiguous string of nucleotides known as the "forward" primer 605 will be formed from the platform specific sequencing adaptors 301 and the gene specific primer and linker 602. Additionally formed upon amplification will be one contiguous string of nucleotides known as the "reverse" primer formed from the platform specific sequencing adaptors 601, the gene specific primer and linker 602, and the barcode 603.

Figure 7:
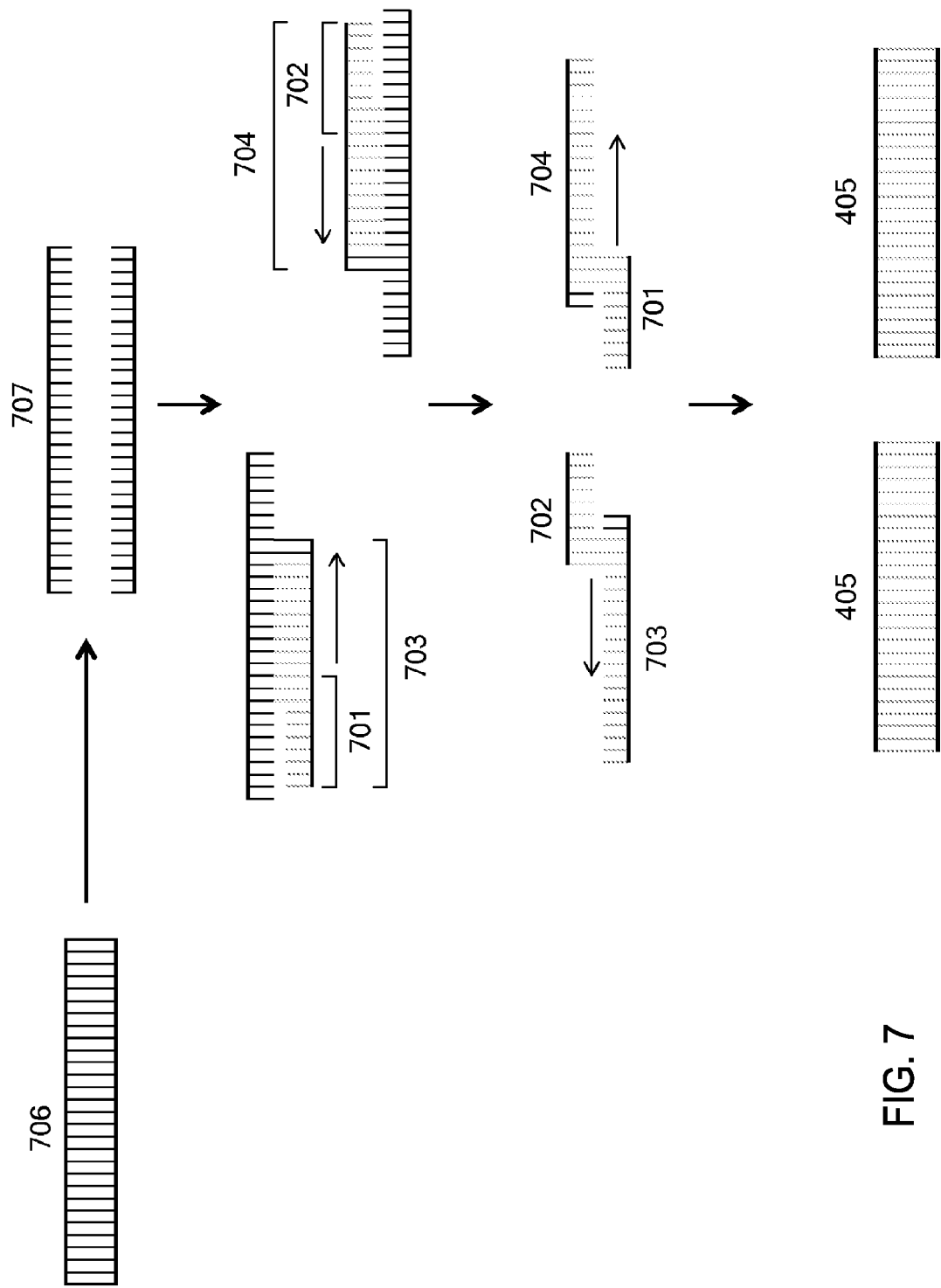
FIG. 7 is an illustration of an embodiment of polymerase chain reaction (PCR) in accordance with the present inventions.

FIG. 7 shows the general scheme for PCR using barcoded primers, designed as previously described. Double stranded target DNA 706 is denatured 707. Strands 701 and 702 will be annealed to the gene via the gene specific primer and linker (FIG. 6, 602). Thermostable DNA polymerase extends primers creating strands 703 and 704. Strands 703 and 704 will be denatured from the target DNA. Then strand 701 will be annealed to strand 704 while strand 702 will be annealed to strand 703. Through amplification, new strands 705 are produced. Strand 705 is a barcoded amplicon that can be sequenced. Further, other error-correcting codes may be utilized such as Gray codes, low-density parity check codes, etc.

The technique of high-throughput sequencing of these barcoded amplicons yields a robust description of the changes in bacterial community structure across the sample set. A high-throughput sequencing run is expensive, and the large number of custom primers required only adds to this cost. However, the barcoding technique allows for thousands of samples to be analyzed simultaneously, with each community analyzed in considerable detail. Although the phylogenetic structure and composition of the surveyed communities can be determined with a high degree of accuracy, the barcoded high-throughput sequencing method may not allow for the identification of bacterial taxa at the finest levels of taxonomic resolution. However, with increasing read lengths in sequencing, this constraint will gradually become less relevant.

Example 6

In one example, specifically for the Illumina™ sequencing machinery (described below), the following primers will be designed for amplification of 16S rRNA. The primer sequences in this protocol are always listed in the 5'→3' orientation.

```
515f PCR Primer Sequence- Forward primer
Field description(space-delimited):
1. 5' Illumina ™ adapter
2. Forward primer pad
3. Forward primer linker
4. Forward primer (515f)
AATGA TACGG CGACC ACCGA GATCT ACACT ATGGT
AATTG TGTGC CAGCM GCCGC GGTAA 806r PCR primer sequence- Reverse primer,
barcoded
Sheet of primer constructs contains 2168 Golay
barcoded reverse PCR primers generated
specifically for this set of primers.
Field description (space-delimited):
1. Reverse complement of 3' Illumina ™ adapter
2. Golay barcode
```

```
3. Reverse primer pad
4. Reverse primer linker
5. Reverse primer (806r)
CAAGC AGMG ACGGC ATACG AGAT XXXXXXXXXXXX
AGTCA GTCAG CCGGA CTACH VGGGT WTCTA AT Illumina ™ PCR Conditions: 515f-806r region of
the 16S rRNA gene:
Complete reagent recipe (master mix) for 1X
PCR reaction PCR
13.0 µL
Grade H2O (note a)

5 Primer
10.0 µL
Hot MM (note b)

Forward
0.5 µL
primer (10 µM)

Reverse
0.5 µL
primer (10 µM)

Template
1.0 µL
DNA

Total
25.0 µL
reaction volume

Notes:
PCR grade water was purchased from MoBio ™
Laboratories
Five Prime Hot Master Mix (5 prime)
Final primer concentration of mastermix: 0.2 µM
Thermocycler Conditions for 96 well
thermocyclers:
94° C. 3 minutes 94° C. 45 seconds 50° C. 60 seconds 72° C. 90 seconds Repeat steps 2-4 35 times 72° C. 10 minutes

4° C. HOLD

Thermocycler Conditions for 384 well thermocycler
94° C. 3 minutes

94° C. 60 seconds

50° C. 60 seconds

72° C. 105 seconds

Repeat steps 2-4 35 times

72° C. 10 minutes

4° C. HOLD
```

The samples will be amplified in triplicate, meaning each sample will be amplified in 3 replicate 25 µL PCR reactions (or the number of replicated required to meet an efficient and valid yield of DNA). The triplicate (or more as is deemed necessary) PCR reactions will be combined for each sample into a single volume. The combination will result in a total of 75 µL of amplicon for each sample. The amplicons from different samples will not be combined at this point. The amplicons for each sample will be run on an agarose gel. Expected band size for 515f/806r is roughly 300-350 bp. Amplicons will be quantified using Picogreen's® instructions or another sensitive DNA assessment method such as, Qubit® assays could be used. An equal amount of amplicon from each sample will be combined into a single, sterile tube. Generally, 240 ng of DNA per sample will be pooled. However, higher amounts can be used if the final pool will be gel isolated or when working with low biomass samples. When working with multiple plates of samples, it is typical to produce a single tube of amplicons for each plate of samples. The amplicon pool will be cleaned using MoBio™ UltraClean® PCR Clean-Up Kit #12500, following the instructions provided therein. If working with more than 96 samples, the pool will need to be split evenly for cleaning and then recombined. If spurious bands are present on the previously mentioned agarose gel, half of the final pool will be run on a gel and then gel extracted to select only the target bands. The concentration of the final pool will be determined fluormetrically with PicoGreen® ds DNA reagent, or equivalent assay, as spectrophotometric methods are not suitable for quantification. However, the 260 nm/280 nm ratio should be determined spectrophotometrically as this is a measure of sample purity and can be critical to successful sequencing with the ratio between 1.8 and 2.0. Negative or blank controls of all reagents should be included to test for contamination. An aliquot of this final sample will be used for sequencing along with sequencing primers listed below.

```
Read 1 sequencing primer:
Field description (space-delimited):
1, Forward primer pad
2, Forward primer linker
3, Forward primer
TATGG TAATT GTGTG CCAGC MGCCG CGGTA A Read 2 sequencing primer:
Field description (space-delimited):
1, Reverse primer pad
2, Reverse primer linker
3, Reverse primer
AGTCA GTCAG CCGGA CTACH VGGGT WTCTA AT Index sequence primer:
Field description (space-delimited):
1. Reverse complement of reverse primer
2. Reverse complement of reverse primer linker
3. Reverse complement of reverse primer pad
ATTAG AWACC CBDGT AGTCC GGCTG ACTGA CT
```

Example 7

In another example, for each sample, the 16S rRNA gene will be amplified using a primer set including:

```
Forward primer
(5'-GCCTTGCCAGCCCGCTCAGTCAGAGTTTGATCCTGGCTCAG-3')
``` which contains the 454 Life Sciences™ primer B, the broadly conserved bacterial primer 27F, and a 2-base linker sequence ("TC");

```
Reverse primer
(5'-GCCTCCCTCGCGCCATCAGNNNNNNNNNNNNCATGCTGCCTCC
CGTAGGAGT-3')
``` which contains the 454 Life Sciences™ primer A, the bacterial primer 338R, a "CA" inserted as a linker between the barcode and the rRNA primer (with the specific linker depending on the region of sequence targeted by the primer and which, unlike the PCR primer which is designed to be complimentary to the target sequences, is specifically designed to not be complimentary to the target sequences so the base pairing interactions are disrupted in all target sequences at this position—if this linker were not present, some barcodes would anneal to the target, while some would not, leading to barcode-specific PCR biases) and a unique 12-bp error-correcting Golay barcode used to tag each PCR product (designated by NNNNNNNNNNNN). PCRs will consist of 0.25 μL (30 μM) of each forward and reverse primer, 3 μL of template DNA, and 22.5 μL of Platinum® PCR SuperMix by Invitrogen™. Samples will be denatured at 94° C. for 3 min, then amplified by using 35 cycles of 94° C. for 45 seconds, 50° C. for 30 seconds, and 72° C. for 90 seconds. A final extension of 10 minutes at 72° C. will be added at the end of the program to ensure complete amplification of the target region. All samples will be amplified in triplicate Although, PCR should be optimized for the specific reaction. Negative controls (both no-template and tem-plate from unused cotton swabs (referring back to Example 6)) will be included in all steps of the process to check for primer or sample DNA contamination. All aliquoting and diluting of primers, as well as assembly of PCRs, will be done in a PCR hood in which all surfaces and pipettes had been decontaminated with DNA AWAY™ by Molecular BioProducts™ and exposed to UV light for 30 minutes.

A composite sample for DNA sequencing will be prepared by pooling approximately equal amounts of PCR amplicons from each sample. The replicate PCRs for each sample will be combined and cleaned with the Mobio™ UltraClean®-htp PCR Clean-up kit as directed by the manufacturer. Each sample (3 μL) was then quantified by using PicoGreen® dsDNA reagent by Invitrogen™ in 1× Tris-EDTA (pH 8.2) in a total volume of 200 L on black, 96-well microtiter plates on a BioTek™ Synergy™ HTP microplate reader by BioTek Instruments, using the 480/520-nm excitation and emission filter pair. Once quantified, the appropriate volume of the cleaned PCR amplicons will be combined in a sterile, 50-mL polypropylene tube and precipitated on ice with sterile 5 M NaCl (0.2 M final concentration) and 2 volumes of ice-cold 100% ethanol for 45 minutes. The precipitated DNA will be centrifuged at 7,800 g for 40 minutes at 4° C., and the resulting will be washed with an equal volume of 70% ethanol and will be centrifuged again at 7,800 g for 20 minutes at 4° C. The supernatant will be removed, and the pellet will be air-dried for 7 minutes at room temperature, then resuspended in 100 μL of DNA-nuclease free water. The sample will be then ready for sequencing.

Example 8

Small-subunit ribosomal genes (16S) will be amplified using universal 515F (5'-GTGCCAGCMGCCGCGGTAA-3') and 1391R (5'-GACGGGCGGTGWGTRCA-3') primers for bacterial 16S rRNA genes. The PCR reaction will contained 1×PCR Buffer from Invitrogen, 2.5 mM $MgCl_2$, 0.2 μM of each primer, 0.2 μM dNTPs, 0.5 U Taq DNA polymerase by Invitrogen™ and 1.0 μl template DNA. Amplification will be accomplished by initial denaturation at 94° C. for 3 minutes followed by 25 cycles of 94° C. for 30 seconds, 50° C. for 30 seconds and 72° C. for 30 seconds with a final extension at 72° C. for 10 minutes. Each DNA sample will be amplified in triplicate and the amplicons will be pooled by plot and run on a 1.5% agarose gel. The bands will be purified using the Promega™ Wizard® SV Gel and PCR Clean-Up System. The sample will be then ready for sequencing.

Example 9

In another example, a portion of the 16S small-subunit ribosomal gene (positions 27 to 338 [V1 and V2]; *Escherichia coli* numbering) will be amplified using a 27F primer with a Roche 454™ A pyrosequencing adapter, while the 338R primer will contain a 12-bp bar-code sequence, a TC linker, and a Roche 454™ B sequencing adapter. The particular gene region has been shown to be very appropriate for accurate taxonomic classification of bacterial sequences, because other regions of the 16S rRNA gene can lead to significant misclassification of sequences. The barcode for each sample will be unique and error correcting to facilitate sorting of sequences from a single pyrosequencing run. PCRs will be conducted with 30 μM of each forward and reverse primer, 1.5 μl template DNA, and 22.5 μl Platinum® PCR SuperMix by Invitrogen™. Each sample will be amplified in triplicate, pooled, and cleaned using a MoBio™ 96 htp PCR cleanup kit. Equal amounts of PCR product for each sample will be combined in a single tube for sequencing.

Sequencing

The vast majority of life on earth is microbial, and the vast majority of these microbial species has not been, and is not capable of being easily cultured in the laboratory. Consequently, our primary source of information about most microbial species consists of fragments of their DNA sequences. Sequencing a DNA library will be done on a platform capable of producing many sequences for each sample contained in the library. High-throughput sequencing technologies have allowed for new horizons in microbial community analysis by providing a cost-effective method of identifying the microbial OTUs that are present in samples. These studies have drastically changed our understanding of the microbial communities in the human body and on the planet. This development in sequencing technology, combined with more advanced computational tools that employ metadata to relate hundreds of samples to one another in ways that reveal clear biological patterns, has reinvigorated studies of the 16S rRNA and other marker genes. Studies of 16S rRNA genes provide a view of which microbial taxa are present in a given sample because these genes provide an excellent phylogenetic marker. Although alternative techniques, such as metagenomics, provide insight into all of the genes (and potentially gene functions) present in a given community, 16S rRNA-based surveys are extraordinarily valuable given that they can be used to document unexplored biodiversity and the ecological characteristics of either whole communities or individual microbial taxa. Perhaps because 16S rRNA phylogenies tend to correspond well to trends in overall gene content, the ability to relate trends at the species level to host or environmental parameters has proven immensely powerful. The DNA encoding the 16S rRNA gene has been widely used to specify bacterial and archaeal taxa, since the region can be amplified using PCR primers that bind to conserved sites in most or all species, and large databases are available relating 16S rRNA sequences to correct phylogenies. However, as previously discussed, other genes or regions can be used to specify the taxa, such as 18S, LSU, ITS, and SSU (e.g., 16S). For the purposes of bacteria, cpn60 or ftsZ, or other markers, may also be utilized.

New technologies have led to extraordinary decreases in sequencing costs. This rapid increase in sequencing capacity has led to a process in which newer sequencing platforms generate datasets of unprecedented scale that break existing software tools: new software is then developed that exploits these massive datasets to produce new biological insight, but in turn the availability of these software tools prompts new experiments that could not previously have been considered, which lead to the production of the next generation of datasets, starting the process again.

High-Throughput Sequencing

With the advent of high-throughput sequencing, characterization of the nucleic acid world is proceeding at an accelerated pace. Three major high-throughput sequencing platforms are in use today: 1) the Genome Sequencers from Roche/454 Life Sciences™ [GS-20 or GS-FLX]; 2) the 1G Analyzer from Illumina™/Solexa™ which includes the MiSeq™ and the HiSeq™; and 3) the SOLiD™ System from Applied Biosystems™. Comparison across the three platforms reveals a trade-off between average sequence read length and the number of DNA molecules that are sequenced. The Illumina™/Solexa™ and SOLiD systems provide many more sequence reads, but render much shorter read lengths than the 454™/Roche Genome Sequencers. This makes the 454™/Roche platform appealing for use with barcoding technology, as the enhanced read length facilitates the unambiguous identification of both complex barcodes and sequences of interest. However, even reads of less than 100 bases can be used to classify the particular microbe in phylogenetic analysis. Any platform, for example, Illumina™, providing many reads and read lengths of a predetermined necessary length, for example, 150 base pairs or 100 base pairs, is acceptable for this method.

Because the accuracy of phylogenetic reconstruction depends sensitively on the number of informative sites, and tends to be much worse below a few hundred base pairs, the short sequence reads produced from high-throughput sequencing, which are 100 base pairs on average for the GS 20 (Genome Sequencer 20 DNA Sequencing System, 454 Life Sciences™), may be unsuitable for performing phylogenetically based community analysis. However, this limitation can be at least partially overcome by using a reference tree based on full-length sequences, such as the tree from the Greengenes 16S rRNA ARB Database, and then using an algorithm such as parsimony insertion to add the short sequence reads to this reference tree. These procedures are necessarily approximate, and may lead to errors in phylogenetic reconstruction that could affect later conclusions about which communities are more similar or different. One substantial concern is that because different regions of the rRNA sequence differ in variability, conclusions drawn about the similarities between communities from different studies might be affected more by the region of the 16S rRNA that was chosen for sequencing than by the underlying biological reality.

The increase in number of sequences per run from parallel high-throughput sequencing technologies such as the Roche 454 GS FLX™ (5×105) to Illumina GAIIx™ (1×108) is on the order of 1,000-fold and greater than the increase in the number of sequences per run from Sanger (1×103 through 1×104) to 454™. The transition from Sanger sequencing to 454™ sequencing has opened new frontiers in microbial community analysis by making it possible to collect hundreds of thousands of sequences spanning hundreds of samples. A transition to the Illumina™ platform allows for more extensive sequencing than has previously been feasible, with the possibility of detecting even OTUs that are very rare. By using a variant of the barcoding strategy used for 454™ with the Illumina™ platform, thousands of samples could be analyzed in a single run, with each of the samples analyzed in unprecedented depth.

A few sequencing runs using 454™/Roche's pyrosequencing platform can generate sufficient coverage, among many other applications, for assembling entire microbial genomes, for the discovery, identification and quantitation of small RNAs, and for the detection of rare variations in cancers, among many other applications. However, as the analytical technology becomes more advanced, the coverage provided by this system becomes unnecessary for phylogenetic classification. For analysis of multiple libraries, the 454/Roche™ pyrosequencers can accommodate a maximum of only 16 independent samples, which have to be physically separated using manifolds on the sequencing medium, drastically limiting the utility in the effort to elucidate the diverse microbial communities in each sample. Relatively speaking, the Illumina™ platforms are experiencing the most growth. However, with the constant improvements in sequencing systems, the different platforms that will be used will change over time. Generally, the method describe herein will be used with any available high-throughput sequencing platform currently available or will be available in the future. For example, the method described herein will be applied to a sequencing method wherein the genetic material will be sequenced without barcoding by simply placing the DNA or RNA directly into a sequencing machine.

In general, high-throughput sequencing technology allows for the characterization of microbial communities orders of magnitude faster and more cheaply than has previously been possible. For example, a typical Illumina MiSeq™ run can produce as many as 50 million, short paired end reads in the v3 chemistry (~300 bp long; 1.5× $10^{10}$ bp of data, or in the v2 chemistry, 250 bp; $7.5 \times 10^9$ bp) in 65 hours compared to Sanger sequencing which may take a day or more to produce only 96 reads of 800 bp in length (~$7.7 \times 10^4$ bp of data). In addition, the ability to barcode amplicons from individual samples means that hundreds of samples can be sequenced in parallel, further reducing costs and increasing the number of samples that can be analyzed. Though high-throughput sequencing reads tend to be short compared to those produced by the Sanger method, the sequencing effort is best focused on gathering more short sequences (less than 150 base pairs or less than 100 base pairs) rather than fewer longer ones as much of the diversity of microbial communities lies within the "rare biosphere," also known as the "long tail," that traditional culturing and sequencing technologies are slow to detect due to the limited amount of data generated from these techniques.

In statistics, a power law is a functional relationship between two quantities, where one quantity varies as a power of another. Power law distributions or functions characterize an important number of behaviors from nature and human endeavor. The observation of such a distribution often points to specific kinds of mechanisms, and can often indicate a deep connection with other, seemingly unrelated systems. An example of a power law graph is shown in FIG. 15.

Figure 15:
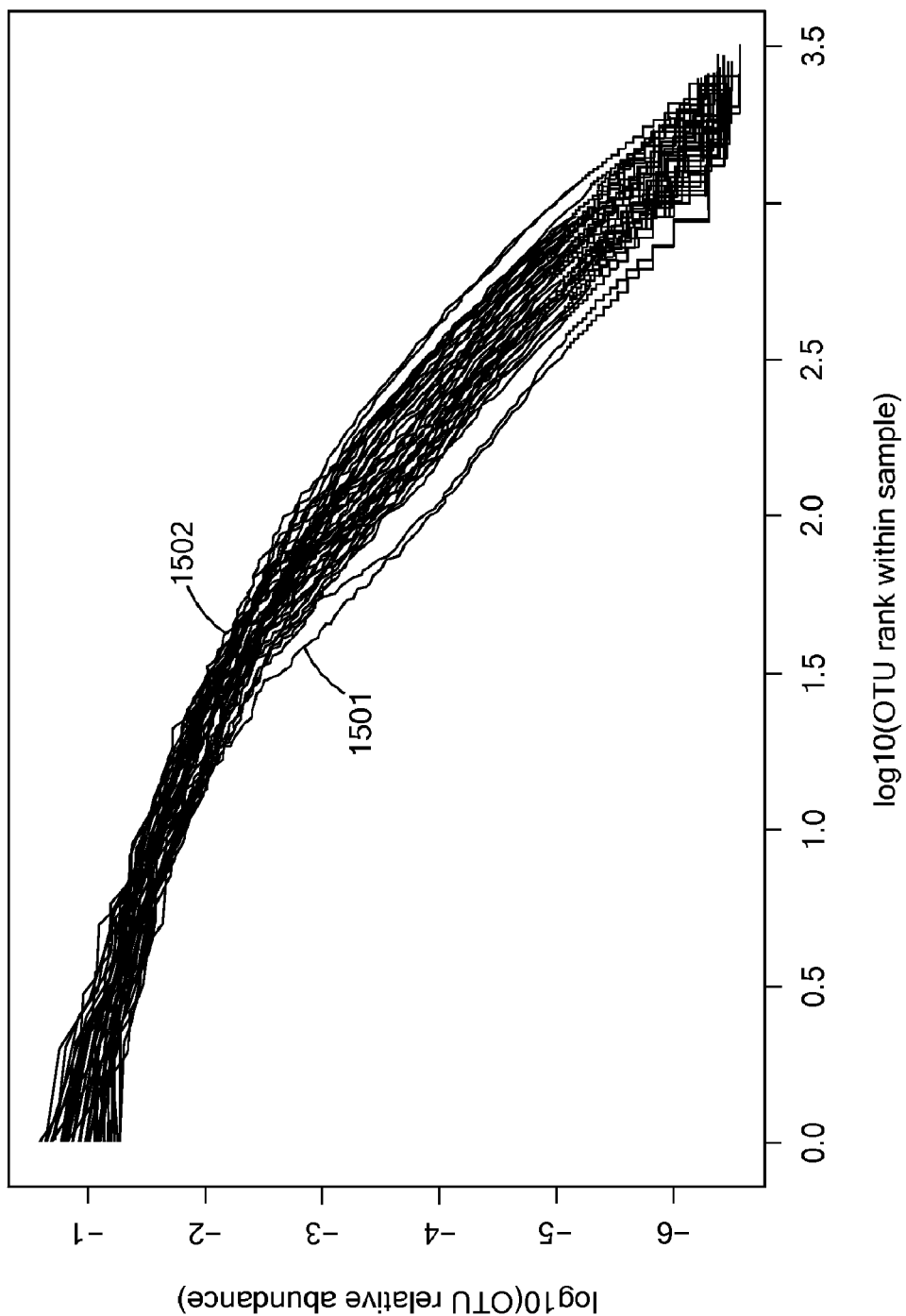
FIG. 15 is an illustration of a power law distribution in accordance with an embodiment of the present inventions.

FIG. 15 is a graph of a power law distribution. Each line, e.g., 1501, 1502, represents one of 134 human gut microbiome samples from healthy adults living in the USA included in a global survey of gut microbial diversity. To avoid undersampling of the rare microbiome, samples were sequenced at very high depth, ranging from 305,631 to 3,486,888 sequences per sample (mean±s.d.=2,018, 984±543,962.2). The x- and y-axes are log scale (i.e., it is a log-log plot), where the y value represents the abundance of an OTU, and the x is the "rank" of that OTU from most abundant to least abundant. The fact that this relationship is linear in a log-log plot defines it as embodying a power law distribution. This means that the most abundant OTU is 10 times more abundant than the tenth most abundant OTU.

In the power law graph example, a long tail of some distributions of numbers is the portion of the distribution having a large number of occurrences far from the "head" or central part of the distribution. The distribution could involve many factors including but not limited to popularities, random numbers of occurrences of events with various probabilities, etc. A probability distribution is said to have a long tail, if a larger share of population rests within its tail than would under a normal distribution. A long-tail distribution will arise with the inclusion of many values are unusually far from the mean, A long-tailed distribution is a particular type of heavy-tailed distribution.

Microorganisms of extremely low abundance have been designated the "rare biosphere" or "long tail." The ecological significance of rare microorganisms is just beginning to be understood. One hypothesis is that rare members represent a dormant seed bank. Members of this seed bank may become active at random or in direct response to changes in the environment, for instance, to initiate community recovery after disturbance. This hypothesis is supported by a recent investigation of marine bacterioplankton responses to organic carbon additions, wherein rare members increased in abundance from less than 10 sequences to as many as thousands after carbon amendment. Similarly, a study in the Western English Channel showed that community members in low abundance were persistent over time, and that, in a few cases, populations of rare members occasionally bloomed. However, there also are situations in which rare members are hypothesized to be less important for the community, such as when populations are becoming extinct or are between favorable environments. Because members of the rare biosphere may provide novel products and processes, bioprospecting for these organisms has been made a priority.

The length of the read of a sequence describes the number of nucleotides in a row that the sequencer is able to obtain in one read. This length can determine the type of taxa classification (e.g., family, genus or species) or OTU obtained. For example, a read length of approximately 300 base pairs will probably provide family information, but perhaps not a species determination. Depth of coverage in DNA sequencing refers to the number of times a nucleotide is read during the sequencing process. On a genome basis, it means that, on average, each base has been sequenced a certain number of times (10×, 20× . . . ). For a specific nucleotide, it represents the number of sequences that added information about that nucleotide. Coverage is the average number of reads representing a given nucleotide in the reconstructed sequence, Depth can be calculated from the length of the original genome (G), the number of reads (N), and the average read length (L) as N×L/G. For example, a hypothetical genome with 2,000 base pairs reconstructed from 8 reads with an average length of 500 nucleotides will have 2× redundancy. This parameter also enables estimation of other quantities, such as the percentage of the genome covered by reads (coverage). Sometimes a distinction is made between sequence coverage and physical coverage. Sequence coverage is the average number of times a base is read. Physical coverage is the average number of times a base is read or spanned by mate paired reads.

Figure 8:
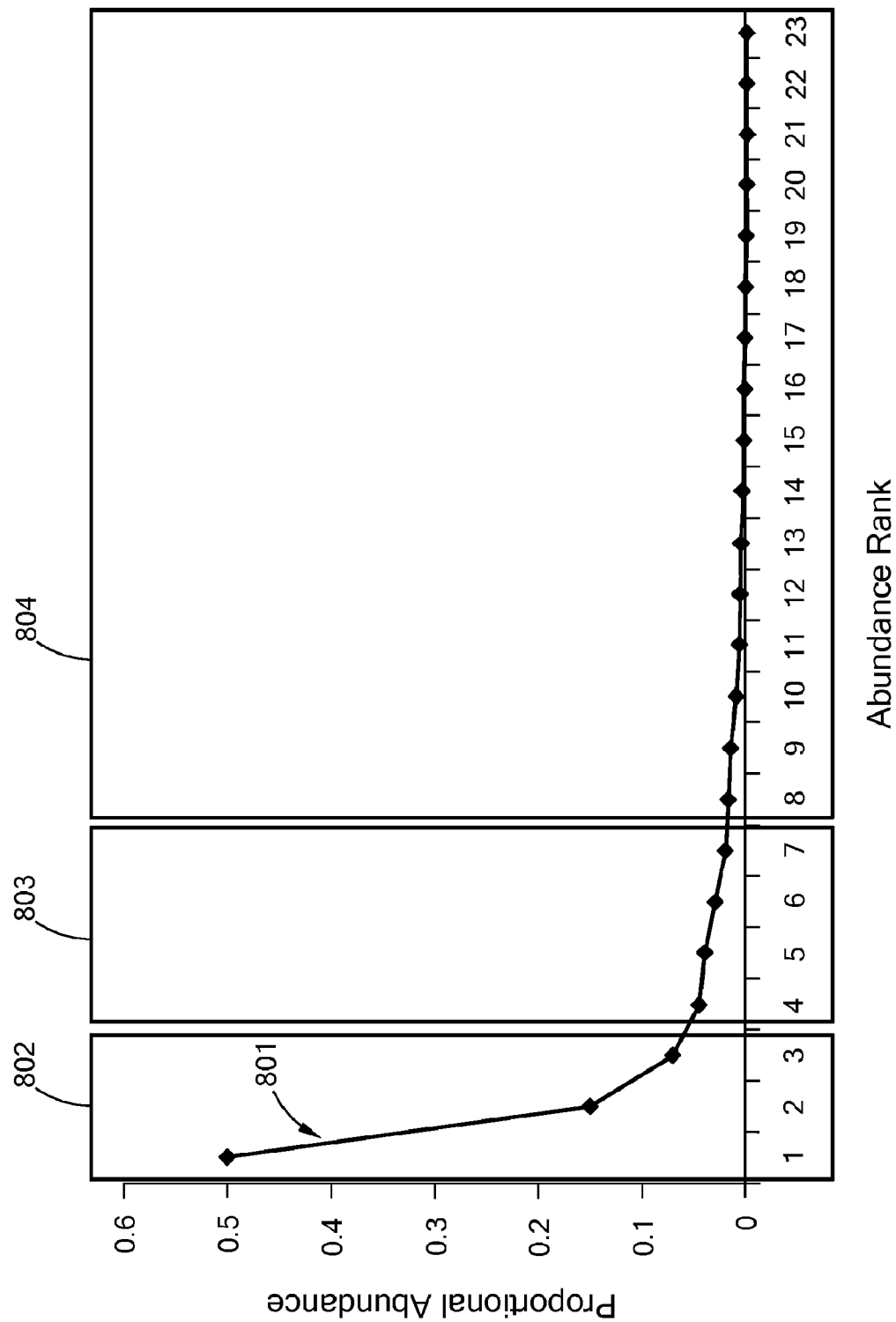
FIG. 8 is a chart of an illustration of an embodiment of a power law graph in accordance with the present inventions.

The line 801 plotted in the graph of FIG. 8 shows the ranked abundance of the OTUs on the x-axis with the most abundant species near the origin of the plot. The y-axis is the relative abundance of the OTU. The rare biosphere is the part of the line which has low values on the Y-axis. For instance, OTU 10 is the $10^{th}$ most abundant organism but represents less than 0.1% of the total OTUs present in the sample, while OTU 1 represents 50% of the OTUs in the same sample. Organisms of lower abundance rank can be detected if more sequence reads are collected. For example, the most abundant OTUs that are in box 802 are verified by a relatively low read depth. The moderately abundant OTUs that are in box 803 are verified by an increasing read depth. The long tail, which signifies the rare members of the community, is in box 804. To verify that these sequences are present, a higher read depth (i.e. more sequences) must be obtained. Analyzing the rare biosphere is attainable because sequencing depth provided by high-throughput sequencing allows for the detection of microbes that would otherwise be detected only occasionally by chance with traditional techniques.

With existing technology, the realistic time requirement for nucleic acid extraction, library preparation and sequencing is approximately a few days for a few samples. Analysis of the sequencing data will require an additional few hours depending on the system and amount of sequencing data produced. However, with minimizing the necessary read length, for example, to less than 150 base pairs or less than 100 base pairs, and maximizing the read depth in order to capture the organisms in the long tail of the power law graph, this time can be variable. Another variable factor is the advances in technology for high-throughput sequencing. Thus high-throughput sequencing will allow for the analysis of the more rare members (low abundance organisms) of any environment which may play critical role in, for example, oil and gas production, petroleum pipeline maintenance, food production, agriculture and other industries where microbes are present within a time-frame feasible for industrial settings. For example, the time from sampling to analysis of the sequencing information will be reduced to a few days or a few hours, and in another example, as quickly as under an hour, or under a few minutes, or preferably under a minute.

Pyrosequencing

One type of high-throughput sequencing is known as pyrosequencing. Pyrosequencing, based on the "sequencing by synthesis" principle, is a method of DNA sequencing widely used in microbial sequencing studies. Pyrosequencing involves taking a single strand of the DNA to be sequenced and then synthesizing its complementary strand enzymatically. The pyrosequencing method is based on observing the activity of DNA polymerase, which is a DNA synthesizing enzyme, with another chemiluminescent enzyme. The single stranded DNA template is hybridized to a sequencing primer and incubated with the enzymes DNA polymerase, ATP sulfurylase, luciferase and apyrase, and with the substrates adenosine 5' phosphosulfate (APS) and luciferin. Synthesis of the complementary strand along the template DNA allows for sequencing of a single strand of DNA, one base pair at a time, by the detection of which base was actually added at each step.

The template DNA is immobile, and solutions of A, C, G, and T nucleotides are sequentially added and removed from the reaction. The templates for pyrosequencing can be made both by solid phase template preparation (streptavidin-coated magnetic beads) and enzymatic template preparation (apyrase+exonuclease). Specifically, the addition of one of the four deoxynucleoside triphosphates (dNTPs) (dATPaS, which is not a substrate for a luciferase, is added instead of dATP) initiates the next step. DNA polymerase incorporates the correct, complementary dNTPs onto the template. This base incorporation releases pyrophosphate (PPi) stoichiometrically. Then, ATP sulfurylase quantitatively converts PPi to ATP in the presence of adenosine 5' phosphosulfate. This ATP acts to catalyze the luciferase-mediated conversion of luciferin to oxyluciferin that generates visible light in amounts that are proportional to the amount of ATP. Light is produced only when the nucleotide solution complements the particular unpaired base of the template. The light output in the luciferase-catalyzed reaction is detected by a camera and analyzed in a program. The sequence of solutions which produce chemiluminescent signals allows the sequence determination of the template. Unincorporated nucleotides and ATP are degraded by the apyrase, and the reaction can restart with another nucleotide.

Illumina's™ Sequencing by Synthesis (SBS)

Illumina's™ sequencing by synthesis (SBS) technology with TruSeq technology supports massively parallel sequencing using a proprietary reversible terminator-based method that enables detection of single bases as they are incorporated into growing DNA strands.

A fluorescently labeled terminator is imaged as each dNTP is added and then cleaved to allow incorporation of the next base. Since all four reversible terminator-bound dNTPs are present during each sequencing cycle, natural competition minimizes incorporation bias. The end result is true base-by-base. Although this is similar to pyrosequencing, the differences between the platforms are noteworthy. The method described herein can be applied to any high-throughput sequencing technology, past, present or future. Pyrosequencing and SBS are merely examples and do not limit the application of the method in terms of sequencing.

Facilities with basic laboratory capabilities could be modified for use in microbial community analysis. Having an on-site sequencing capability will lower the amount of time from sample collection to data analysis and the production of useful results in a timely manner. Shortening the distance from sample collection to sequencing will alleviate the need for long-term preservation of the sample as well as diminishing the chances of losing samples. Sequencing can be performed on site when oil and gas fields are located in areas that lack the delivery infrastructure commonly available in many populated areas including but have basic lab capabilities: remote areas lacking well maintained roads, easy access to airports or landing strips, off-shore locations, drilling from vessels based platforms, or the presence of any other physical barriers that necessitate long transit times from the well to the lab.

Analysis of Sequencing Data

Generally, as the expense of sequencing decreases, the methods for comparing different communities based on the sequences they contain become increasingly important, and are often the bottleneck in obtaining insight from the data. Sequence data can be analyzed in a manner in which sequences are identified and labeled as being from a specific sample using the unique barcode introduced during library preparation, if barcodes are used, or sample identifiers will be associated with each run directly if barcodes are not used. Once sequences have been identified as belonging to a specific sample, the relationship between each pair of samples will be determined based on the distance between the collections of microbes present in each sample. In particular, techniques that allow for the comparison of many microbial samples in terms of the phylogeny of the microbes that live in them ("phylogenetic techniques") are often necessary. Such methods are particularly valuable as the gradients that affect microbial distribution are analyzed, and where there is a need to characterize many communities in an efficient and cost-effective fashion. Gradients of interest include different physical or chemical gradients in natural environments, such as temperature or nutrient gradients in certain industrial settings.

When comparing microbial communities, researchers often begin by determining whether groups of similar community types are significantly different. However, to gain a broad understanding of how and why communities differ, it is essential to move beyond pairwise significance tests. For example, determining whether differences between communities stem primarily from particular lineages of the phylogenetic tree, or whether there are environmental factors (such as temperature, salinity, or acidity) that group multiple communities together is pivotal to an analysis. The analysis systems described herein are merely examples and are not limiting. Any methods which will distill massive data sets from raw sequences to human-interpretable formats, for example, 2-D or 3-D ordination plots, supervised learning for predictive modeling, or more traditional statistical significance testing, allowing for pattern elucidation and recognition, will be used.

QIIME

After DNA sequence data is obtained the bioinformatics stages begin. This includes barcode decoding (demultiplexing), sequence quality control, "upstream" analysis steps (including clustering of closely related sequences and phylogenetic tree construction), and "downstream" diversity analyses, visualization, and statistics. All of these steps are currently facilitated by the Quantitative Insights Into Microbial Ecology (QIIME, www.qiime.org) open source software package, which is the most widely used software for the analysis of microbial community data generated on high-throughput sequencing platforms. QIIME was initially designed to support the analysis of marker gene sequence data, but is also generally applicable to "comparative-omics" data (including but not limited to metabolomics, metatranscriptomics, and comparative human genomics).

QIIME is designed to take users from raw sequencing data (for example, as generated on the Illumina™ and 454™ platforms) though the processing steps mentioned above, leading to quality statistics and visualizations used for interpretation of the data. Because QIIME scales to billions of sequences and runs on systems ranging from laptops to high-performance computer clusters, it will continue to keep pace with advances in sequencing technologies to facilitate characterization of microbial community patterns ranging from normal variations to pathological disturbances in many human, animal and environmental ecosystems.

For microbiome data analysis, the following steps will be taken. Unless otherwise noted, the steps will be performed with QIIME. However, other such systems may be used and the scope of protection afforded to the present inventions is not in anyway limited to, or dependent upon, the use of QIIME.

Compiling the Sample Metadata Mapping File

The first step in the bioinformatics stage of a microbial community analysis study is to consolidate the sample metadata in a spreadsheet. The sample metadata is all per-sample information, including technical information such as the barcode assigned to each sample, and "environmental" metadata. This environmental metadata will differ depending on the types of samples that are being analyzed. If, for example, the study is of microbial communities in soils, the pH and latitude where the soil was collected could be environment metadata categories. Alternatively, if the samples are of the human microbiome, environmental metadata may include subject identifiers and collection times. This spreadsheet will be referred to as the sample metadata and/or mapping file in the following sections. An example sample metadata mapping file is provided as Table 1.

TABLE 1

Sample Metadata Mapping File

| SampleID | BarcodeSequence | LinkerPrimerSequence | TEXTURE | DEPTH | TOT_ORG | SPECIFIC_LOCATION |
|---|---|---|---|---|---|---|
| IT2 | ACGTGCCGTAGA | CATGCTGCCTCCCGTAGGAGT | loamy sand | 0-0.05 | 39.1 | Itasca Lake State Park, MN USA |
| HI3 | ACGCTATCTGGA | CATGCTGCCTCCCGTAGGAGT | loamy sand | 0-0.05 | 182.4 | Kohala Peninsula, HI USA |
| MD2 | ACTCGATTCGAT | CATGCTGCCTCCCGTAGGAGT | sandy loam | 0-0.05 | 4.2 | Mojave Desert, CA USA |
| CA1 | ACACGAGCCACA | CATGCTGCCTCCCGTAGGAGT | silt loam | 0-0.05 | 16.7 | Cedar Mt. AZ, USA |
| PE5 | AGACTGCGTACT | CATGCTGCCTCCCGTAGGAGT | clay loam | 0-0.05 | 93.6 | Manu National Park, Peru |
| CO1 | ACATGATCGTTC | CATGCTGCCTCCCGTAGGAGT | sand | 0-0.05 | 15.9 | Fort Collins, CO USA |
| DF3 | ACCGCAGAGTCA | CATGCTGCCTCCCGTAGGAGT | loamy sand | 0-0.05 | 17 | Duke Forest, NC USA |
| PE1 | ACTTGTAGCAGC | CATGCTGCCTCCCGTAGGAGT | sandy loam | 0-0.05 | 134.2 | Manu National Park, Peru |
| SP2 | AGCGCTGATGTG | CATGCTGCCTCCCGTAGGAGT | loamy sand | 0-0.05 | 81 | Sequoia National Park, CA USA |
| CO3 | ACATTCAGCGCA | CATGCTGCCTCCCGTAGGAGT | sandy loam | 0-0.05 | 8.2 | Shortgrass Steppe LTER, CO USA |
| SA2 | AGATCGGCTCGA | CATGCTGCCTCCCGTAGGAGT | sand | 0-0.05 | 25 | Sunset Crater, AZ USA |
| CM1 | ACATCACTTAGC | CATGCTGCCTCCCGTAGGAGT | silty clay | 0-0.05 | 29.9 | Clymer Meadow Preserve, TX USA |
| LQ2 | ACTCACGGTATG | CATGCTGCCTCCCGTAGGAGT | silty clay loam | 0-0.05 | 41.1 | Luquillo LTER, Puerto Rico |
| SR2 | AGCTATCCACGA | CATGCTGCCTCCCGTAGGAGT | sandy loam | 0-0.05 | 14.6 | Sedgwick Reserve, CA USA |
| CR1 | ACCACATACATC | CATGCTGCCTCCCGTAGGAGT | loam | 0-0.05 | 28.3 | Coffey Ranch, TX USA |
| VC1 | AGGTGTGATCGC | CATGCTGCCTCCCGTAGGAGT | sandy loam | 0-0.05 | 56.7 | Valles Caldera, NM USA |
| IE2 | ACGTCTGTAGCA | CATGCTGCCTCCCGTAGGAGT | sandy loam | 0-0.05 | 40.7 | Institute for Ecosystem Studies, N |
| RT2 | AGAGTCCTGAGC | CATGCTGCCTCCCGTAGGAGT | silty clay loam | 0-0.05 | 37.5 | USDA Grassland Research Center, |
| BB1 | AAGAGATGTCGA | CATGCTGCCTCCCGTAGGAGT | sandy loam | 0-0.05 | 12.84 | Bear Brook, ME |
| CC1 | ACACTAGATCCG | CATGCTGCCTCCCGTAGGAGT | sand | 0-0.05 | 19.1 | Cedar Creek LTER, MN USA |
| TL2 | AGGACGCACTGT | CATGCTGCCTCCCGTAGGAGT | silt loam | 0-0.05 | 158.3 | Toolik Lake LTER, AK USA |
| PE6 | AGAGAGCAAGTG | CATGCTGCCTCCCGTAGGAGT | clay | 0-0.05 | 33.4 | Manu National Park, Peru |
| HI1 | ACGCGATACTGG | CATGCTGCCTCCCGTAGGAGT | loam | 0-0.05 | 11.4 | Kohala Peninsula, HI USA |
| PE7 | AGAGCAAGAGCA | CATGCTGCCTCCCGTAGGAGT | silty clay | 0-0.05 | 63.8 | Manu National Park, Peru |

TABLE 1-continued

Sample Metadata Mapping File

| SampleID | BarcodeSequence | LinkerPrimerSequence | TEXTURE | DEPTH | TOT_ORG | SPECIFIC_LOCATION |
|---|---|---|---|---|---|---|
| BF1 | AATCAGTCTCGT | CATGCTGCCTCCCGTAGGAGT | loam | 0-0.05 | 64.4 | Bousson Forest, PA, USA |
| TL1 | AGCTTGACAGCT | CATGCTGCCTCCCGTAGGAGT | loam | 0-0.05 | 70.2 | Toolik Lake LTER, AK USA |
| KP1 | ACTACAGCCTAT | CATGCTGCCTCCCGTAGGAGT | silt loam | 0-0.05 | 61.2 | Konza Prairie LTER, KS USA |
| CL3 | ACAGTGCTTCAT | CATGCTGCCTCCCGTAGGAGT | loamy sand | 0-0.05 | 12.1 | Calhoun Experimental Forest, SC I |

Barcode Decoding and Quality Control

Next, in a combined analysis step, sequence barcodes will be read to identify the source sample of each sequence, poor quality regions of sequence reads will be trimmed, and poor quality reads will be discarded. These steps will be combined for computational efficiency. The features included in quality filtering include whether the barcode will unambiguously be mapped to a sample barcode, per-base quality scores, and the number of ambiguous (N) base calls. The default settings for all quality control parameters in QIIME will be determined by benchmarking combinations of these parameter on artificial (i.e., "mock") community data, where microbial communities were created in the lab from known concentrations of cultured microbes, and the composition of the communities is thus known in advance.

Sequence Clustering or "OTU Picking"

After mapping sequence reads to samples and performing quality control, sequences will be clustered into OTUs (Operational Taxonomic Units) based on sequence similarity. This is typically the most computationally expensive step in microbiome data analysis, and will be performed to reduce the computational complexity at subsequent steps. The assumption made at this stage is that organisms that are closely related, as determined by the similarity of their marker gene sequences, are functionally similar. Highly similar sequences (e.g., those that are greater than 97% identical to one another, or other value that is determined to be most efficient and meaningful) will be clustered, the count of sequences that are contained in each cluster will be retained, and then a single representative sequence from that cluster will be chosen for use in downstream analysis steps such as taxonomic assignment and phylogenetic tree construction. This process of clustering sequences is referred to as OTU picking, where the OTUs (i.e., the clusters of sequences) are considered to approximately represent taxonomic units such as species.

There are three high-level strategies for OTU picking, each of which is implemented in QIIME. In a do novo OTU picking process, reads will be clustered against one another without any external reference sequence collection. The QIIME workflow pick_de_novo_otus.py is the primary interface for de novo OTU picking in QIIME, and includes taxonomy assignment, sequence alignment, and tree-building steps. A benefit of de novo OTU picking is that all reads are clustered. A drawback is that there is no existing support for running the clustering in parallel, so it can be too slow to apply to large datasets (e.g., more than 10 million reads), although other portions of the workflow are parallelized. De novo OTU picking must be used if there is no reference sequence collection to cluster against, for example because an infrequently used marker gene is being used. De novo OTU picking cannot be used if the comparison is between non-overlapping amplicons, such as the V2 and the V4 regions of the 16S rRNA gene or for very large data sets, like a full HiSeq™ 2000 run. Although technically, de novo OTU picking can be used for very large data sets, the program would take too long to run to be practical.

In a closed-reference OTU picking process, reads will be clustered against a reference sequence collection and any reads that do not hit a sequence in the reference sequence collection are excluded from downstream analyses. pick_closed_reference_otus.py is the primary interface for closed-reference OTU picking in QIIME. If the user provides taxonomic assignments for sequences in the reference database, those are assigned to OTUs. Closed-reference OTU picking must be used if non-overlapping amplicons, such as the V2 and the V4 regions of the 16S rRNA, will be compared to each other. The reference sequences must span both of the regions being sequenced. Closed-reference OTU picking cannot be used if there is no reference sequence collection to cluster against, for example because an infrequently used marker gene is being used. A benefit of closed-reference OTU picking is speed in that the picking is fully parallelizable, and therefore useful for extremely large data sets. Another benefit is that because all OTUs are already defined in the reference sequence collection, a trusted tree and taxonomy for those OTUs may already exist. There is the option of using those, or building a tree and taxonomy from the sequence data. A drawback to reference-based OTU picking is that there is an inability to detect novel diversity with respect to the reference sequence collection. Because reads that do not hit the reference sequence collection are discarded, the analyses only focus on the diversity that is already known. Also, depending on how well-characterized the environment is, a small fraction of the reads (e.g., discarding 1-10% of the reads is common for 16S-based human microbiome studies, where databases like Greengenes cover most of the organisms that are typically present) or a large fraction of your reads (e.g., discarding 50-80% of the reads has been observed for "unusual" environments like the Guerrero Negro microbial mats) may be discarded.

The third method widely used is an open-reference OTU picking process, reads will be clustered against a reference sequence collection and any reads which do not hit the reference sequence collection are subsequently clustered de novo. Using appropriate parameters the workflow pick_de_novo_otus.py (despite the name) is the primary interface for open-reference OTU picking in QIIME, and includes taxonomy assignment, sequence alignment, and tree-building steps. Open-reference OTU picking with pick_de_novo_otus.py is the preferred strategy for OTU picking. Open-reference OTU picking cannot be used for comparing non-overlapping amplicons, such as the V2 and the V4 regions of the 16S rRNA, or when there is no reference sequence collection to cluster against, for example because an infrequently used marker gene is being used. A benefit of open-reference OTU picking is that all reads are clustered. Another benefit is speed. Open-reference OTU picking is partially run in parallel. In particular, if the script is used in a subsampled manner, open reference OTU picking process implemented in pick_de_novo_otus.py is much faster than a the de novo OTU picking strategy described above as some strategies are applied to run several pieces of the workflow in parallel. However, a drawback of open-reference OTU picking is also speed. Some steps of this workflow run serially. For data sets with a lot of novel diversity with respect to the reference sequence collection, this can still take days to run.

Generally, uclust is the preferred method for performing OTU picking. QIIME's uclust-based open reference OTU picking protocol will be used when circumstances allow (i.e., when none of the cases above, where open reference OTU picking is not possible, apply).

The OTU-picking protocol described above is used for processing taxonomic marker gene sequences such as those from the 16S rRNA, ITS and LSU gene as well as other marker genes amplification sequencing. In that case, the sequences themselves are not used to identify biological functions performed by members of the microbial community; they are instead used to identify which kinds of organisms are present, as well as the abundances of those organisms.

In the case of shotgun metagenomic sequencing, the data obtained are random fragments of all genomic DNA present in a given microbiome. These can be compared to reference genomes to identify the types of organisms present in a manner similar to marker gene sequences, but they may also be used to infer biological functions encoded by the genomes of microbes in the community. Typically this is done by comparing them to reference genomes and/or individual genes or genetic fragments that have been annotated for functional content. In the case of shotgun metatranscriptomic sequencing, the data obtained are similar to that for shotgun metatranscriptomic sequencing except that the RNA rather than the DNA is used, and physical or chemical steps to deplete particular classes of sequence such as eukaryotic messenger RNA or ribosomal RNA are often used prior to library construction for sequencing. In the case of shotgun metaproteomics, protein fragments are obtained and matched to reference databases. In the case of shotgun metabolomics, metabolites are obtained by biophysical methods including nuclear magnetic resonance or mass spectrometry. In all of these cases, some type of coarse-graining of the original data equivalent to OTU picking to identify biologically relevant features is employed, and a biological observation matrix as described above relating either the raw or coarse-grained observations to samples is obtained. The steps downstream from the Biological Observation Matrix, including the construction of distance matrices, taxon or functional tables, and industry-specific, actionable models from such data, are conceptually equivalent for each of these datatypes and are within the scope of the present Invention.

Choosing OTU Representative Sequences, Assigning Taxonomy, Aligning Sequences, and Constructing Phylogenetic Trees Next, the centroid sequence in each OTU will be selected as the representative sequence for that OTU. The centroid sequence will be chosen so that all sequences are within the similarity threshold to their representative sequence, and the centroid sequences are specifically chosen to be the most abundant sequence in each OTU.

The OTU representative sequences will next be aligned using an alignment algorithm such as the PyNAST software package. PyNAST is a reference-based alignment approach, and is chosen because it achieves similar quality alignments to non-reference-based alignment approaches (e.g., muscle), where quality is defined as the effect of the alignment algorithm choice on the results of phylogenetic diversity analyses, but is easily run in parallel, which is not the case for non-reference-based alignment algorithms.

Once a PyNAST alignment is obtained, positions that mostly contain gaps, or too high or too low variability, will be stripped to create a position-filtered alignment. This position-filtered alignment will be used to construct a phylogenetic tree using FastTree. This tree relates the OTUs to one another, will be used in phylogenetic diversity calculations (discussed below), and is referred to below as the OTU phylogenetic tree.

In addition to being aligned, all OTU representative sequences will have taxonomy assigned to them. This can be performed using a variety of techniques, though our currently preferred approach is the uclust-based consensus taxonomy assigner implemented in QIIME. Here, all representative sequences (the "query" sequences) are queried against a reference database (e.g., Greengenes, which contains near-full length 16S rRNA gene sequences with human-curated taxonomic assignments; UNITE database for ITS; SILVA for 18S rRNA) with uclust. The taxonomy assignments of the three best database hits for each query sequences are then compared, and a consensus of those assignments is assigned to the query sequence.

Constructing a Biological Observation Matrix (BIOM) Table

The last of the "upstream" processing steps is to create a Biological Observation Matrix (BIOM) table, which contains counts of OTUs on a per-sample basis and the taxonomic assignment for each OTU. This table, which will be referred to as the BIOM table, the OTU phylogenetic tree constructed above, and the sample metadata mapping file will be the data required for computing phylogenetic diversity metrics in the next steps, and for doing visual and statistical analysis based on these diversity metrics. Although the BIOM is a specific file format for the table with OTU counts on a per-table basis, other file formats are also possible as well.

Analysis of Microbial Communities

Once a BIOM table, an OTU phylogenetic tree, and a sample metadata mapping file are compiled, the microbial communities present in each sample will be analyzed and compared (n-dimensional plot). These analyses include, but are not limited to, summarizing the taxonomic composition of the samples, understanding the "richness" and "evenness" of samples (defined below), understanding the relative similarity between communities (or samples), and identifying organisms or groups of organisms that are significantly different across community types. The different types of analysis on soil microbial community data will be illustrated in Example 17.

Taxonomic Composition of Samples

The taxonomic composition of samples is often something that researchers are most immediately interested in. This can be studied at various taxonomic levels (e.g., phylum, class, species) by collapsing OTUs in the BIOM table based on their taxonomic assignments. The abundance of each taxon on a per-sample basis is then typically presented in bar charts, area charts or pie charts, though this list is not comprehensive, FIG. 14 contains an area chart illustrating the phylum level composition of 88 soil samples spanning a pH gradient.

Figure 14:
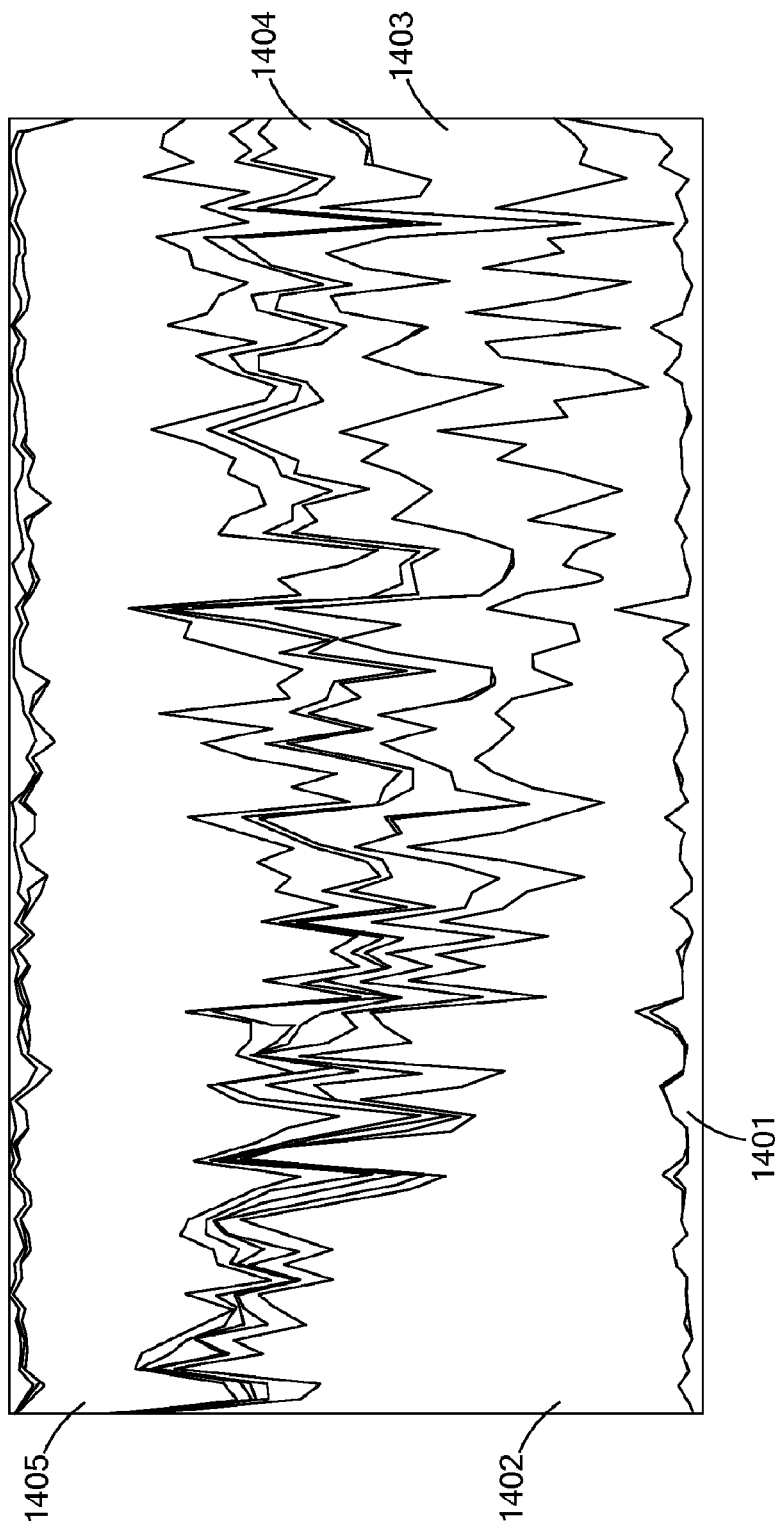
FIG. 14 is an illustration of an embodiment of microbiome composition presented in accordance with an embodiment of the present inventions.

FIG. 14 is an illustration of an embodiment of microbiome composition. The y-axis is relative abundance of specific microbial phyla (a high-level taxonomic group; each phylum contains many bacterial species); the x-axis represents soil pH; and the colors (grey scale and simplified for purposes of patent figures) present different bacterial phyla.

For example these phyla include:
k_Bacteria;p_AD3
k_Bacteria;p_Acidobacteria
k_Bacteria;p_Actinobacteria
k_Bacteria;p_Armatimonadetes
k_Bacteria;p_BHI80-139
k_Bacteria;p_BRCI
k_Bacteria;p_Bacteroidetes
k_Baeteria;p_Chlorobi
k_Bacteria;p_Chloroflexi
k_Bacteria;p_Cyanobacteria
k_Bacteria;p_Busimicrobia
k_Bacteria;p_FBP
k_Bacteria;p_FCPU426
k_Bacteria;p_Fibrobacteres
k_Bacteria;p_Firmicutes
k_Bacteria;p_GAL15
k_Bacteria;p_GN02
k_Bacteria;p_Gemmatimonadetes
k_Bacteria;p_Kazan-3B-28
k_Bacteria;p_MVP-21
k_Bacteria;p_NC10
k_Bacteria;p_NKB19
k_Bacteria;p_Nitrospirae
k_Bacteria;p_ODI
k_Bacteria;p_OPII
k_Bacteria;p_0P3
k_Bacteria;p_0P8
k_Bacteria;p_Planctomycetes
k_Bacteria;p_Proteobacteria
k_Bacteria;p_SRI
k_Bacteria;p_Spirochaetes
k_Bacteria;p_TM6
k_Bacteria;p_TM7
Unassigned;Other
k_Bacteria;Other
k_Bacteria;p_

As seen in FIG. 14, each microbial taxon is denoted by a different color (e.g., area, 1401, 1402, 1403, 1404, 1405 for purposes of patent figures), with the x-axis representing increasing pH and the y-axis representing relative abundance. Some taxa change in a consistent way from low to high pH, for example, Acidobacteria is represented in area 1402. These consistent changes can drive the pattern in PCoA.

Within-Sample Diversity (Richness and Evenness):

Alpha diversity refers to diversity of single samples (i.e., within-sample diversity), including features such as taxonomic richness and evenness. There are a number of different ways to measure alpha diversity, including but not limited to: Chao 1, Simpson's Diversity Index and the Shannon Index. The species richness is a measure of the number of different species of microbes in a given sample. Typically these measures will be performed after rarefaction, or the random subsampling of a specified number of sequences. Species evenness refers to how close the relative abundance of a set of species are in a particular area or environment.

Measures of alpha diversity (or, a measure of within-sample diversity) have a long history in ecology. Alpha diversity measures have been shown to differ in different types of communities, for example, from different human body habitats. For instance, skin-surface bacterial communities have been found to be significantly more rich (i.e., containing more species; increased diversity) in females than in males, and at dry sites rather than sebaceous sites, and the gut microbiome of lean individuals have been found to be significantly more rich than those of obese individuals.

Figure 10:
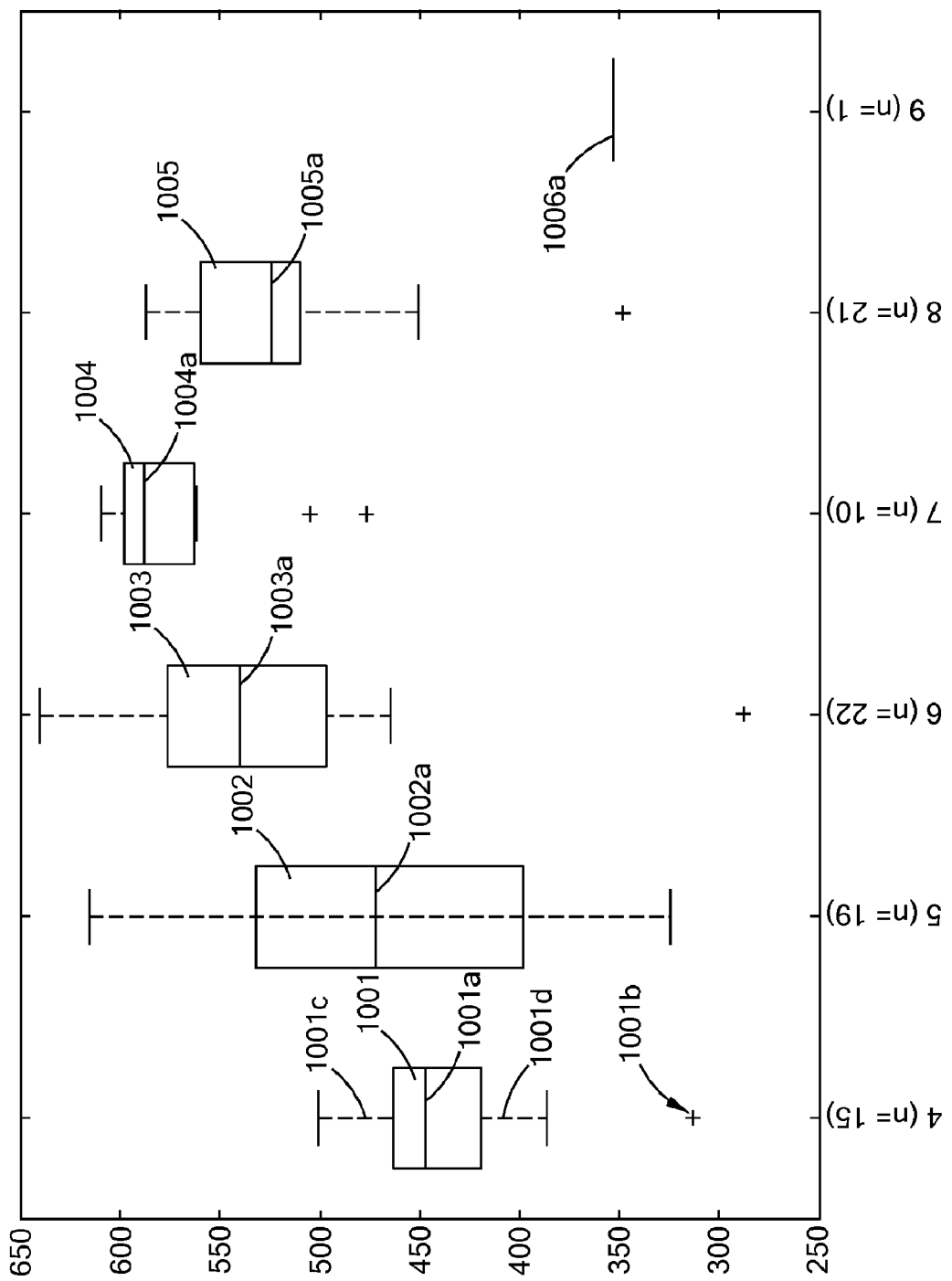
FIG. 10 is chart of an embodiment of the association of environmental parameters with microbial composition in accordance with the present inventions.
Figure 11:
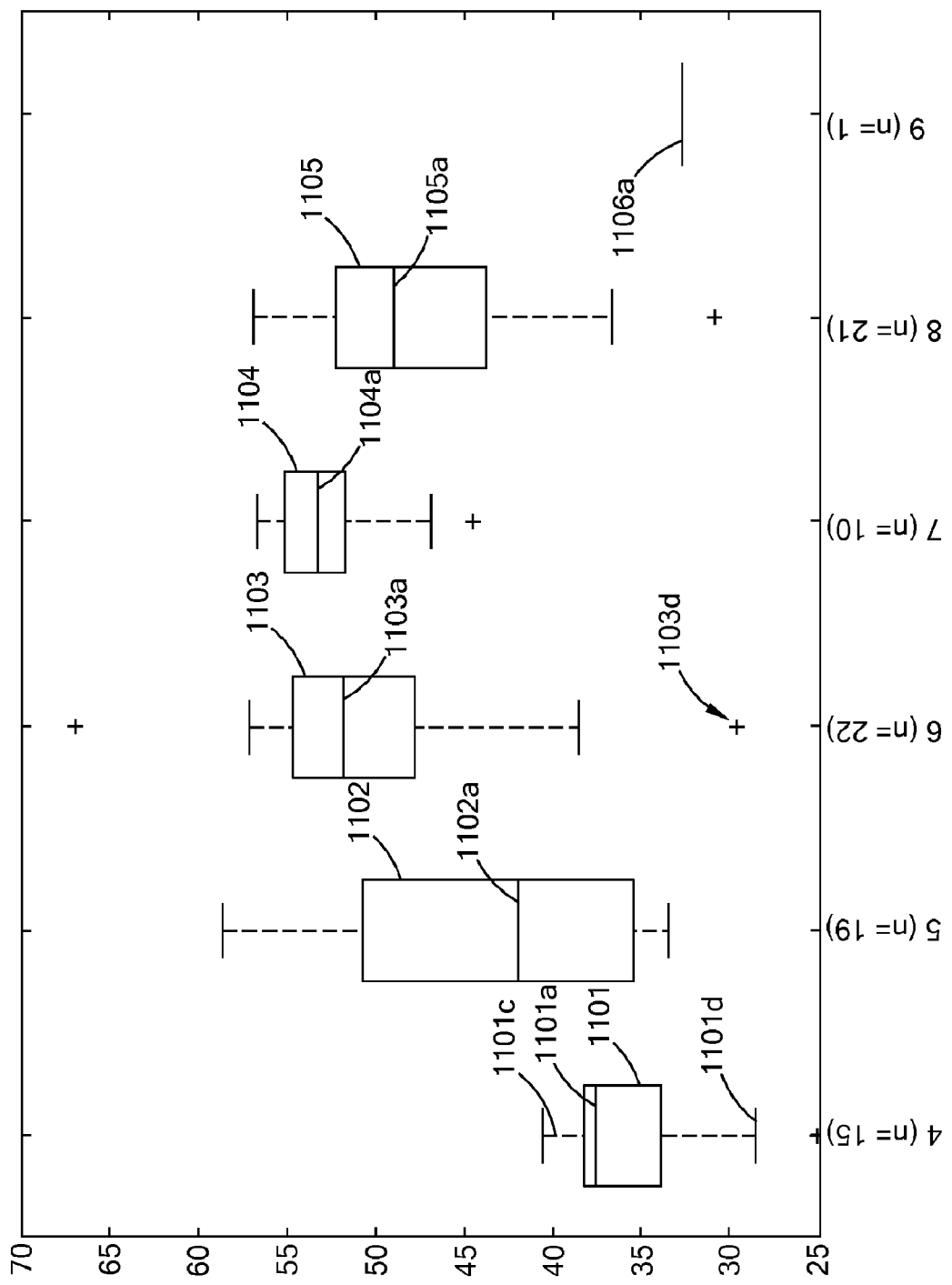
FIG. 11 is a chart of an embodiment of the association of environmental parameters with microbial composition in accordance with the present inventions.

FIGS. 10 and 11 illustrate ways of viewing alpha diversity.

In this figures, two indices will be used to compare community-level bacterial richness across 88 different soils. First the number of observed OTW will be computed, based on OTUs clustered with an open reference OTU picking protocol at the 97% sequence similarity level. The number of observed OTUs are shown in FIG. 10. The legend for FIG. 10 is the x axis is Soil pH; and the y-axis is Observed OTUs. The x-axis represents the number of OTUs observed (a measure of "alpha diversity"); the x-axis represents the pH of a soil sample; and each box 1001, 1002, 1003, 1004, 1005, represents the distribution of number of OTUs observed in soils of the corresponding pH. The rectangles extend from the lower to upper quartile values of the data, with a lines 1001a, 1002a, 1003a, 1004a, 1005a, 1006a (pH with no distribution, n=1), at the median. The whiskers (dashed lines, e.g., 1001c, 1001d) extend from the box to 1.5 times the interquartile range. Outliers (those that are outside of 1.5 times the interquartile range) are the pluses, e.g., 1001b, past the end of the whiskers. This plot illustrates that the number of OTUs peaks at neutral pH. This index of diversity is limited in that it characterizes diversity at only a single level of taxonomic resolution. Diversity will also be computed using Faith's index of phylogenetic diversity (Faith's PD), which provides an integrated index of the phylogenetic breadth contained within each community.

An example of the computation of the phylogenetic diversity is shown in FIG. 11. Thus, FIG. 11 is an embodiment of a graph of an embodiment of the association of environmental parameters with microbial composition across 88 soil samples included in a global survey of soil microbial diversity. The legend for FIG. 11 is the x-axis is Soil pH; and the y-axis is Phylogenetic Diversity. The y-axis represents the phylogenetic diversity observed (a measure of "alpha diversity"); the x-axis represents the pH of a soil sample; and each box 1101, 1102, 1103, 1104, 1105, represents the distribution of the observed phylogenetic diversity in soils of the corresponding pH. The rectangles extend from the lower to upper quartile values of the data, with a lines 1101a, 1102a, 1103a, 1104a, 1105a, 1106a (pH with no distribution, n=1), at the median. The whiskers (dashed lines, e.g., 1101c, 1101d) extend from the box to 1.5 times the interquartile range. Outliers (those that are outside of 1.5 times the interquartile range) are the pluses, e.g., 1103d, past the end of the whiskers. As in FIG. 10, this plot illustrates that the phylogenetic diversity peaks at neutral pH.

Here we show that the degree of phylogenetic diversity in a sample (a phylogeny-aware measure of richness) changes with soil pH, for 88 soils ranging from pH around 6.5 through 9.5, with a peak in richness around neutral pH of 7. These data suggest that in some cases alpha diversity will be useful input features for building predictive models via supervised classifiers.

In both cases, the diversity metrics will be calculated for a randomly selected subset of the same number of sequences per soil sample, here 934, because diversity is unavoidably correlated with the number of sequences collected. The results of these analyses are presented in FIGS. 10-11, and both richness metrics show similar patterns in this specific case. By using a set number of sequences, general diversity patterns will be compared even if it is highly unlikely that the full extent of diversity was surveyed in each community.

Between-Sample Diversity (UniFrac and Principal Coordinates Analysis)

Generally the primary question of interest when beginning a survey of new microbial community types is What environmental features are associated with differences in the composition of microbial communities? This is a question of between-sample (or "beta") diversity. Beta diversity metrics provide a measure of community dissimilarity, allowing investigators to determine the relative similarity of microbial communities. Metrics of beta diversity are pairwise, operating on two samples at a time.

The difference in overall community composition between each pair of samples can be determined using the phylogenetically-aware UniFrac distance metric, which allows researchers to address many of these broader questions about the composition of microbial communities. UniFrac calculates the fraction of branch length unique to a sample across a phylogenetic tree constructed from each pair of samples. In other words, the UniFrac metric measures the distance between communities as the percentage of branch length that leads to descendants from only one of a pair of samples represented in a single phylogenetic tree, or the fraction of evolution that is unique to one of the microbial communities. Phylogenetic techniques for comparing microbial communities, such as UniFrac, avoid some of the pitfalls associated with comparing communities at only a single level of taxonomic resolution and provide a more robust index of community distances than traditional taxon-based methods, such as the Jaccard and Sorenson indices. Unlike phylogenetic techniques, species-based methods that measure the distance between communities based solely on the number of shared taxa do not consider the amount of evolutionary divergence between taxa, which can vary widely in diverse microbial populations. Among the first applications of phylogenetic information to comparisons of microbial communities were the Phylogenetic (P)-test and the $F_{ST}$ test. Pain:vise significance tests are limited because they cannot be used to relate many samples simultaneously. Although phylogenetically-aware techniques such as UniFrac offer significant benefits, techniques lacking phylogenetic awareness can also be implemented with success: after an alternative distance metric (e.g. Bray-Curtis, Jensen-Shannon divergence) has been applied, the resulting inter-sample distance matrix is processed in the same way as a UniFrac distance matrix as described below.

QIIME implements the UniFrac metric and uses multivariate statistical techniques to determine whether groups of microbial communities are significantly different. When studying a set of n microbial communities, the UniFrac distances between all pairs of communities are computed to derive a distance matrix (using UniFrac or other distances) for all samples. This will be an n x n matrix, which is symmetric (because the distance between sample A and sample B is always equal to the distance between sample B and sample A) and will have zeros on the diagonal (because the distance between any sample and itself is always zero). For any reasonably larger value of n (e.g., n>5) it becomes difficult to interpret patterns of beta diversity from a distance matrix directly (FIG. 9). FIG. 9 shows matrix formed from unweighted UniFrac distances between the first 12 of the 88 soil samples included in the analysis in Example 9. As the number of samples increases beyond just a few (e.g., five) samples, it becomes very difficult to identify meaningful patterns from distance matrices alone.

Ordination techniques, such as principal coordinates analysis (PCoA) and non-metric multidimensional scaling (NMDS), together with approximations to these techniques that reduce computational cost or improve parallelism, will be used to summarize these patterns in two or three dimensional scatter plots. The patterns can also be represented in two dimensions using, for example, using line graph, bar graphs, pie charts, Venn diagrams, etc., as a non-exhaustive list. The patterns can also be represented in three dimensions using, for example, wire frame, ball and stick models, 3-D monitors, etc. This list is also non-exhaustive and does not limit the 2-D or 3-D forms by which the data can be represented.

PCoA is a multivariate analysis technique for finding the most important orthogonal axes along which samples vary. Distances are converted into points in a space with a number of dimensions one less than the number of samples. The principal coordinates or axes, in descending order, describe how much of the variation (technically, the inertia) each of the axes in this new space explains. The first principal coordinate separates the data as much as possible; the second principal coordinate provides the next most separation along an orthogonal axis, and so forth. QIIME returns information on all principal axes in a data table. It also allows easy visualization of that data in interactive scatter plots that allow users to choose which principal components to display. The points (each representing a single sample) are marked with colored symbols, (grey scale symbols are used for the purposes of the patent figures) and users can interactively change the colors of the points to detect associations between sample microbial composition and sample metadata. PCoA often reveals patterns of similarity that are difficult to see in a distance matrix (see, e.g., FIGS. 12 and 13), and the axes along which variation occurs can sometimes be correlated with environmental variables such as pH or temperature. Industrial variables, or control data, can include presence of oil, pressure, viscosity, etc. These control data can be filtered or removed in order to observe other control data factors to visualize possible patterns.

New ways of exploring and visualizing results and identifying meaningful patterns are increasingly important as the size and complexity of microbial datasets rapidly increase. QIIME 1.8.0 (released in December 2013) introduces several powerful tools to assist in visualizations of the results of PCoA, primarily the Emperor 3D scatter plot viewer (https://github.com/qiime/emperor). This includes (i) the ability to color large collections of samples using different user-defined subcategories (for example, coloring environmental samples according to temperature or pH), (ii) automatic scaled/unscaled views, which accentuate dimensions that explain more variance, (iii) the ability to interactively explore tens of thousands of points (and user-configurable labels) in 3D, and (iv) parallel coordinates displays that allow the dimensions that separate particular groups of environments to be readily identified.

The significance of patterns identified in PCoA can be tested with a variety of methods. The significance of the clusters identified by UniFrac can be established using Monte Carlo based t-tests, where samples are grouped into categories based on their metadata, and distributions of distances within and between categories are compared. For example, if a relationship using PCoA is noted between microbial communities in soils from an oil well and soils unassociated with oil, the distribution of UniFrac distances between soils from the same group can be compared to those between soils from different groups by computing a t-score (the actual t-score). The sample labels (oil and not oil) can then be randomly shuffled 10,000 times, and a t-score calculated for each of these randomized data sets (the randomized t-scores). If the oil soils and non-oil soils are significantly different from one another in composition, the actual t-score should higher than the vast majority of the randomized t-scores. A p-value will be computed by dividing the number of randomized t-scores that are better than the actual t-score by 9999. The Monte Carlo simulations described here will be run in parallel, and are not limited to pairs of sample categories, so they support analysis of many different sample types.

If the samples fall along a gradient that is correlated with some environmental metadata or variable (e.g., pH, salinity, temperature, geochemical measures, etc.), rather than clustering into discrete groups (as described above), there are alternative approaches to testing for statistical significance. For example, if pH appears to be correlated with the principal coordinate 1 (PC1) values in a PCoA plot, an empirical (as is sometimes defined in a broader category known as, Monte Carlo simulation)-based Pearson or Spearman correlation test will be performed. Here, pH and PC1 will be tested to, for example, compute a Spearman rho value. The labels of the samples will again be shuffled 10,000 times and rho computed for each randomized data set. The p-value for the pH versus PC1 correlation will then be the number of randomized rho values that are higher than the actual rho value divided by 9999.

Identifying Features That are Predictive of Environment Characteristics (i.e., Sample Metadata)

Supervised classification is a machine learning approach for developing predictive models from training data. Each training data point consists of a set of input features, for example, the relative abundance of taxa, and a qualitative dependent variable giving the correct classification of that data point. In microbiome analysis, such classifications might include soil nutrients, the presence of oil, predominant weather patterns, disease states, therapeutic results, or forensic identification. The goal of supervised classification is to derive some function from the training data that can be used to assign the correct class or category labels to novel inputs (e.g. new samples), and to learn which features, for example, taxa, discriminate between classes. Common applications of supervised learning include text classification, microarray analysis, and other bioinformatics analyses. For example, when microbiologists use the Ribosomal Database Project website to classify 16S rRNA gene sequences taxonomically, a form of supervised classification is used.

The primary goal of supervised learning is to build a model from a set of categorized data points that can predict the appropriate category membership of unlabeled future data. The category labels can be any type of important metadata, such as pressure, viscosity, pH or temperature. The ability to classify unlabeled data is useful whenever alternative methods for obtaining data labels are difficult or expensive.

This goal of building predictive models is very different from the traditional goal of fitting an explanatory model to one's data set. The concern is less with how well the model fits our particular set of training data, but rather with how well it will generalize to novel input data. Hence, there is a problem of model selection. A model that is too simple or general is undesirable because it will fail to capture subtle, but important information about the independent variables (underfitting). A model that is too complex or specific is also undesirable because it will incorporate idiosyncrasies that are specific only to the particular training data (overfitting). The expected prediction error (EPE) of the model on future data must be optimized.

When the labels for the data are easily obtained, a predictive model is unnecessary. In these cases, supervised learning will still be useful for building descriptive models of the data, especially in data sets where the number of independent variables or the complexity of their interactions diminishes the usefulness of classical univariate hypothesis testing. Examples of this type of model can be seen in the various applications of supervised classification to microarray data, in which the goal is to identify a small, but highly predictive subset of the thousands of genes profiled in an experiment for further investigation. In microbial ecology, the analogous goal is to identify a subset of predictive taxa. In these descriptive models, accurate estimation of the EPE is still important to ensure that the association of the selected taxa with the class labels is not just happenstance or spurious. This process of finding small but predictive subsets of features, called feature selection, is increasingly important as the size and dimensionality of microbial community analyses continue to grow.

A common way to estimate the EPE of a particular model is to fit the model to a subset (e.g., 90%) of the data and then test its predictive accuracy on the other 10% of the data. This can provide an idea of how well the model would perform on future data sets if the goal is to fit it to the entire current data set. To improve the estimate of the EPE, this process will be repeated a number of times so that each data point is part of the held-out validation data once. This procedure, known as cross-validation, will allow for the comparison of models that use very different inner machinery or different subsets of input features. Of course if many different models are tried and one provides the lowest cross-validation error for the entire data set is selected, it is likely that the reported EPE will be too optimistic. This is similar to the problem of making multiple comparisons in statistical inference; some models are bound to fortuitously match a particular data set. Hence, whenever possible, an entirely separate test set will be held out for estimating the EPE of the final model, after performing model selection.

Even if the method for selecting the best parameters or degree of complexity for a particular kind of model is determined, there is still a general challenge of picking what general class of models is most appropriate for a particular data set. The core aspect of choosing the right models for microbiome classification is to combine the knowledge of the most relevant constraints (e.g., data sparseness) inherent in the data with the understanding of the strengths and weaknesses of various approaches to supervised classification. If it is understood what structures will be inherent in the data, then models that take advantage of those structures will be chosen. For example, in the classification of microbiomes, methods that can model nonlinear effects and complex interactions between organisms will be desired. In another example, the highly diverse nature of many microbial communities on the human body, models designed specifically to perform aggressive feature selection when faced with high-dimensional data will be most appropriate. Specialized generative models will be designed to incorporate prior knowledge about the data as well as the level of certainty about that prior knowledge. Instead of learning to predict class labels based on input features, a generative model will learn to predict the input features themselves. In other words, a generative model will learn what the data "looks like," regardless of the class labels. One potential benefit of generative models such as topic models and deep-layered belief nets, will be that they can extract useful information even when the data are unlabeled. The ability to use data from related experiments to help build classifiers for one's own labeled data will be important as the number of publicly available microbial community data sets continues to grow.

Machine learning classification techniques will be applied to many types of microbial community data, for example, to the analysis of soil and sediment samples. For the soil and sediment samples, the samples will be classified according to environment type using support vector machines (SVMs) and k-nearest neighbors (KNN). Supervised learning will been used extensively in other classification domains with high-dimensional data, such as macroscopic ecology, microarray analysis, and text classification.

The goal of feature selection will be to find the combination of the model parameters and the feature subset that provides the lowest expected error on novel input data. Feature selection will be of utmost importance in the realm of microbiome classification due to the generally large number of features (i.e., constituent species-level taxa, or genes, or transcripts, or metabolites, or some combination of these): in addition to improving predictive accuracy, reducing the number of features leads to the production of more interpretable models. Approaches to feature selection are typically divided into three categories: filter methods, wrapper methods, and embedded methods.

As the simplest form of feature selection, filter methods are completely agnostic to the choice of learning algorithm being used; that is, they treat the classifier as a black box. Filter methods use a two-step process. First a univariate test (e.g. t-test) or multivariate test (e.g., a linear classifier built with each unique pair of features) will be performed to estimate the relevance of each feature, and (1) all features whose scores exceed a predetermined threshold will be selected or (2) the best n features for inclusion in the model will be selected; then a classifier on the reduced feature set will be run. The choice of n can be determined using a validation data set or cross-validation on the training set.

Filter methods have several benefits, including their low computational complexity, their ease of implementation, and their potential, in the case of multivariate filters, to identify important interactions between features. The fact that the filter has no knowledge about the classifier is advantageous in that it provides modularity, but it can also be disadvantageous, as there is no guarantee that the filter and the classifier will have the same optimal feature subsets. For example, a linear filter (e.g., correlation-based) is unlikely to choose an optimal feature subset for a nonlinear classifier such as an SVM or a random forest (RF).

The purpose of a filter will be to identify features that are generally predictive of the response variable, or to remove features that are noisy or uninformative. Common filters include, but are not limited to, the between-class $\chi^2$ test, information gain (decrease in entropy when the feature is removed), various standard classification performance measures such as precision, recall, and the F-measure, and the accuracy of a univariate classifier, and the bi-normal separation (BNS), which treats the univariate true positive rate and the false-positive rate (tpr, fpr, based on document presence/absence in text classification) as though they were cumulative probabilities from the standard normal cumulative distribution function, and the difference between their respective z-scores. $F^1$ (tpr)-$F^1$ (fpr), will be used as a measure of that variable's relevance to the classification task.

Wrapper methods are usually the most computationally intensive and perhaps the least elegant of the feature selection methods. A wrapper method, like a filter method, will treat the classifier as a black box, but instead of using a simple univariate or multivariate test to determine which features are important, a wrapper will use the classifier itself to evaluate subsets of features. This leads to a computationally intensive search: an ideal wrapper will retrain the classifier for all feature subsets, and will choose the one with the lowest validation error. Were this search tractable, wrappers would be superior to filters because they would be able to find the optimal combination of features and classifier parameters. The search will not be tractable for high-dimensional data sets; hence, the wrapper will use heuristics during the search to find the optimal feature subset. The use of a heuristic will limit the wrapper's ability to interact with the classifier for two reasons: the inherent lack of optimality of the search heuristic, and the compounded lack of optimality in cases where the wrapper's optimal feature set differs from that of the classifier. In many cases the main benefit of using wrappers instead of filters, namely that the wrapper can interact with the underlying classifier, is shared by embedded methods, and the additional computational cost incurred by wrappers therefore makes such methods unattractive.

Embedded approaches to feature selection will perform an integrated search over the joint space of model parameters and feature subsets so that feature selection becomes an integral part of the learning process. Embedded feature selection will have the advantage over filters that it has the opportunity to search for the globally optimal parameter-feature combination. This is because feature selection will be performed with knowledge of the parameter selection process, whereas filter and wrapper methods treat the classifier as a "black box." As discussed above, performing the search over the whole joint parameter-feature space is generally intractable, but embedded methods will use knowledge of the classifier structure to inform the search process, while in the other methods the classifier must be built from scratch for every feature set.

Exploration and Production of Hydrocarbons

Microbial communities as physiochemical sensors that can measure important production parameters that inform, and can direct at least in part, decision making during hydrocarbon exploration and production in a manner that can have one or more of the following improvements relative to existing approaches: (a) be non-invasive or non-disruptive to production operations, (b) capture subsurface information at a distance away from the well bore, (c) be measured in the production environment without requiring well bore workover, (d) be more cost effective than existing measurement approaches, (e) provide more accurate information about downhole conditions (g) capture subsurface information at the well bore and (f) any combination or variation of the above. The following examples illustrate some potential embodiemts of microbial communities as physiochemical sensors.

Example 10

Identifying producing hydrocarbon wells for stimulation and re-stimulation using techniques including hydraulic fracturing is a critical decision facing operators. Currently, many technical variables are used to determine this decision such as: Young's Modulus, Vitrinite reflectance, total organic content, original hydrocarbon in place, net thickness, average depth, and areal extent. All of the aforementioned variables can be gathered using current techniques and could be considered as operational information or industrial setting information. Young's modulus determines the stress and strain factors of the subsurface and can be used to determine rock brittleness and the effectiveness of the formation to fracture under hydraulic load. Vitrinite reflectance is measured to assess the thermal maturity of the reservoir. Total organic content measures the potential organic material in the subsurface. Original hydrocarbon in place is used to determine the overall potential of hydrocarbon beneath the subsurface. Net thickness determines the thickness of the formation, which contain hydrocarbon. Average depth provides details in the z-axis of a map and areal extent provides details in the x-y dimensions of a map that indicate the location of hydrocarbon.

Similarly to Example 16 and 17 samples extracted from the well cuttings, drilling mud, circulating mud, core samples, flowback, or produced fluids (including but not limited to, hydrocarbons) during the drilling or production of a subsurface reservoir, will be collected and analyzed. With these samples, key microbial features will be determined for each well and, utilizing prior database information and modeling, used to create predictive data for candidates for well stimulation and re-stimulation. This predictive or derived data will be used in conjunction with real time and historical data to develop analysis that drives production methods and decisions.

Example 11

Conducting the economic evaluation of new or existing oil leases is a critical component of hydrocarbon production. Currently, many technical variables are used to determine this decision such as: Young's Modulus, Vitrinite reflectance, total organic content, original hydrocarbon in place, net thickness, average depth, and areal extent. All of the aforementioned variables can be gathered using current techniques and could be considered historical or real time operational or industrial setting information or data. Young's modulus determines the stress and strain factors of the subsurface and can be used to determine rock brittleness and the effectiveness of the formation to fracture under hydraulic load. Vitrinite reflectance is measured to assess the thermal maturity of the reservoir. Total organic content measures the potential organic material in the subsurface. Original hydrocarbon in place is used to determine the overall potential of hydrocarbon beneath the subsurface. Net thickness determines the thickness of the formation which contain hydrocarbon. Average depth provides details in the z-axis of a map and areal extent provides details in the x-y dimensions of a map that indicate the location of hydrocarbon.

Similarly to Example 16 and Example 17, samples extracted from well cuttings, drilling mod, circulating mud, core samples, flowback, or produced fluids (including but not limited to, hydrocarbons) during the drilling or production of a subsurface reservoir will be collected and analyzed. With these samples, key microbial features will be determined for each well and, utilizing prior database information and modeling, used to assess the economic viability and potential of new or existing properties and leases for hydrocarbon production. This predictive or derived data will be used in conjunction with real time and historical data to develop analysis that drive exploration and production methods and decisions.

Example 12

Subsurface flow communication and reservoir connectivity are typically parameters that can be important or beneficial to understand when determining the value and method of production of a well in a shale formation. Subsurface flow is the flow of oil beneath the earth's surface. Connectivity represents one of the fundamental properties of a reservoir that directly affects recovery. If a portion of the reservoir is not connected to a well, it cannot be drained. Connectivity parameters may be defined as the percentage of the reservoir that is connected, and reservoir connectivity is defined as the percentage of the reservoir that is connected to wells and/or fractures stimulated within a well. Currently, many technical variables are used to make this assessment such as: Geochemical analysis, tracer analysis, and microseismic analysis. All of the aforementioned variables can be gathered using current techniques and could be considered historical or real time data. Geochemical analysis is the chemical analysis of the carbon, salt or other chemical constituents of the hydrocarbon, water, or gas content in the subsurface and used to identify the unique characteristics of the fluids in question. Tracer analysis is the use of proprietary chemicals, radioactive or otherwise, that are injected into the subsurface and used to measure flow or other dynamic properties in the subsurface. Microseismic analysis is the use of seismic data to characterize the geophysical and seismic properties of the rock formation during drilling, hydraulic fracturing, or production.

Similarly to Example 16 and Example 17, samples extracted from well cuttings, circulating mud, core samples, flowback, or produced fluids (including but not limited to, hydrocarbons) during the drilling or production of a subsurface reservoir can be collected and analyzed. With these samples, key microbial features will be determined for each well and, utilizing prior database information and modeling, used to create predictive data for the well's subsurface flow communication and reservoir connectivity. This predictive or derived data will be used in conjunction with real time and historical data to develop analysis that drives production methods and decisions.

Example 13

Determining the optimal locations for drilling new wells on existing leases is a critical decision facing operators. This decision is known by many industrial terms such as downspacing strategy, infill drilling, or infield drilling. All these terms refer to the same general need, to maximize the effectiveness of future drilling on an existing lease. Currently, many technical variables are used to make this assessment such as: reservoir connectivity, geochemical analysis, tracer analysis, and microseismic analysis. All of the aforementioned variables can be gathered using current techniques and could be considered historical or real time operational or industrial setting information or data. Geochemical analysis is the chemical analysis of the carbon, salt or other chemical constituents of the hydrocarbon, water, or gas content in the subsurface and used to identify the unique characteristics of the fluids in question. Tracer analysis is the use of proprietary chemicals, radioactive or otherwise, that are injected into the subsurface and used to measure flow or other dynamic properties in the subsurface. Microseismic analysis is the use of seismic data to characterize the geophysical and seismic properties of the rock formation during drilling, hydraulic fracturing, or production. Connectivity parameters may be defined as the percentage of the reservoir that is connected, and reservoir connectivity is defined as the percentage of the reservoir that is connected to wells and/or fractures stimulated within a well Similarly to Example 16 and Example 17, samples extracted from well cuttings, circulating mud, core samples, flowback, or produced fluids (including but not limited to, hydrocarbons) during the drilling or production of a subsurface reservoir will be collected and analyzed. With these samples, key microbial features will be determined for each well and, utilizing prior database information and modeling, used to create predictive data to develop an optimal drilling plan for future wells on an existing lease. This predictive or derived data will be used in conjunction with real time and historical data to develop analysis that drives production methods and decisions.

Example 14

Determining the percent of oil contributed from each zone or compartment in a formation is a critical analysis method for operators. Understanding of these contribution profiles drives decisions on how to maximize production from each zone and the ultimate economic potential of the well. This analysis is particularly challenging in co-mingled production streams. Co-mingled production streams refer to the production of hydrocarbon from multiple locations, zones, intervals in the vertical or horizontal dimension of the subsurface. Currently, many technical variables are used to assess oil contribution for each zone such as: geochemical analysis, and tracer analysis. All of the aforementioned variables can be gathered using current techniques and could be considered historical or real time data. Geochemical analysis is the chemical analysis of the carbon, salt or other chemical constituents of the hydrocarbon, water, or gas content in the subsurface and used to identify the unique characteristics of the fluids in question. Tracer analysis is the use of proprietary chemicals, radioactive or otherwise, that are injected into the subsurface and used to measure flow or other dynamic properties in the subsurface.

Similarly to Example 16 and Example 17, samples extracted from well cuttings, circulating mud, core samples, flowback, or produced fluids (including but not limited to, hydrocarbons) during the drilling or production of a subsurface reservoir will be collected and analyzed. With these samples, key microbial features will be determined for each well and, utilizing prior database information and modeling, used to create predictive data to assess the percentage of contribution from each interval, location, or zone of the subsurface. This predictive or derived data will be used in conjunction with real time and historical data to develop analysis that drives production methods and decisions.

Example 15

Determining the optimal locations to hydraulically fracture a newly drilled well is a critical economic decision of operators. Each stage of a fracture is economically costly and carry environmental risks so operators want to identify those stages which are most effective to stimulate. Currently, many techniques are used to assess the characteristics of the well bore such as: wireline well logs and logging while drilling (LWD). All of the aforementioned techniques can be gathered using current techniques and could be considered historical or real time data. Wireline well logs refers to the use of measurement devices along the wellbore that characterize the physical and chemical properties of the wellbore, rock formation, and potential for hydrocarbon production. LWD refers to the use of measurement devices during the drilling process that characterize the physical and chemical properties of the wellbore, rock formation, and potential for hydrocarbon production.

Similarly to Example 16 and Example 17, samples extracted from well cuttings, circulating mud, core samples, flowback, or produced fluids (including but not limited to, hydrocarbons) during the drilling or production of a subsurface reservoir will be collected and analyzed. With these samples, key microbial features will be determined for each wellbore and, utilizing prior database information and modeling, used to determine the optimal locations for hydraulic fracturing. This predictive or derived data will be used in conjunction with real time and historical data to develop analysis that drives production methods and decisions.

Example 16

In this example, two indices will be used to compare community-level bacterial richness across 95 different oil samples. First the number of observed OTUs will be computed, based on OTUs clustered with an open reference OTU picking protocol at the 97% sequence similarity level. This index of diversity is limited in that it characterizes diversity at only a single level of taxonomic resolution. Diversity will also be computed using an index such as Faith's index of phylogenetic diversity (Faith's PD), which provides an integrated index of the phylogenetic breadth contained within each community.

In both cases, the diversity metrics will be calculated for a randomly selected subset of the same number of sequences (which is could be based on rarefaction curves generated from the samples) per oil sample, 1000 sequences per sample, for instance, because species richness is unavoidably correlated with the number of sequences collected. By using a set number of sequences, general diversity patterns will be compared even if it is highly unlikely that the full extent of diversity was surveyed in each community.

Different metadata factors (hydrocarbon concentration and formation depth, for example) and their effects on microbial community composition will be determined using the UniFrac results. As previously discussed, UniFrac quantifies the fraction of unique branch lengths against the total branch length between pairs of communities from one phylogenetic tree, giving an estimate of the phylogenetic distance between those communities. Separate neighbor-joining phylogenetic trees containing all of the bacterial will be generated with FastTree. Phylogenetic distances between the bacterial communities for each plot will be generated using weighted and unweighted UniFrac. Dendograms are among the available methods of viewing a tree.

If the composition of bacterial communities in this example were highly variable across formation depth, they may share only a small percentage of phylotypes (ie 0.9% at the 97% similarity level), although this degree of community overlap is likely to be an underestimate given that not all phylotypes present in a given sample were identified. Visualization of the pairwise UniFrac distances on PCoA plots would indicate significant variability within and across the depth of the formation. Samples from the deepest formations, for example, may harbor similar microbial communities. However, microbial communities from more shallow formations yet at similar depths may not necessarily harbor similar bacterial communities, as the variability between depths could exceeded the variability within a given range of depth. This pattern would be confirmed by a nonsignificant ANOSIM P value (P>0.05) for depth effects on UniFrac distances. If the hydrocarbon concentration were most strongly correlated with the overall UniFrac distances between samples, the PCoA plots would show minimal overlap among communities that differ by more than few percent in hydrocarbon concentration when samples are colored by hydrocarbon content. This effect would be clearly visible on a PCoA plot where the points are colored by hydrocarbon concentration. These plots are easily generated using EMPeror, an open source software package developed for the visualization of PCoA plots in the context of sample metadata, or another software which supports exploratory data analysis such as this.

Figure 12:
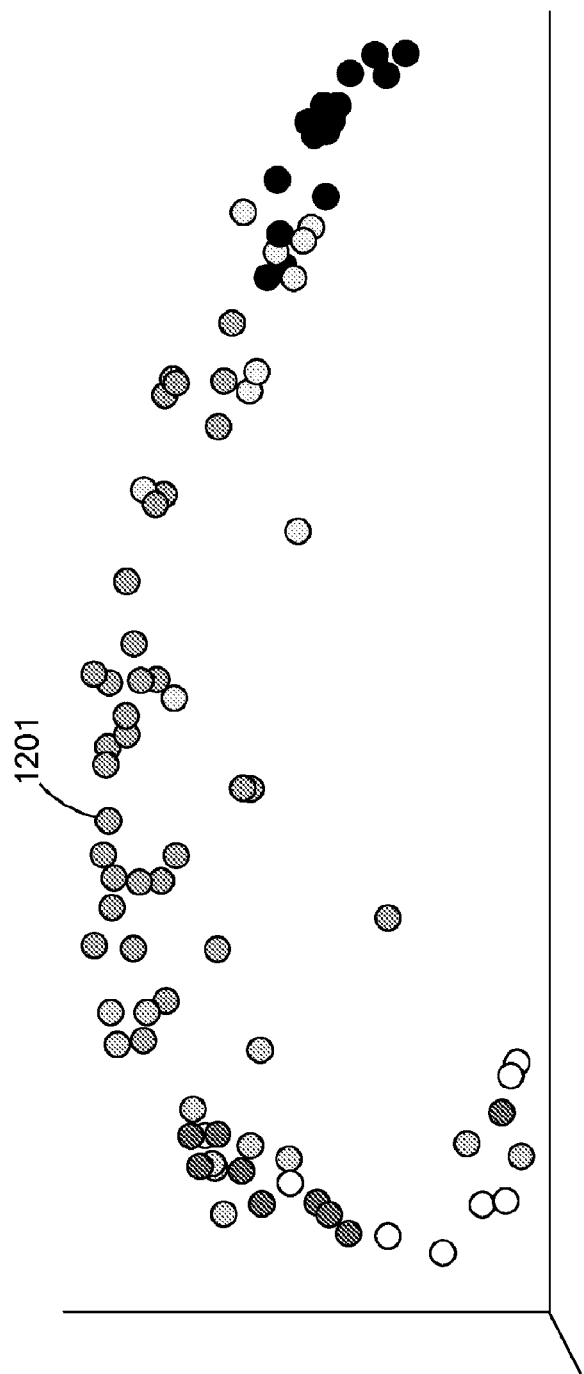
FIG. 12 is an embodiment of a Principal Coordinates (PCoA) plot in accordance with the present inventions.

FIG. 12 is an embodiment of a Principal Coordinates (PCoA) plot. Each point, e.g., 1201, in this PCoA plot represented one of 88 soil samples included in a global survey of soil microbial diversity. Points that are closer in space are more similar in phylogenetic composition. Points are shown in varying color (grey scale for purposes of patent figure) based upon sample pH. It is clear that samples which are more similar in microbial composition (i.e., closer in space in the PCoA plot) are similar in pH. This illustrates one strategy that can be employed to associate overall phylogenetic composition with environmental information to identify parameters associated with, driving, or driven by microbial composition. This plot was generated using Emperor, an open source software package developed for the visualization of PCoA plots in the context of sample metadata, which supports exploratory data analysis such as this.

Figure 13:
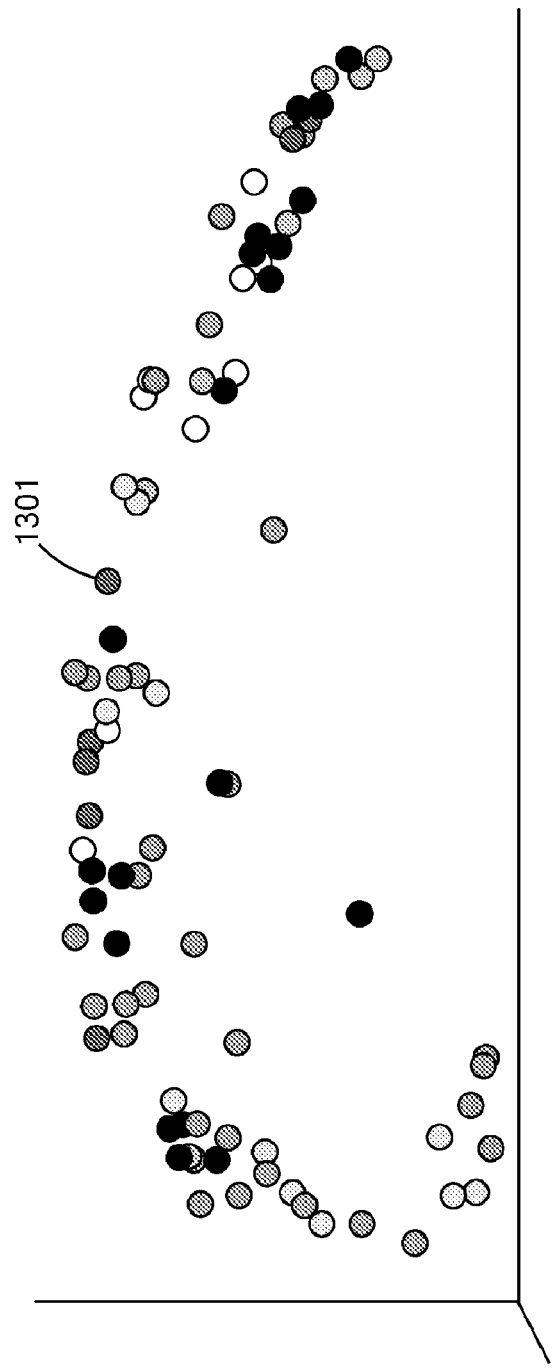
FIG. 13 is an embodiment of a Principal Coordinates (PCoA) plot in accordance with the present inventions.

FIG. 13 is an embodiment of a PCoA plot. Each point, e.g., 1301 in this PCoA plot represented one of 88 soil samples included in a global survey of soil microbial diversity. Points that are closer in space are more similar in phylogenetic composition. This is the same plot presented in FIG. 10 except that points are now colored (grey scale for purposes of patent figure) by the latitude at which the sample was collected, rather than pH. It is clear that samples which are more similar in microbial composition (i.e., closer in space in the PCoA plot) are not necessarily similar in latitude. When compared to FIG. 10, it is clear that pH is far more strongly associated with microbial composition than is latitude.

Custom analyses with UniFrac will be done as well. The UniFrac and diversity metrics will be applied to specific lineages of bacteria (Actinobacteria, Alphaproteobacteria, Garrimaproteobacteria, and Firmicutes, for example). These lineage-specific analyses will be distinct from those described previously in that the diversity and phylogenetic composition of these individual taxa across the collected oil samples will be compared, not just the overall patterns evident from examining all taxa together. The taxa selected should be the most abundant groups of bacteria in the total sequence dataset, often referred to as phyla, recognizing that the term "phyla" is being used in a general manner.

For the lineage-specific UniFrac analyses, the number of sequences will be determined by randomly selecting sequences per sample depending on the abundance of a given phyla in a given sample. Normalizing the number of sequences per sample allows for control for the effects of survey effort (number of sequences per phylum per sample) in comparing the lineage-specific UniFrac distances across the sample set. Because some samples will not have the required number of sequences per phylum, these lineage-specific analyses will be conducted on only a subset of the total samples, excluding those samples where the individual phyla were relatively rare. From the lineage analysis, some taxa may change in a consistent way from low to high hydrocarbon content, and these consistent changes can drive the patterns observed in PCoA plots.

The phylogenetic approaches of UniFrac distances and Faith's PD are more powerful than standard OTU-based approaches where community structure and diversity are compared at a single level of sequence similarity because they take into account different levels of similarity between different pairs of taxa. In particular, comparing communities by grouping sequences into OTUs defined at the 97% similarity level has limitations in that such surveys will be far from comprehensive, and overarching patterns evident by comparing overall phylogenetic structure may be more difficult to discern and quantify.

Example 17

In the oil well setting, detailed metadata for each sample will be collected and compiled in a spreadsheet, database, or other system for organizing tabular or otherwise structured information. Text mining or other techniques may also be used to convert unstructured information into structured information for analysis, or the unstructured data may be analyzed directly. This metadata includes information about sample collection, the well and formation, chemical and physical characteristics of the fluid, and well productivity. Other associated metadata can be gathered from well logs, production, seismic, cores, etc. For each sample, general metadata requirements will include, but is not limited to: source well identifier; source formation identifier(s); collection source (wellhead or tank); collection date and time; collector name or identifier (to test for collector-specific patterns, which may indicate contamination); and method of collection (if more than one is used). For each well, general metadata requirements will include, but are not limited to: well history; previous experiments at that particular well; previous well identifiers that were affected by certain experiments; maps; time in operation; physical characteristics of fluid, including pressure, temperature, and/or viscosity of the reservoir away from the wellbore and injection locations; chemical characteristics of fluid, including the concentrations and distributions of specific hydrocarbons, and other parameters previously collected; geological characteristics, including permeability, porosity, location of oil/water interface; production data, including volume of different hydrocarbons over time, rate of decline, different recovery operations (primary, secondary, tertiary recovery, etc.); indication of "strange" wells, or those that had surprising or unpredictable performance (for example, which wells stopped producing rapidly, did not meet productivity expectations, had unusual chemistries, physics, oil/water changes, etc.). Determining the microbial communities will be helpful for an assortment of goals, for example, if the microbial profile varies as a function of pressure, temperature, and/or viscosity then it can be an indicator for reservoir rock/fluid conditions. Knowledge of these parameters can change the flow rates and pressure used in a flooding operation.

Example 18

An embodiment of an on-site sequencing has a specialized set of equipment and reagents including but not limited to: sample collection containers, personal protective equipment, pipettors, plastic consumables (eg pipet tips, conical centrifuge tubes of various volumes), electrophoresis equipment, fluorometric measuring devices (single tube and plate readers), centrifuges, PCR hoods, thermocylers, ice machine or peltier cooling unit and water bath or peltier heating unit for 96 well plates, DNA/RNA extraction reagents, quanitification reagents for genetic material, liquid-handling robot, sequencer (Illumina MiSeq, for instance), compute resources, high speed data transmission capabilities (land line or satellite based). These items could be housed in a 1) a mobile vehicle capable of accessing any site on which oil and gas exploration or production is being carried out or 2) a standard 20 ft intermodal shipping container that can be placed on-site and leveled or 3) a trailer that can be towed onto a worksite and leveled. In any instance the mobile unit should be modified to support sample collection, DNA extraction, PCR and quantification of PCR product, and sequencing in an environment suitable for work in microbiology or molecular biology. Modifications of primary concern are consistent electrical supply to run the equipment; use of non-porous material and/or standard laboratory bench material for floors, sides and ceilings that can be cleaned and decontaminated with for example DNAse AWAY or bleach solution; have positive pressure with HEPA filtered air flow to minimize the chance of dust and or contaminants and volatiles entering the lab work area and/or a cabinet with such filtering; an anteroom where trained personnel can removed soiled garments and change into appropriate laboratory clothing.

Example 19

The microbiome of an oil patch is distinctive and that microbiome can be analyzed to predict where other oil patches may exist. To develop useful microbial sensors based on oil extracted from wells, essential baseline information about compositional differences of fluids across space and time must be collected. This is necessary to inform future studies of microbial communities at this site. For example, the studies will provide information about the intra-well temporal dynamics of microbial communities, and how those compositional differences relate to the inter-well and inter-formation differences and the associated characteristics, including productivity, of each well. The production zone that oil was extracted from when it reaches a wellbore will include production-zone-specific microbial indicators that, from an oil sample, could be used to indicate the source production zone. Microbial indicators of pressure, temperature, and/or viscosity that, from an oil sample, will be used to determine the pressure, temperature, and/or viscosity of the reservoir away from the wellbore and injection locations.

The predictive power of the microbiome analysis will be used to predict discrete variables and continuous variables. In another example, the microbiome indicators will provide information on primary production, when the location of the water/oil interface changes, so that the concentration of oil in the extract decreases. Microbial indicators of the location of or distance from the oil/water interface will indicate that the interface has shifted, or that the well is tapped. In another example, microbiome exploratory analysis will be used to determine what fluid/well parameters or production characteristics may be correlated with our microbial indicators. The low specificity, high sensitivity sweep for microbial indicators that are economically useful will provide preliminary data that can be used to perform more robust investigation in future sampling events.

Microbial Measurements as Physiochemical Sensors in a Hydrocarbon Production Setting Microbial communities as physiochemical sensors that can measure important production parameters that inform, and can direct at least in part, decision making during hydrocarbon exploration and production in a manner that can have one or more of the following improvements relative to existing approaches: (a) be non-invasive or non-disruptive to production operations, (b) capture subsurface information at a distance away from the well bore, (c) be measured in the production environment without requiring well bore workover, (d) be more cost effective than existing measurement approaches, or (e) provide more accurate information about downhole conditions and (f) any combination or variation of the above. The following examples illustrate some potential uses of microbial communities as physiochemical sensors.

Example 20

Oil saturation and permeability are typically useful parameters to determine both well zones that could be attractive candidates for hydraulic fracturing and the potentially more effective methods for hydraulic fracturing. These parameters are also applicable in oil production techniques, such as waterflood operations, that do not involve or require hydraulic fracturing but require detailed knowledge of the subsurface to inform production decisions (e.g. off shore oil production or on shore production). Oil saturation is the fraction of the pore space occupied by oil. Most oil reservoirs also contain some connate water (non-movable). The oil saturation directly affects the calculation of reserves. Oil permeability is the property of rocks that is an indication of the ability for oil to flow through rocks. High permeability will allow oil and gases to move rapidly through the rocks.

Similarly to Example 16 and Example 17, samples extracted from the circulating mud, core samples, flowback, and/or produced fluids (including but not limited to, hydrocarbons) during the drilling or production of a subsurface reservoir, will be collected and analyzed. With these samples, key microbial features will be determined for each well zone and, utilizing prior database information and modeling, used to create predictive data for oil saturation and permeability. This predictive or derived data will be used to drive production methods and decisions.

Example 21

A reservoirs' wettability is typically a useful parameter in determining the permeability, production potential, and most effective method of hydraulically fracturing a well. Wettability is the preference of a solid to contact one liquid or gas, known as the wetting phase, rather than another. The wetting phase will tend to spread on the solid surface and a porous solid will tend to imbibe the wetting phase, in both cases displacing the nonwetting phase. Rocks can be water-wet, oil-wet or intermediate-wet. The intermediate state between water-wet and oil-wet can be caused by a mixed-wet system, in which some surfaces or grains are water-wet and others are oil-wet, or a neutral-wet system, in which the surfaces are not strongly wet by either water or oil. Wettability affects relative permeability, electrical properties, nuclear magnetic resonance relaxation times and saturation profiles in the reservoir. The wetting state impacts waterflooding and aquifer encroachment into a reservoir. Surfactants or other additives in drilling fluids, especially oil-base mud, or other injected fluids can change formation wettability. Wettability change is normally treated with mutual solvents to remove the rock-oil coating (asphaltene or paraffin precipitation), followed by a strong water-wet surfactant to reduce the tendency of further hydrocarbon precipitation.

Similarly to Example 16 and Example 17, samples extracted from the circulating mud, core samples, flowback, and/or produced fluids (including but not limited to, hydrocarbons) during the drilling or production of a subsurface reservoir will be collected and analyzed. With these samples, key microbial features will be determined for a subsurface reservoir and, utilizing prior database information and modeling, used to create predictive data for the well's wettability. This predictive or derived data will be used to drive production methods and decisions.

Example 22

Oil viscosity, temperature, pressure, porosity, oil or water saturation, and compressibility are typically useful parameters for determining the value and method of production of a well. Oil viscosity is a frictional measurement of oil flow at a given temperature and determines its resistance to flow. Water content is expressed as a ratio, which can range from 0 (completely dry) to the value of the materials' porosity at saturation. Porosity, or void fraction, is a measure of the void (i.e., "empty") spaces in a material, and is a fraction of the volume of voids over the total volume, between 0 and 1, or as a percentage between 0 and 100%. The oil or water content at saturation is the maximum content able to be held in the subsurface at equilibrium conditions.

Compressibility is the relative change in fluid volume related to a unit change in pressure. This is usually expressed as volume change per unit volume of fluid per psi of pressure change. Gas has higher compressibility than liquid (oil or water).

Similarly to Example 16 and Example 17, samples extracted from the circulating mud, core samples, flowback, and/or produced fluids (including but not limited to, hydrocarbons) during the drilling or production of a subsurface reservoir will be collected and analyzed. With these samples, key microbial features will be determined for each well zone and, utilizing prior database information and modeling, used to create predictive data for the well's oil viscosity, temperature, pressure, porosity, oil or water saturation, and compressibility. This predictive or derived data will be used to drive production methods and decisions.

Example 23

Subsurface flow communication and reservoir connectivity are typically parameters that can be important or beneficial to understand when determining the value and method of production of a well. Subsurface flow is the flow of oil beneath the earth's surface. Connectivity represents one of the fundamental properties of a reservoir that directly affects recovery. If a portion of the reservoir is not connected to a well, it cannot be drained. Connectivity parameters may be defined as the percentage of the reservoir that is connected, and reservoir connectivity is defined as the percentage of the reservoir that is connected to wells.

Similarly to Example 16 and Example 17, samples extracted from the circulating mud, core samples flowback, and/or produced fluids (including but not limited to, hydrocarbons) during the drilling or production of a subsurface reservoir be collected and analyzed. With these samples, key microbial features will be determined for each well zone and, utilizing prior database information and modeling, used to create predictive data for the well's subsurface flow communication and reservoir connectivity. This predictive or derived data will be used to drive production methods and decisions.

Microbial Measurements as Tracers in an Oil and Gas Field

Microbial communities acting as tracers in the oil & gas fields can have one or more of the following improvements relative to existing approaches: (a) be environmentally benign, (b) be custom and specific to the oil reservoir, (c) be more cost effective. (d) provide greater resolution, and (e) any combination or variation of the above.

Example 24

A well's propensity for producing oil versus gas typically can be a central parameter when determining the value and method of production of a well. Both the type of hydrocarbon and total productivity can be critical determinants in a well's potential and the timing to produce from the well given economic and technical conditions.

Similarly to Example 16 and Example 17, samples extracted from the circulating mud, core samples, flowback, and/or produced fluids (including but not limited to, hydrocarbons) during the drilling or production of a subsurface reservoir will be collected and analyzed. With these samples, key microbial features will be determined for each well zone and, utilizing prior database information and modeling, used to create predictive data for the well's propensity for producing oil versus gas. This predictive or derived data will be used to drive production methods and decisions.

Example 25

The bacteria that are present in a well can be a key factor when determining the value and method of production of a well. Bacteria can have negative influence on the production of oil and gas. To mitigate their effects, biocides can be included in hydraulic fracturing solutions. Biocides are commonly used in water muds containing natural starches and gums that are especially vulnerable to bacterial attack. Biocide choices are limited, and care must be taken to find those that are effective yet approved by governments and by company policy. Biocides can be used to control sulfate-reducing bacteria, slime-forming bacteria, iron-oxidizing bacteria and bacteria that attacks polymers in fracture and secondary recovery fluids. In polymers, the degradation of the fluid is controlled, thus avoiding the formation of a large biomass, which could plug the formation and reduce permeability.

Similarly to Example 16 and Example 17, samples extracted from the circulating mud, core samples flowback, and/or produced fluids (including but not limited to, hydrocarbons) during the drilling or production of a subsurface reservoir will be collected and analyzed. With these samples, key microbial features will be determined for each well zone and, utilizing prior database information and modeling, used to create predictive data for the bacteria present in a well. This predictive or derived data will allow for the more selective use of biocides, thereby reducing or changing overall biocide usage while increasing production potential.

Example 26

The oil reservoir or zone that a specific well has tapped is typically useful information when determining the value and method of production of a well. Knowledge of which zone is producing and the quantity of oil remaining in the zone inform waterflood operations. The waterflood operations seek to improve the conformance of oil production along the vertical well bore (vertical conformance) as well as ensuring consistent production across the breadth wells at the surface (aerial conformance). A well zone is a slab of reservoir rock bounded above and below by impermeable rock. A production zone's size, permeability, saturation, and propensity to produce oil as well as vertical and aerial conformance are all factors that determine the optimal number of well's that can be used to produce oil from the reservoir and the methods to waterflood or CO2 flood the reservoir to increase production.

Similarly to Example 16 and Example 17, samples extracted from the circulating mud, core samples flowback, and/or produced fluids (including but not limited to, hydrocarbons) during the drilling or production of each zone will be collected and analyzed. With these samples, key microbial features will be determined for each well zone and, utilizing prior database information and modeling, used to create predictive data about the production zone that improves vertical and aerial conformance. This predictive or derived data will be used to drive production methods and decisions.

Example 27

Tracking treatment fluids and produced water is typically useful information in facilitating production decisions, cleanup, and environmental remediation operations. Treatment fluid is a fluid designed and prepared to resolve a specific wellbore or reservoir condition. Treatment fluids are typically prepared at the well site for a wide range of purposes, such as stimulation, isolation or control of reservoir gas or water. Every treatment fluid is intended for specific conditions and should be prepared and used as directed to ensure reliable and predictable performance. Produced water is water produced from a wellbore that is not a treatment fluid. The characteristics of produced water vary and use of the term often implies an inexact or unknown composition. It is generally accepted that water within the pores of shale reservoirs is not produced due to its low relative permeability and its mobility being lower than that of gas.

Similarly to Example 16 and Example 17, samples extracted from the circulating fraced water produced water, and/or other fluids during drilling or production will be collected and analyzed. With these samples, key microbial features will be determined for the subsurface reservoir and, utilizing prior database information and modeling, used to create predictive data about the chemical and physical properties of the treatment and produced fluids. This predictive or derived data will be used to drive production decisions, cleanup, and environmental remediation operations. Likewise, such data could be used to make decisions about cleanup, and environmental remediation operations Example 28

Determining pay zones can be a key factor when determining the value and method of production of a well. The overall interval in which pay sections occur is the gross pay; the smaller portions of the gross pay that meet local criteria for pay (such as minimum porosity, permeability and hydrocarbon saturation) are net pay. Understanding the state of local criteria can determine if it is economically advantageous to hydraulically re-fracture a site to increase or prolong oil production.

Similarly to Example 16 and Example 17, samples extracted from the circulating mud, core samples, flowback, and/or produced fluids (including but not limited to, hydrocarbons) will be collected and analyzed. With these samples, key microbial features will be determined the subsurface reservoir and, utilizing prior database information and modeling, used to create predictive data about the pay zones that a well has tapped. This predictive or derived data will be used to drive production methods and decisions.

Example 29

The prevention of water table and groundwater aquifers contamination can be a central task in reducing the environmental impact of hydraulic fracturing. Monitoring the microbiomes of the water supplies that are local to a hydraulic fracturing site allows energy producers to assess if and how their development has altered local environments. Because microbiomes are particularly susceptible to environmental changes they well suited to act as early indicators of change.

Similarly to Example 16 and Example 17, samples extracted from the local water supplies and/or fluids contained around and from wells will be collected and analyzed. With these samples, key microbial features will be determined for the subsurface reservoir and, utilizing prior database information and modeling, used to create predictive data about the environmental impact of the hydraulic fracturing. This predictive or derived data will be used to limit the environmental impact through the optimization of production methods.

Example 30

A high-resolution subsurface geologic map of a region is typically a useful tool when determining the value and method of production of a well. Geologic maps show the type and spatial distribution of rocks. Rock formations are color-coded and symbols for geological structures are annotated, so age relationships are evident. Topographic contours can also appear on geologic maps. Detailed information about the Similarly to Example 16 and Example 17, samples extracted from the circulating mud, core samples, flowback, and/or produced fluids (including but not limited to, hydrocarbons) during the drilling or production of a subsurface reservoir will be collected and analyzed. With these samples, key microbial features will be determined for each well zone and, utilizing prior database information and modeling, used to create predictive data that can be transformed into a high resolution subsurface geologic map of a production zone. This predictive or derived data will be used to drive production methods and decisions.

Example 31

The oil-water contact point can be a key factor when determining the value and method of production of a well. The oil-water contact is a bounding surface in a reservoir above which predominantly oil occurs and below which predominantly water occurs. Although oil and water are immiscible, the contact between oil and water is commonly a transition zone and there is usually irreducible water adsorbed by the grains in the rock and immovable oil that cannot be produced. The oil-water contact is not always a flat horizontal surface, but instead might be tilted or irregular.

Similarly to Example 16 and Example 17, samples extracted from the circulating mud, core samples flowback, and/or produced fluids (including but not limited to, hydrocarbons) during the drilling of a subsurface reservoir will be collected and analyzed. With these samples, key microbial features will be determined for each well zone and, utilizing prior database information and modeling, used to create predictive data for the oil-water contact levels in a well. This predictive or derived data will be used to drive production methods and decisions, Example 32

Accurate analytics of subsurface features is typically useful information to the process of Enhanced Oil Recovery. Microbial Enhanced Oil Recovery (MEOR) is a biological based technology consisting in manipulating function or structure, or both, of microbial environments existing in oil reservoirs. The ultimate aim of MEOR is to improve the recovery of oil entrapped in porous media while increasing economic profits. MEOR is a tertiary oil extraction technology allowing the partial recovery of the commonly residual two-thirds of oil, thus increasing the life of mature oil reservoirs. The optimal application of MEOR relies on having accurate subsurface analytic details on reservoir temperature, pressure, depth, net pay, permeability, residual oil and water saturations, porosity and fluid properties such as oil API gravity and viscosity.

Similarly to Example 16 and Example 17, samples extracted from the circulating mud, core samples, flowback, and/or produced fluids (including but not limited to, hydrocarbons) during the drilling of a subsurface reservoir will be collected and analyzed. With these samples, key microbial features will be determined for each well zone and, utilizing prior database information and modeling, used to create predictive data for the novel analytic analysis of a well. This predictive or derived data will be used to drive production methods and decisions.

Example 33

Gas stations are under similar pressures to monitor and remediate any potential environmental impacts. Because microbiomes are highly sensitive to environmental conditions they can act as an early indicator of any environmental impacts.

Similarly to Example 16 and Example 17, samples extracted from soil and water near gas stations will be collected and analyzed. With these samples, key microbial features will be determined for each gas station and, utilizing prior database information and modeling, used to create predictive data on the environmental impact of each gas station. This predictive or derived data will be used to drive station procedures and environmental remediation.

Exploration and Production of Hydrocarbons Industrial Use Examples: Microbial Measurements as a Predictive Tool for Key Parameters Microbial communities acting as a predictive tool that can be used to quantify or qualify difficult or hard to predict parameters that are important to oil & gas production. These predictive tools can have one or more of the following improvements relative to existing approaches: (a) be more cost effective, (d) provide greater accuracy or predictive power, (c) allow for more data integration or analysis with existing well logging tools or seismic data, and (d) any combination or variations of the above.

Example 34

During the production of hydrocarbon, the oil/water interface in the reservoir subsurface will change over time. The production rate typically has to be optimized such that maximum hydrocarbon can be extracted from the reservoir while minimizing the likelihood of oil cusping or coning. Oil cusping or coning is a condition where the underlying water layer in a production zone enters the well bore due to an increased production rate. Oil cusping or coning can permanently damage the well bore and prevent the further extraction of hydrocarbon. Currently, predicting when oil cusping or coning occurs is very difficult. Because microbiomes have unique properties based on their surrounding environment and levels of oil and water, they can serve as an early indicator or predictor of when oil cusping or coning may occur. With this early predictor, oil coning or cusping can be prevented.

Similarly to Example 16 and Example 17, samples extracted from core samples, circulating mud, and/or produced fluids (including but not limited to, hydrocarbons) will be collected and analyzed. With these samples, key microbial features will be determined for the well and, utilizing prior database information and modeling, used to create predictive data on the likelihood of oil coning or cusping. This predictive or derived data will be used to determine the optimal rate of production from a well head, Example 35

Inter-well and intra-well informatics can be central to the evaluation of reservoir productivity and commercial valuation of new and existing oil leases. As outlined in Example 16, Example 17, microbiome samples will be collected during the extraction of oil and other fluids from new or existing wells. With these samples, key microbial features will be determined for each lease and, utilizing prior database information and modeling, used to create predictive data on the features of potential surrounding oil patches. This predictive or derived data will be used to drive the commercial valuation of new leases or the commercial valuation of existing leases.

Example 36

The oil cuts and water cuts of produced oil can be a key factor when determining the value and method of production of a well. The cut of a particular liquid is the ratio of the particular liquid produced compared to the volume of total liquids produced. Produced liquids will contain a water cut ratio ranging from 0-1. A crude oil can contain water, normally in the form of an emulsion. The emulsion should be treated inside heaters using chemicals, which will break the mixture into its individual components (water and crude oil). The processing of the water from crude oil adds time and expense to production.

Similarly to Example 16 and Example 17, samples extracted from the circulating mud, core samples, flowback and/or produced fluids (including but not limited to, hydrocarbons) during the drilling or production of a subsurface reservoir will be collected and analyzed. With these samples, key microbial features will be determined for the subsurface reservoir and, utilizing prior database information and modeling, used to create predictive data for the oil and water cuts

Example 37

The potential recovery factor of a reservoir typically can be a key factor when determining the value and method of production of a well. The recoverable amount of hydrocarbon initially in place, normally expressed as a percentage from 0-100%. The recovery factor is a function of the displacement mechanism, subsurface geology, lithology, reservoir connectivity, oil properties and several other chemical and physical properties of the reservoir. Enhanced oil recovery has emerged as a means is to increase the recovery factor. Predicting the recovery factor and the potential effect of enhanced oil recovery methods during or prior to hydraulically fracturing a well will increase the efficiency of an oil producer's operations.

Similarly to Example 16 and Example 17, samples extracted from the circulating mud, core samples, flowback and/or produced hydrocarbon during the drilling or production of a subsurface reservoir will be collected and analyzed. With these samples, key microbial features will be determined for each well and, utilizing prior database information and modeling, used to create predictive data for the recovery factor of the existing and potential future wells as well as the effectiveness of any enhanced oil recovery techniques This predictive or derived data will be used to drive production methods and decisions.

Example 38

The existence of hydrogen sulfide in a reservoir typically can be a key factor when determining the value and method of production of a well. An extraordinarily poisonous gas with a molecular formula of $H_2S$. At low concentrations, $H_2S$ has the odor of rotten eggs, but at higher, lethal concentrations, it is odorless. $H_2S$ is hazardous to workers and a few seconds of exposure at relatively low concentrations can be lethal, but exposure to lower concentrations can also be harmful. The effect of $H_2S$ depends on duration, frequency and intensity of exposure as well as the susceptibility of the individual. Hydrogen sulfide is a serious and potentially lethal hazard, so awareness, detection and monitoring of $H_2S$ is essential. Since hydrogen sulfide gas is present in some subsurface formations, drilling and other operational crews must be prepared to use detection equipment, personal protective equipment, proper training and contingency procedures in $H_2S$-prone areas. Hydrogen sulfide is produced during the decomposition of organic matter and occurs with hydrocarbons in some areas. It enters drilling mud from subsurface formations and can also be generated by sulfate-reducing bacteria resident in the subsurface. $H_2S$ can cause sulfide-stress-corrosion cracking of metals. Because it is corrosive, $H_2S$ production may require costly special production equipment such as stainless steel tubing. $H_2S$ production also reduces the value of the produced oil, as the amount of sulfur reduces the value of oil from sweet (low sulfur content) to sour (high sulfur content). Because $H_2S$ is often produced by bacteria in the reservoir, microbial analysis and predictive modeling provide a new avenue for early detection of $H_2S$ formation.

Similarly to Example 16 and Example 17, samples extracted from the circulating mud, core samples, flowback, and/or produced fluids (including but not limited to, hydrocarbons) during the drilling or production of a subsurface reservoir will be collected and analyzed. With these samples, key microbial features will be determined for each well zone and, utilizing prior database information and modeling, used to create predictive data for the existence of $H_2S$ in existing and potential future wells. This predictive or derived data will be used to drive production methods and decisions.

Example 39

The monitoring and prediction of leaky pipelines typically can be a key technique for increasing productivity and preventing environmental damage. While the detection of leaks is an important part of the oil production process, they do not prevent the formation of potentially damaging and costly leaks from initially occurring. Predicting and preventing leaks prior to their formation is a more cost effective and environmentally conscious procedure. Current technology, however, make the prediction of leaks difficult. Microbial analysis and predictive modeling provide a new avenue for monitoring and predicting the formation of costly oil pipeline leaks.

Similarly to Example 16 and Example 17, samples extracted from the oil, fluids, and/or biofilm samples from each pipeline will be collected and analyzed. With these samples, key microbial features will be determined for each pipeline and, utilizing prior database information and modeling, used to create predictive data for the existence of current or future potential leaks the oil pipelines. This predictive or derived data will be used to drive production methods and decisions.

Example 40

The monitoring and prediction of the existing oil in a reservoir typically can be a central technique for determining the value and method of production of a well. A central component to determining if a reservoir is economically feasible to develop is to determine the oil in place. The oil in place is the volume of oil in a reservoir prior to production. By combining information about the predicted oil in place with other analytics, such as the predictive recovery factor and the cost of extraction, one can determine the economic feasibility of recovering the oil.

Similarly to Example 16 and Example 17, samples extracted from the produced fluids (including but not limited to, hydrocarbons), core samples, or circulating mud from each well will be collected and analyzed. With these samples, key microbial features will be determined for each reservoir and, utilizing prior database information and modeling, used to create predictive data for the oil in place of existence or future potential reservoirs. This predictive or derived data will be used to drive production methods and decisions.

Example 41

Figure 17A:
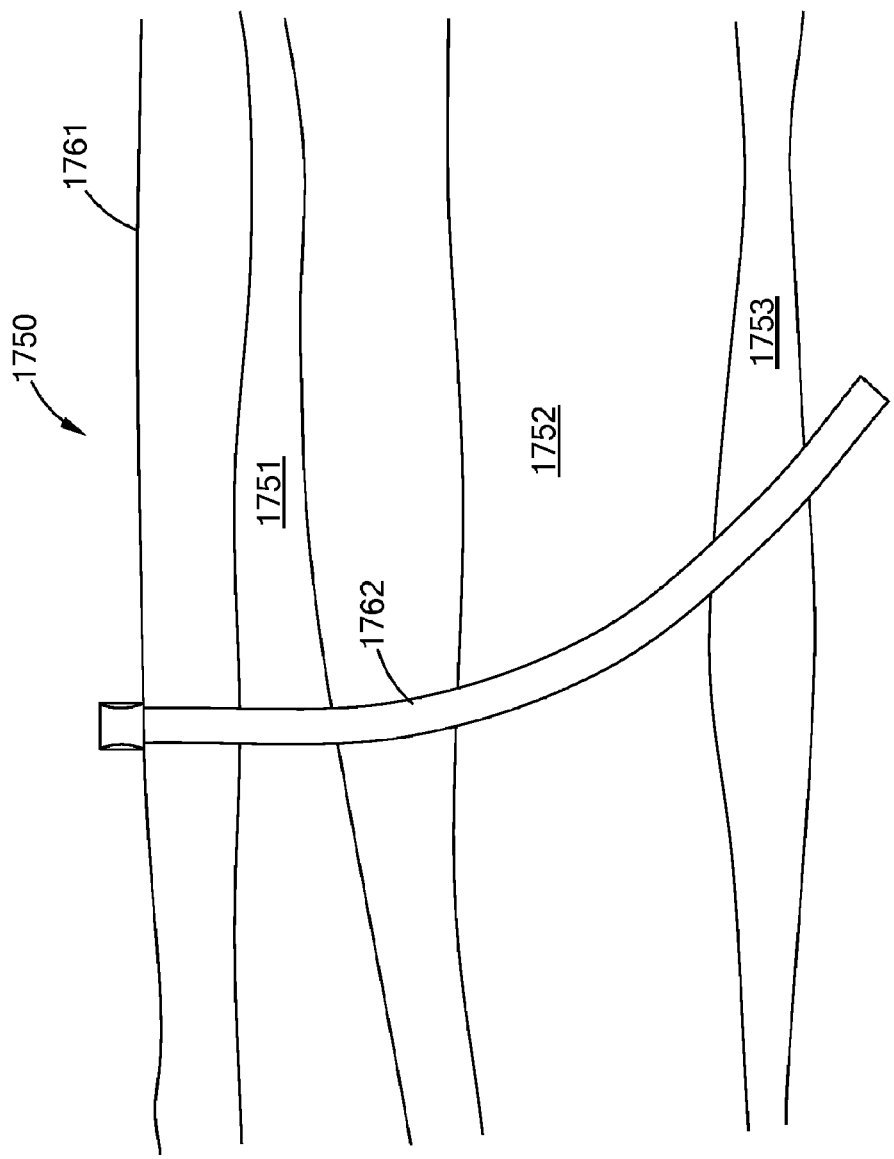
FIG. 17A is a cross sectional view of an embodiment of an oil field with a well in accordance with the present inventions.
Figure 17B:
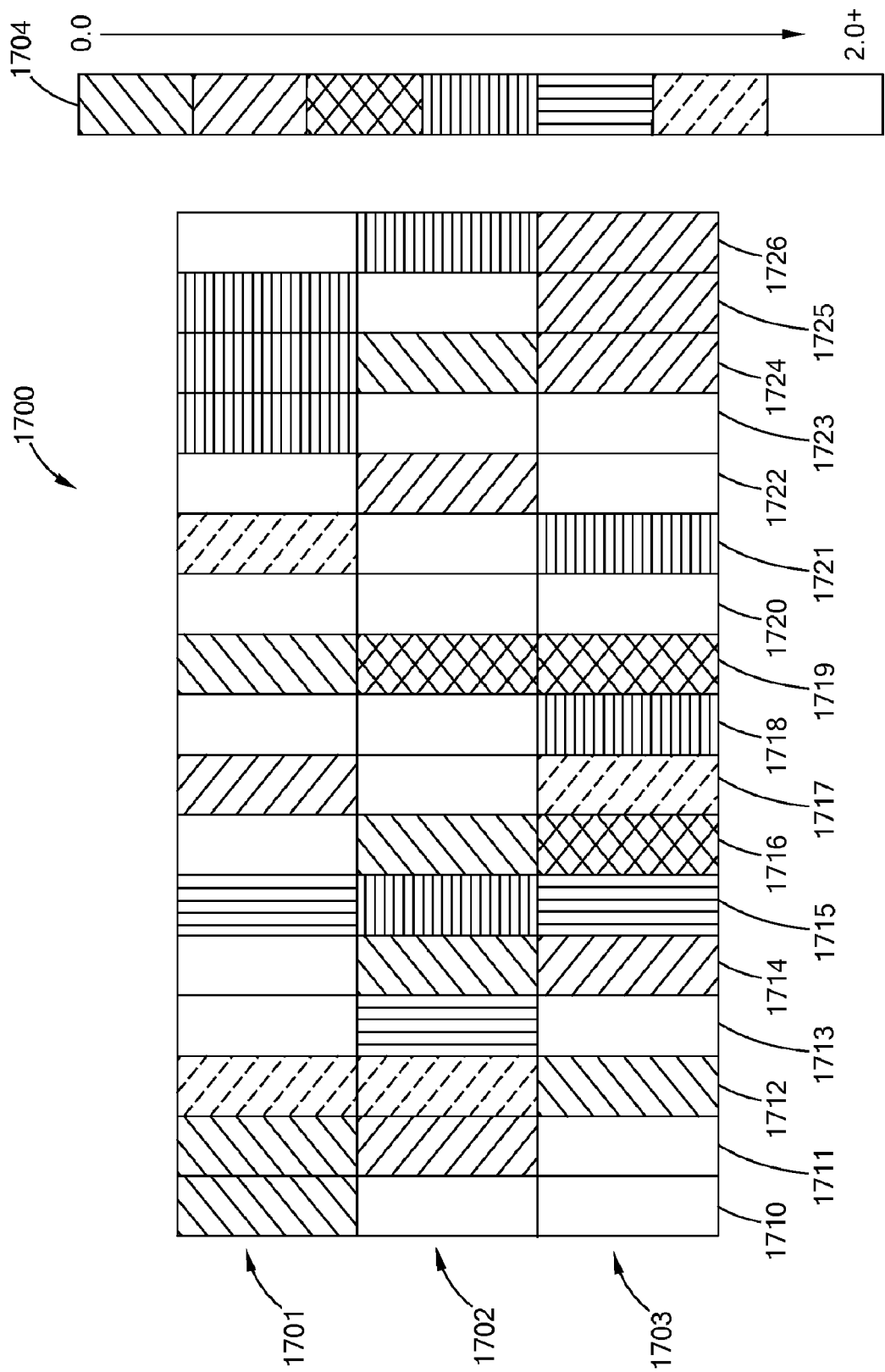
FIG. 17B is a representation of an embodiment of a finger print from the well of FIG. 17A in accordance with the present inventions.

Turning to FIG. 17A there is shown a cross sectional view of an oil field 1750, having a surface of the earth 1761 and having a borehole 1762. The borehole 1762 extends between three intervals 1751, 1752, 1753, e.g., zones, which in this embodiment correspond two three formations, e.g., a first formation 1751, and a upper second formation 1752 and a lower second formation 1753. The present evaluations are performed on fluid samples, cutting and both from the borehole 1762. These evaluations provided a figure print of well. Thus turning to FIG. 17B, there is shown a greatly simplified (for the purpose of clarity and illustration) finger print 1700 of the borehole 1762. The fingerprint 1700 has rows corresponding to the three intervals, row 1701 corresponding to interval 1751, row 1702 corresponding to interval 1752 row 1703 corresponding to interval 1753. The columns 1710, 1711, 1712, to 1726 represent different taxa. And the abundance scale 1704, is typically a log rhythmic scale with increasing amounts of taxa in the direction of the arrow. Thus, based upon the abundance and type of taxa found a fingerprint for the well, and intervals, can be determined. This fingerprint should typically be unique for every well.

It being recognized the x-axis and y-axis can be interchanged, and that these fingerprints, can be expressed in other like manner, such as pie charts, dot-matrix, bar graphs, scanner type barcodes (i.e., manufacturing or consumer product type barcoding), and other graphic, human and machine readable manners of coding or presenting information.

Figure 17C:
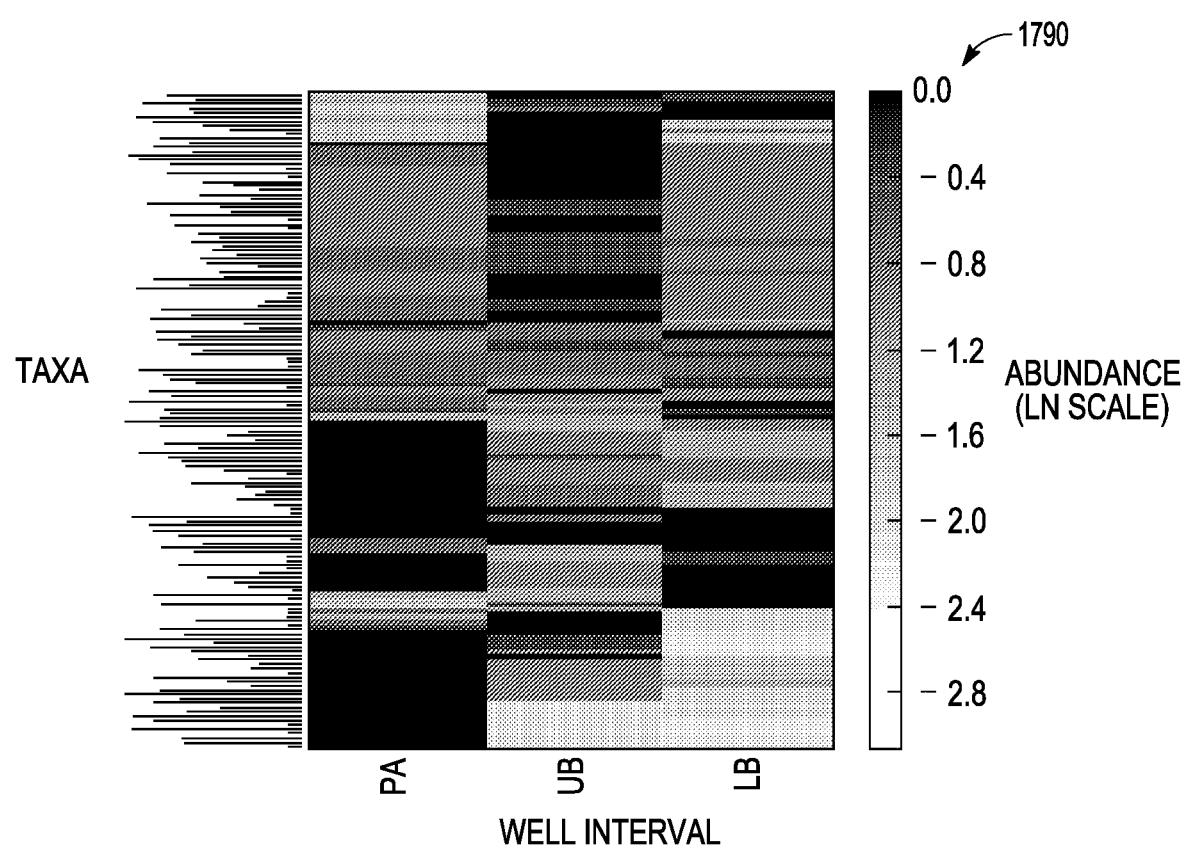
FIG. 17C is an image of a finger print for the well of FIG. 17A in accordance with the present inventions.

About 48,600,000 DNA sequences were analyzed from samples taken from material flowing from a well an oil field. In these well there are three intervals. This DNA analysis identified about 147,000 taxa present in borehole. Of these taxa about 92% had never been identified before and were not found in any known databases. This information was then evaluated by the techniques of the present inventions and identified 152 taxa of pertinence, or interest. From these 152 a fingerprint 1970 was generated, and a photograph of that fingerprint 1790 is shown in FIG. 17C.

It should be understood that the use of headings in this specification is for the purpose of clarity, and is not limiting in any way. Thus, the processes and disclosures described under a heading should be read in context with the entirely of this specification, including the various examples. The use of headings in this specification should not limit the scope of protection afford the present inventions. Thus, it should be understood that the teachings for one processes or apparatus, under one heading, and the teachings for the other processes or apparatus, under other headings, can be applicable to each other, as well as, being applicable to other sections and teachings in this specification, and vice versa.

The various embodiments of applications, methods, activities and operations set forth in this specification may be used for various other fields and for various other activities, uses and embodiments. Additionally, these embodiments, for example, may be used with: existing systems, articles, components, operations or activities; may be used with systems, articles, components, operations or activities that may be developed in the future; and with such systems, articles, components, operations or activities that may be modified, in-part, based on the teachings of this specification. Further, the various embodiments and examples set forth in this specification may be used with each other, in whole or in part, and in different and various combinations. Thus, for example, the configurations provided in the various embodiments and examples of this specification may be used with each other; and the scope of protection afforded the present inventions should not be limited to a particular embodiment, example, configuration or arrangement that is set forth in a particular embodiment, example, or in an embodiment in a particular Figure.

The inventions may be embodied in other forms than those specifically disclosed herein without departing from its spirit or essential characteristics. The described embodiments are to be considered in all respects only as illustrative and not restrictive.

What is claimed:

1. A system comprising:

a database storing extraction data corresponding to one or more sample materials obtained at a resource production field, the extraction data including microbiome data corresponding to the one or more sample materials; and a computer system including one or more memories and one or more processors, one or more computer instructions incorporated into the one or more memories to configure the one or more processors to perform operations for improving a predictive accuracy of predictive microbiome data with respect to a target environmental parameter at the resource production field, the operations comprising:

accessing the database to obtain the microbiome data;

selecting a predictive model from a plurality of predictive models based on an expected prediction error of the predictive model being lower than an expected prediction error of other models of the plurality of predictive models, the expected prediction error of the predictive model being based on repeated fittings of the predictive model to different subsets of the microbiome data or other related microbiome data;

generating the predictive microbiome data from the first subset of the microbiome data, the generating of the predictive microbiome data including applying the predictive model using a machine-learned combination of feature inputs and model parameters; and causing an interactive display of a visualization of the predictive microbiome data in a graphical user interface to assist an operator in creating a plan for directing an activity at the resource production field.

2. The system of claim 1, further comprising selecting an abundance of genetic material identified in the microbiome data as one of the feature inputs based on the machine-learned combination indicating that the abundance discriminates between classifications of data points within the microbiome data, the classifications relating to the target environmental parameter.

3. The system of claim 1, wherein the plurality of models is selected from a class of models based on structures inherent in the first subset of the microbiome data.

4. The system of claim 1, wherein a constraint inherent in the microbiome data includes a diversity of data and the class of models includes generative models appropriate for the diversity.

5. The system of claim 1, wherein the target environmental parameter relates to hydrocarbon exploration or production at the resource production field.

6. The system of claim 1, wherein the target environmental parameter relates to at least one of subsurface flow communication or reservoir connectivity.

7. The system of claim 1, wherein the target environmental parameter relates to at least one of oil saturation or permeability of a well zone.

8. The system of claim 1, wherein the target environmental parameter relates to wettability of a reservoir.

9. The system of claim 1, wherein the target environmental parameter relates to at least one of viscosity, temperature, pressure, porosity, or compressibility of oil or water in a reservoir.

10. A method comprising:
performing, using one or more processors, operations for improving a predictive accuracy of predictive microbiome data with respect to a target environmental parameter at a resource production field, the operations comprising:
accessing a database to obtain the microbiome data, the database storing extraction data corresponding to one or more sample materials obtained at the resource production field, the extraction data including the microbiome data;
selecting a predictive model from a plurality of predictive models based on an expected prediction error of the predictive model being lower than an expected prediction error of other models of the plurality of predictive models, the expected prediction error of the predictive model being based on repeated fittings of the predictive model to different subsets of the microbiome data or other related microbiome data;
generating the predictive microbiome data from the microbiome data, the generating of the predictive microbiome data including applying the predictive model using a machine-learned combination of feature inputs and model parameters; and
causing an interactive display of a visualization of the predictive microbiome data in a graphical user interface to assist an operator in creating a plan for directing an activity at the resource production field.

11. The method of claim 10, further comprising selecting an abundance of genetic material identified in the microbiome data as one of the feature inputs based on the machine-learned combination indicating that the abundance discriminates between classifications of data points within the microbiome data, the classifications relating to the target environmental parameter.

12. The system of claim 10, wherein the plurality of models is selected from a class of models based on structures inherent in the first subset of the microbiome data.

13. The system of claim 10, wherein a constraint inherent in the microbiome data includes a diversity of data and the class of models includes generative models appropriate for the diversity.

14. A non-transitory machine-readable storage medium embodying instructions that, when executed by one or more processors, cause the one or more processors to perform operations for improving a predictive accuracy of predictive microbiome data with respect to a target environmental parameter at a resource production field, the operations comprising:
accessing a database to obtain the microbiome data, the database storing extraction data corresponding to one or more sample materials obtained at the resource production field, the extraction data including the microbiome data;
selecting a predictive model from a plurality of predictive models based on an expected prediction error of the predictive model being lower than an expected prediction error of other models of the plurality of predictive models, the expected prediction error of the predictive model being based on repeated fittings of the predictive model to different subsets of the microbiome data or other related microbiome data;
generating the predictive microbiome data from the microbiome data, the generating of the predictive microbiome data including applying the predictive model using a machine-learned combination of feature inputs and model parameters; and
causing an interactive display of a visualization of the predictive microbiome data in a graphical user interface to assist an operator in creating a plan for directing an activity at the resource production field.

15. The non-transitory machine-readable storage medium of claim 14, further comprising selecting an abundance of genetic material identified in the microbiome data as one of the feature inputs based on the machine-learned combination indicating that the abundance discriminates between classifications of data points within the microbiome data, the classifications relating to the target environmental parameter.

16. The non-transitory machine-readable storage medium of claim 15, wherein the plurality of models is selected from a class of models based on structures inherent in the first subset of the microbiome data.

17. The non-transitory machine-readable storage medium of claim 14, wherein a constraint inherent in the microbiome data includes a diversity of data and the class of models includes generative models appropriate for the diversity.

* * * * *